(12) United States Patent
Lundeberg et al.

(10) Patent No.: US 6,482,592 B1
(45) Date of Patent: Nov. 19, 2002

(54) METHODS AND KITS FOR ISOLATING PRIMER EXTENSION PRODUCTS USING MODULAR OLIGONUCLEOTIDES

(75) Inventors: Joakim Lundeberg; Mathias Uhlen, both of Stockholm (SE)

(73) Assignee: Dynal AS, Oslo (NO)

( * ) Notice: Subject to any disclaimer, the term of this patent is extended or adjusted under 35 U.S.C. 154(b) by 0 days.

(21) Appl. No.: 09/153,242

(22) Filed: Sep. 15, 1998

Related U.S. Application Data

(63) Continuation-in-part of application No. PCT/GB97/02629, filed on Sep. 26, 1997.

(51) Int. Cl.⁷ .......................... C12Q 1/68; C12P 19/34; C07H 21/02; C07H 21/04; C07H 19/00
(52) U.S. Cl. .................. 435/6; 435/91.1; 435/91.2; 536/22.1; 536/23.1; 536/24.3; 536/24.31; 536/24.32; 536/24.33
(58) Field of Search .................. 435/6, 91.1, 91.2; 536/23.1, 25.32, 24.3, 24.31, 24.32, 24.33

(56) References Cited

U.S. PATENT DOCUMENTS

| | | | |
|---|---|---|---|
| 4,988,617 A | * | 1/1991 | Landegren et al. ............ 435/6 |
| 5,030,557 A | | 7/1991 | Hogan et al. |
| 5,149,625 A | | 9/1992 | Church et al. |
| 5,387,510 A | | 2/1995 | Wu |
| 5,428,145 A | | 6/1995 | Okamoto et al. |
| 5,547,843 A | | 8/1996 | Studier |
| 5,627,032 A | * | 5/1997 | Ulanovsky ............ 435/6 |
| 5,731,153 A | * | 3/1998 | Lucas et al. ............ 435/6 |
| 5,789,167 A | | 8/1998 | Konrad |
| 5,908,745 A | * | 6/1999 | Mirzabekov et al. ......... 435/6 |

FOREIGN PATENT DOCUMENTS

| | | | |
|---|---|---|---|
| EP | 0436547 B1 | * | 7/1991 |
| JP | 4084899 | | 3/1992 |
| WO | 9014442 | | 11/1990 |
| WO | WO 93/20232 A1 | | 10/1993 |
| WO | WO 98/13522 A1 | | 4/1998 |
| WO | WO 98/14610 A3 | | 4/1998 |
| WO | WO 98/14610 A2 | | 4/1998 |

OTHER PUBLICATIONS

Life Technologies Product Catalogue and Reference Guide R–90–R91 1995–1996.*

Nilsson, P., et al., Quantitative Investigation of the Modular Primer Effect for DNA and Peptide Nucleic Acid Hexamers, Anal. Biochem., Apr. 10, 1999, pp. 155–161, vol. 269, No. 1, Academic Press.

O'Meara et al., Cooperative Oligonucleotides Mediating Direct Captrue of Hepatitis C Virus RNA from Serum, J. Clin. Microbiol., Sep. 1998, pp. 2454–2459, vol. 36, No. 9, Ameraican Society for Microbiology.

PCT–Introduction to Biotechniques, C.R. Newton and A. Graham (eds), 1994, pp. 18–20, Bios. Scientific Publishers Ltd., Oxford, UK.

O'Meara et al., "Capture of Single–Stranded DNA Assisted by Oligonucleotide Modules," Anal. Biochem., Jan. 15, 1998, pp. 195–203, vol. 255, No. 2.

Abramova et al., *Dokl. Biochem.,* vol. 315, 1990, pp. 1485–1488 and Figs 1 and 2.

Beskin et al., *Nucl. Acids. Res.,* vol. 23(15), 1995, pp. 2881–2885.

Dunn et al., *Anal. Biochem.,* vol. 228, 1995, pp. 91–100.

Fu et al., *Proc. Natl. Acad. Sci., USA,* vol. 92, 1995, pp. 10162–10166.

Hou & Smith, *Anal. Biochem.,* vol. 221, 1994, pp. 136–141.

Kaczorowski & Szybalski, *Anal. Biochem.,* vol. 221, 1994, pp. 127–135.

Khrapko et al., *FEBS Letters,* vol. 256, 1989, pp. 118–122.

Khrapko et al., *DNA Seq.,* vol. 1, 1991, pp. 375–388.

Kieleczawa et al., *Science,* vol. 258, 1992, pp. 1787–1791.

Kotler et al., *BioTechniques,* vol. 17(3), 1994, pp. 554–558.

Kotler et al., *Proc. Natl. Acad. Sci. USA,* vol. 90, 1993, pp. 4241–4245.

Kramer and Lizardi, *Nature,* vol. 339, 1989, pp. 401–402.

Lin et al., *Biochemistry,* vol. 28, 1989, pp. 1054–1061.

Nilsson et al., *Anal. Biochem.,* vol. 224, 1995, pp. 400–408.

Szybalski, *Gene,* vol. 90, 1990, pp. 177–178.

Wetmur et al., *Crit. Rev. Biochem. Molec. Biol.,* vol. 26 (3/04), pp. 227–259.

* cited by examiner

*Primary Examiner*—Jeffrey Siew
(74) *Attorney, Agent, or Firm*—Rothwell, Figg, Ernst & Manbeck

(57) ABSTRACT

The invention provides a method of improving the binding of a series of consecutive nucleotide bases to a complementary target nucleic acid molecule in a sample, wherein said method comprises at least the step or steps of binding a complementary modular oligonucleotide of at least two parts (modules) including said nucleotide bases to adjacent stretches of said target nucleic acid molecule in said sample, especially methods of detection/isolation, particularly in the isolation of primer extension products and methods in which the modular oligonucleotide is a primer, modular oligonucleotides themselves and their use in methods of the invention.

16 Claims, 28 Drawing Sheets

| | 1 | 2 | 3 | 4 | 5 | 6 | 7 |
|---|---|---|---|---|---|---|---|
| IMMOBILISED PROBE | C1 | C1 | C1 | C2 | C2 | C2 | C2 |
| LENGTH (NUCLEOTIDES) | 18 | 18 | 18 | 9 | 9 | 9 | 9 |
| HYBRIDIZING PROBE(S) | H1 | H2 | – | H4+H1 | H5+H3 | H4+H3 | H4 |
| LENGTH (NUCLEOTIDES) | 11 | 11 | | 9+9 | 9+9 | 9+9 | 9 |
| GAP BETWEEN PROBES (NUCLEOTIDES) | – | 1 | – | – | 1 | 1 | – |
| SINGLE STRAND TARGET DNA | + | + | + | + | + | + | + |

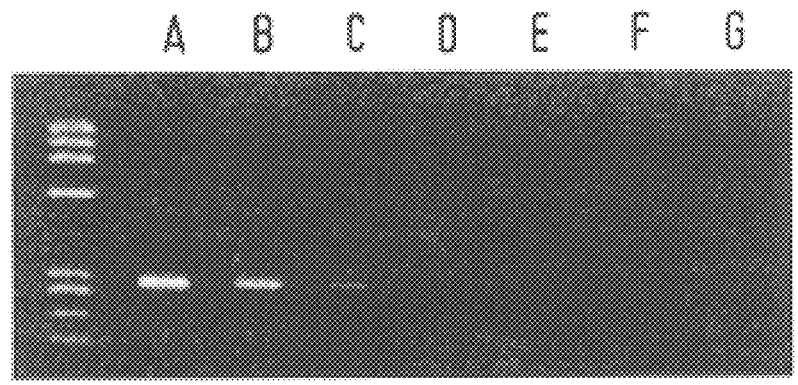
FIG.13

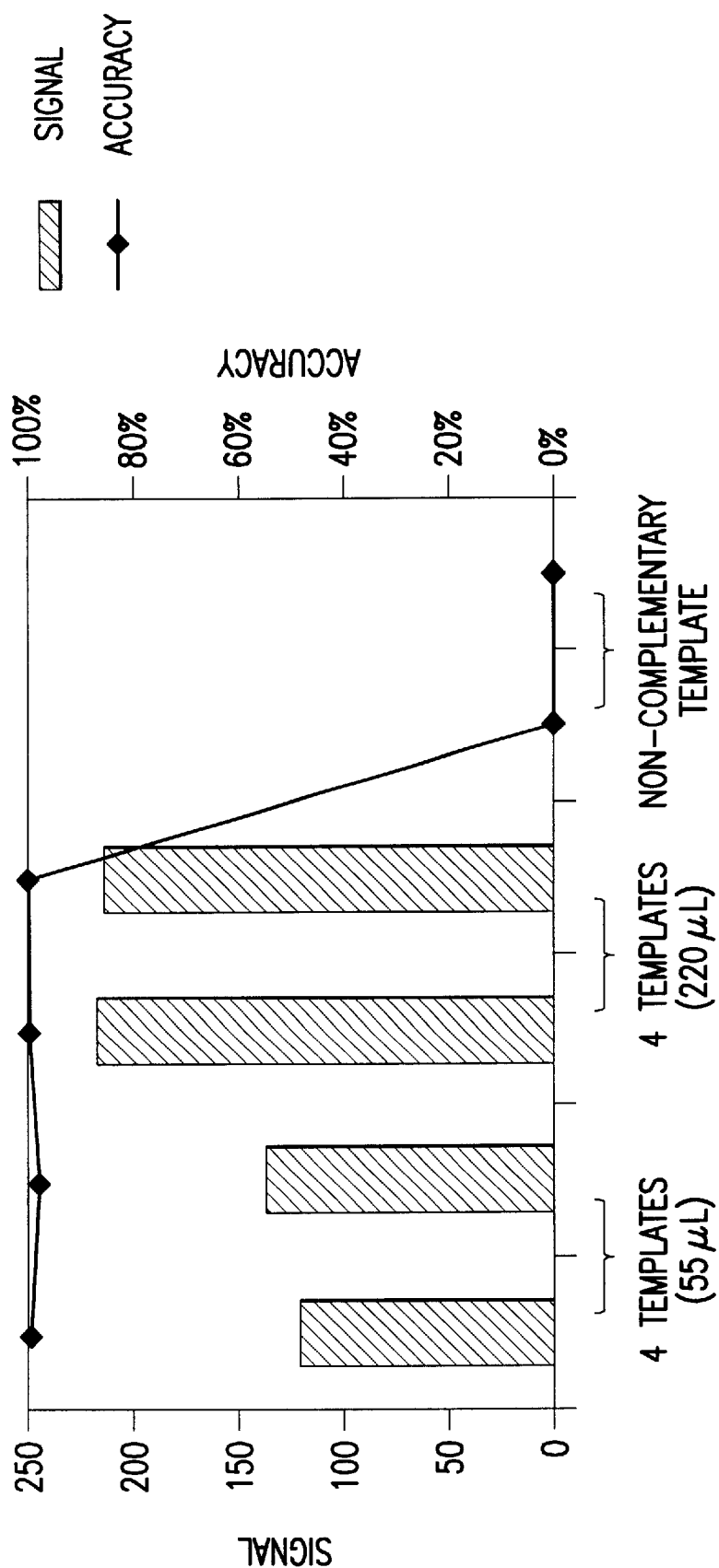

SEQUENCE LISTING

<160> NUMBER OF SEQ ID NOS: 63

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: JL-H1/USP

<400> SEQUENCE: 1 gacgtccag                                                                 9

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: JL-C2/USP

<400> SEQUENCE: 2 ctgagatct                                                                 9

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: JL-H2/USP

<400> SEQUENCE: 3
gttcgaacgt acg                                                           13

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: JL-C1/USP

<400> SEQUENCE: 4
gacgtccagc tgagatct                                                      18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: dedicated
      modular oligonucleotide

<400> SEQUENCE: 5
acccaattcg ccctatag                                                      18

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: dedicated
      modular oligonucleotide

<400> SEQUENCE: 6
tgagtcgtat tac                                                           13

```
<210> SEQ ID NO 7
<211> LENGTH: 11
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: n denotes the production of a family of
      degenerate oligonucleotides such that all possible
      permutations are produced
<223> OTHER INFORMATION: Description of Artificial Sequence:
      pUC/pRIT28, forward, capture probe, generic

<400> SEQUENCE: 7
nnaagcttac t                                                            11

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      pUC18/pRIT28, forward, modulating module, generic

<400> SEQUENCE: 8
ggccgtcgtt ttacaacg                                                     18

<210> SEQ ID NO 9
<211> LENGTH: 18
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: n denotes the production of a family of
      degenerate oligonucleotides such that all possible
      permutations are produced
<223> OTHER INFORMATION: Description of Artificial Sequence:
      pBluescript, forward, capture probe, generic

<400> SEQUENCE: 9
nnnnaattcg ccctatag                                                     18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: pUC18,
      reverse, capture probe, generic

<400> SEQUENCE: 10
gaattcacgg aaatcatg                                                     18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: pUC18,
      reverse, modulating module, generic

<400> SEQUENCE: 11
gtcatagctg tttcctgt                                                     18

<210> SEQ ID NO 12
<211> LENGTH: 15
<212> TYPE: DNA
<213> ORGANISM: Artificial Sequence
```

```
<220> FEATURE:
<223> OTHER INFORMATION: Description of Artificial Sequence:
      pBluescript, reverse, capture probe, generic

<400> SEQUENCE: 12
tccagctttt gttcc                                                    15

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:
      pBluescript, reverse, modulating module, generic

<400> SEQUENCE: 13
ctttagtgag ggttaatt                                                 18

<210> SEQ ID NO 14
<211> LENGTH: 17
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: n denotes the production of a family of
      degenerate oligonucleotides such that all possible
      permutations are produced
<223> OTHER INFORMATION: Description of Artificial Sequence:  pGEM3Z,
      reverse, capture probe, generic

<400> SEQUENCE: 14
nnttgagtat tctatag                                                  17

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: pGEM3Z,
      reverse, modulating module, generic

<400> SEQUENCE: 15
tgtcacctaa atagct                                                   16

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: pUC18,
      forward, capture probe, specific

<400> SEQUENCE: 16
tctagagtcg acctgcag                                                 18

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: pUC18,
      forward, modulating module, specific

<400> SEQUENCE: 17
gcatgcaagc tt                                                       12
```

```
<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: OU49

<400> SEQUENCE: 18
ggcgacactc caccatgaat c                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: OD66

<400> SEQUENCE: 19
ggtgcacggt ctacgagacc                                                20

<210> SEQ ID NO 20
<211> LENGTH: 52
<212> TYPE: DNA
<213> ORGANISM: Hepatitis C virus

<400> SEQUENCE: 20
tgcctgatag ggtgcttgcg agtgccccgg gaggtctcgt agaccgtgca cc            52

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide  c1

<400> SEQUENCE: 21
agagcatctg gcacgtgg                                                  18

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide  c1X10A

<400> SEQUENCE: 22
agagcatctg gcacgtggaa aaaaaaaa                                       28

<210> SEQ ID NO 23
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide  C3

<400> SEQUENCE: 23 ggcacgtgg                                                             9

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide C3

<210> SEQ ID NO 24
<400> SEQUENCE: 24
gggccctcca gagcatctgg cacgtgg                              27

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:   C4

<400> SEQUENCE: 25
acgctcacgg ggccctccag agcatctggc acgtgg                    36

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide  H1-18

<400> SEQUENCE: 26
acgctcacgg ggccctcc                                        18

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence:   H1-15

<400> SEQUENCE: 27
ctcacggggc cctcc                                           15

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence:   H1-13

<400> SEQUENCE: 28
cacggggccc tcc                                             13

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide    H1-11

<400> SEQUENCE: 29
cggggccctc c                                               11

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide    H1-9

<400> SEQUENCE: 30

```
gggccctcc                                                          9
```

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence:   H2

<400> SEQUENCE: 31

```
cctcc                                                              5
```

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide H2

<400> SEQUENCE: 32

```
acggggccct c                                                      11
```

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide H3

<400> SEQUENCE: 33

```
ggggccctc                                                          9
```

<210> SEQ ID NO 34
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide H4

<400> SEQUENCE: 34

```
agagcatct                                                          9
```

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonulcoetide H5

<400> SEQUENCE: 35

```
cagagcatc                                                          9
```

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide H6

<400> SEQUENCE: 36

```
gggccctcca gagcatct                                               18
```

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide H7

<400> SEQUENCE: 37
cggactatcc cacga                                                         15

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide H8

<400> SEQUENCE: 38 acgctcacg                                                                 9

<210> SEQ ID NO 39
<211> LENGTH: 36
<212> TYPE: DNA
<213> ORGANISM: Hepatitis C virus

<400> SEQUENCE: 39
ggagagccat agtggtctgc ggaaccggtg agtaca                                   36

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide OMD2

<400> SEQUENCE: 40
cgccttggcc actcatgt                                                       18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide OMD6

<400> SEQUENCE: 41
cctctcggta tcaccaga                                                       18

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide RIT 27

<400> SEQUENCE: 42
gcttccggct cgtatgttgt gtg                                                 23

<210> SEQ ID NO 43
<211> LENGTH: 23
<212> TYPE: DNA

<213> ORGANISM: Artificial Sequence
<220> FEATURE:
<223> OTHER INFORMATION: Description of Artificial Sequence: Synthetic
      Oligonucleotide RIT 28

<400> SEQUENCE: 43 aaaggggat gtgctgcaag gcg                                              23

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: PCR Primer
      JA79

<400> SEQUENCE: 44
acaggagcag atgatacagt attag                                           25

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: PCR Primer
      TV84

<400> SEQUENCE: 45
gacattcgaa ttcccttcct tttccatttc tgtac                                35

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: PCR Primer
      RIT29

<400> SEQUENCE: 46
gcttccggct cgtatgttgt gtg                                             23

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Modular
      oligonucleotide OMD82X13

<400> SEQUENCE: 47
ttaatttcgg tcc                                                        13

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Modular
      oligonucleotide OMD83

<400> SEQUENCE: 48
ttacctaccg ggttttca                                                   18

<210> SEQ ID NO 49
<211> LENGTH: 18
<212> TYPE: DNA
<213> ORGANISM: Artificial Sequence

```
<220> FEATURE:
<223> OTHER INFORMATION: Description of Artificial Sequence:  Modular
      oligonucleotide OMD81

<400> SEQUENCE: 49
aggataactt tgacatgg                                                        18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:  Modular
      Oligonucleotide OMD82

<400> SEQUENCE: 50
tcattttaat ttcggtcc                                                        18

<210> SEQ ID NO 51
<211> LENGTH: 36
<212> TYPE: DNA
<213> ORGANISM: HIV-1

<400> SEQUENCE: 51
tcctattgaa actgtaccag taaaattaaa gccagg                                    36

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence:  Forward
      sequencing primer

<400> SEQUENCE: 52
cgttgtaaaa cgacggccag t                                                    21

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:  Reverse
      sequencing primer

<400> SEQUENCE: 53
ttcacacagg aaacagctat gacc                                                 24

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:  Amersham/ET
      M13

<400> SEQUENCE: 54
tgtaaaacga cggccagt                                                        18

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence:  Amersham/ET
      M13 (-40)
```

```
<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence:  KTH USP

<400> SEQUENCE: 55
gttttcccag tcacg                                                    15

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:  KTH USP

<400> SEQUENCE: 56
cgttgtaaaa cgacggccag                                               20

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence:  USB
      Universal

<400> SEQUENCE: 57
gttttcccag tcacgacgtt gta                                           23

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:  FS pUC18
      Modular probe

<400> SEQUENCE: 58
tcacggttcg aacgtacg                                                 18

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence:  USB M13
      (-40)

<400> SEQUENCE: 59
gttttcccag tcacgac                                                  17

<210> SEQ ID NO 60
<211> LENGTH: 85
<212> TYPE: DNA
<213> ORGANISM: Artificial Sequence
<220> FEATURE:
<223> OTHER INFORMATION: Description of Artificial Sequence:  pRIT28
      Vector

<400> SEQUENCE: 60
ttgggtaacg ccagggtttt cccagtcacg acgttgtaaa acgacggcca gtaagcttgc   60
atgcctgcag gtcgactcta gagga                                         85

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence:  USB M13
      (-20)
```

```
<400> SEQUENCE: 61
gtaaaacgac ggccagt                                                    17

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence:  Primer

<400> SEQUENCE: 62
ggccagtgcc aagctt                                                     16

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:  Promega
      Forward (-48)

<400> SEQUENCE: 63
cgccagggtt ttcccagtca cgac                                            24
```

METHODS AND KITS FOR ISOLATING PRIMER EXTENSION PRODUCTS USING MODULAR OLIGONUCLEOTIDES

This application is a continuation-in-part of PCT/GB97/02629, filed Sep. 26, 1997.

FIELD OF THE INVENTION

The present invention relates to a method of improving the binding of a series of consecutive nucleotide bases to a complementary nucleic acid molecule, especially for use in improving the binding of capture oligonucleotides, in particular in methods for isolating primer extension products such as sequencing products, modular oligonucleotides and kits for performing methods of the invention.

BACKGROUND OF THE INVENTION

The binding of complementary nucleotide bases to one another represents one of the most significant and fundamental findings in science this century and heralded the rapid development of the field of biochemistry. Whilst allowing an understanding of the mechanisms underlying the continuation of life, the discovery has also provided the basis for the development of valuable molecular biological tools.

The isolation and sequencing of naturally occurring nucleic acid molecules is a common goal for molecular biologists. The use of complementary oligonucleotides to isolate nucleic acid molecules is commonplace. Similarly, complementary oligonucleotides are frequently used to bind single-stranded nucleic acid molecules and act as primers for extension reactions to produce complementary strands to the template and forms the basis of such experimental procedures as polymerase chain reaction (PCR) and sequencing reactions.

However, the specificity of binding of oligonucleotides to template or target DNA depends on a number of parameters any one of which may result in poor efficiency of binding and consequently poor experimental results. The specificity of the interaction may conveniently be determined by the assessment of $T_m$, the temperature at which duplexes dissociate. This is however also dependent on other parameters, for example the buffer in which the reaction is performed. For a particular experimental system, $T_m$ will be affected by various factors including the extent of complementarity, the sequence of the target and/or oligonucleotide, derivatization of the oligonucleotide and length of the oligonucleotide. The binding of oligonucleotides may therefore be improved, as evidenced by an increased $T_m$ under the same experimental conditions, by altering these parameters. However, the variation which may be achieved by altering these parameters is limited. There therefore exists a need for further methods which will improve the binding of oligonucleotides to target DNA.

SUMMARY OF THE INVENTION

Surprisingly, is has now been found that modular probes or primers composed of at least two modules (oligonucleotides) which bind to adjacent regions of target DNA exhibit improved binding relative to a single oligonucleotide spanning the same length as the separate modules (see WO98/13522). For example, it has been found that two adjacent 18-mer oligonucleotides bind more efficiently to target DNA than the composite 36-mer oligonucleotide.

The use of primers composed of adjacent modules for sequencing purposes has been described previously (Kotler et al., 1993, Proc. Natl. Acad. Sci. USA, 90, p4241–4245; Kieleczawa et al., 1992, Science, 258, p1787–1791 and Szybalski, 1990, Gene, 90, p177–178). However, in these cases the modular primers were used to replace longer primers such that libraries of all sequences of the shorter primers could realistically be pre-synthesized as they had fewer possible sequence permutations than longer primers. In all cases, the modular primers were only shown to have, in sequencing reactions under the same conditions, efficacy as good as the longer primers. In contrast, in the present invention, surprisingly, even better binding is achieved, when a single oligonucleotide is split into separate components. Furthermore, the previous work indicates that the effect of modular primers may only be achieved if the modules do not have a single (or more) base(s) between them when bound to the template. For improved binding as described herein, so such restriction is applicable although even better binding is observed when no gaps exist between the modules.

DESCRIPTION OF THE DRAWINGS

FIG. 13 shows the results of capture of HCV RNA from clinical hepatitis C samples onto magnetic beads in the absence or presence of an oligonucleotide module after single PCR.

FIG. 19 shows the specificity and background of the modular capture from multiple cycle sequencing reactions, tested with two beads types.

FIG. 20A uses the specific number modular oligonucleotides in Table 1 with pUC18 in the forward direction, FIG. 20B uses the specific modular oligonucleotide in Table 1 with pBluescript in the forward direction and FIG. 20C uses the generic modular oligonucleotide in Table 1 with pBluescript in the reverse direction.

DETAILED DESCRIPTION OF THE INVENTION

Figure 1A:
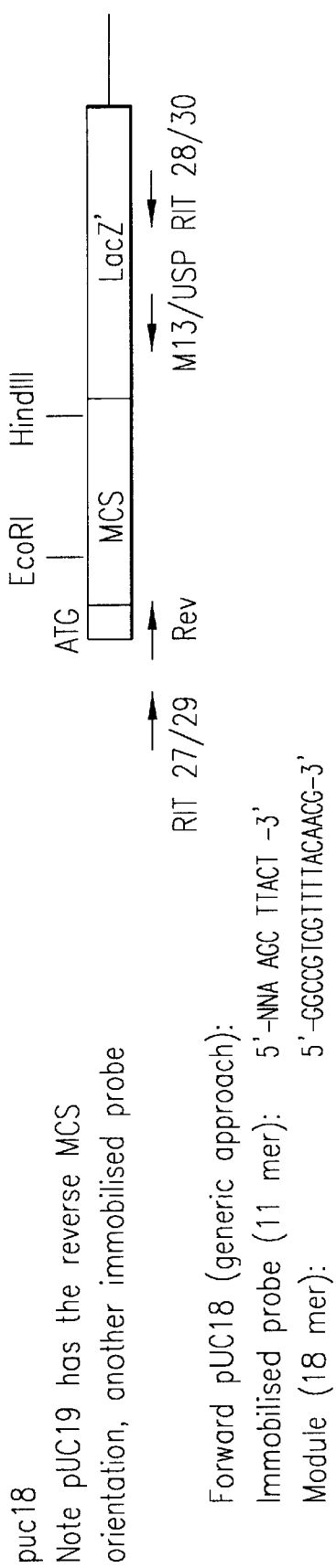
FIG. 1 is a schematic representation of modular oligonucleotides for use in isolating primer extension products generated from the vector pUC18 in the forward direction.

Viewed from one aspect, the present invention provides a method of improving the binding of a series of consecutive nucleotide bases to a complementary target consecutive nucleotide bases to a complementary target nucleic acid molecule in a sample, wherein said method comprises at least the step or steps of binding a complementary modular oligonucleotide of at least two parts including said nucleotide bases to adjacent stretches of said target nucleic acid molecule in said sample, wherein said molecular oligonucleotide exhibits improved binding relative to a single oligonucleotide complementary to the region of the target molecule spanned by the modular oligonucleotide.

Alternatively viewed, the present invention provides a method of binding a series of consecutive nucleotide bases to a complementary target nucleic acid molecule in a sample, wherein said method comprises at least the step or steps of binding a complementary modular oligonucleotide of at least three parts including said nucleotide bases to adjacent stretches of said target nucleic acid molecule in said sample.

As used herein, the term "improving" with respect to binding is intended to indicate increases specificity, stability or ability to bind to target nucleic acid molecules. "Binding" may be determined according to any method known in the art (for example as described herein) and will, as will be clear to the skilled addressee, be dependent on establishing appropriate buffer, temperature and other conditions. Binding of the modular oligonucleotide may be performed by binding all the parts thereof simultaneously or alternatively, sequential steps involving binding one or more of the modules at each step may be performed. "Complementary" as used herein is intended to encompass any series of consecutive nucleotide bases, oligonucleotide or target/template nucleic acid, as appropriate, which is complementary to the nucleotide sequence of the nucleic acid molecule in question, or its corresponding RNA, DNA, or nucleic acid analog, peptide nucleic acid (PNA). Modules of the modular oligonucleotide may be formed as a composite of the different nucleic acid molecules, e.g. DNA and PNA. Alternatively, individual modules may be composed exclusively of RNA, DNA or PNA, but different modules within the modular probe may be of a different nucleic acid. Thus, for example, a PNA module may be used as a capture probe whereas adjacent modules may be composed of DNA such that extension procedures (e.g. RT-PCR, DNA sequencing etc.) may be performed using the DNA module. Complementarity of the nucleic acid molecules includes within its scope non-absolute complementarity in which some mismatching may occur, although the "complementary" nucleic acids, or oligonucleotides or series of nucleotides, as appropriate, bind to one another under conditions of high stringency. Such oligonucleotides are those which bind under non-stringent conditions (e.g. 6×SSC/50% formamide at room temperature) and washed under conditions of high stringency (e.g. 2×SSC, 65° C.), wherein SSC=0.15M NaCl, 0.015M sodium citrate, pH 7.2.

"Nucleic acid molecule" is intended to cover inter alia RNA, mRNA, DNA, cDNA e.g. from retroviral RNA, genomic DNA, mitochondrial DNA etc. and PNA. The DNA may be single or double stranded. When double stranded DNA is used, appropriate procedures may be necessary to allow binding of the modular oligonucleotide, for example by heating to disrupt the structure to the single stranded form. "Target" nucleic acid includes molecules which are detected or isolated according to methods of the invention, e.g. primer extension or sequencing products, in addition to molecules which serve as a template for certain molecular reactions, for example, amplification, sequencing or transcription for the preparation of further distinct molecules. Nucleotide bases or oligonucleotides which bind to the target nucleic acid molecule may be modified or derivatized, providing they retain the ability to fulfill the complementarity requirements described above. For example, methylated, ethylated or carboxylated bases or other such modified or unusual bases may be used. Alternatively, the nucleic acid backbone may be modified, e.g. PNA units. Alternatively the base may carry a label, for example a hapten such as biotin or a dye. "Oligonucleotides" encompass any piece of DNA (or RNA after reverse transcription), RNA or PNA and extends also to the use of chimers of RNA, DNA and/or PNA.

"Modular oligonucleotide" refers to the primer/probe oligonucleotide which is composed of more than one part. Each part is an oligonucleotide which is referred to as a module of the whole. "Adjacent" as used herein is intended to signify non-overlapping regions of the nucleic acid molecule which lie close to one another, for example are less than 100 or 50 nucleotide bases apart, preferably 10 bases apart, especially preferably less than 2 bases apart, and most preferably without any bases in between, i.e. directly adjacent. Thus, the "single oligonucleotide" referred to above which comprises the modular oligonucleotide may include more nucleotides than the sum of the nucleotide bases in all parts of the modular oligonucleotide as the bases complementary to the region between the binding site of each module of the modular oligonucleotide will also be included in instances in which the modules, when bound, are not directly adjacent.

The method of the invention described herein may be used for any application in which improved binding of nucleotide bases, preferably in the form of an oligonucleotide, to a target nucleic acid molecule is required. Whilst not wishing to be bound by theory, it appears that the use of modular oligonucleotides allows the disruption of tertiary structures of nucleic acid molecules which are present not only in tRNA but also in other nucleic acid molecules. Such tertiary structures do not appear to be as effectively disrupted using longer oligonucleotides in which the parts of the modular oligonucleotide are synthesized together as a single molecule. Thus, applications which require improved binding to areas of nucleic acid molecules with tertiary structure which would prevent or impair binding of an oligonucleotide to this region, will benefit from this invention. The present invention therefore extends to, but is not limited to, applications in which the modular oligonucleotide serves as a primer in methods which involve replication, amplification, transcription, reverse transcription and/or sequencing, or in which the modular oligonucleotide serves as a probe for detection and/or capture or isolation of target nucleic acid molecules. It will be appreciated that in appropriate circumstances modular oligonucleotides may serve both of the aforementioned functions, e.g. by serving both as a primer and also as a capture/detection probe for the nucleic acid products e.g. amplified DNA, thus produced.

In the case of sequencing reactions, it may be found that a primer, regardless of its length is unable to provide the required products. Such a problem may be overcome by the use of a modular primer as an alternative to a composite primer. This may be achieved by simply including a second primer into the sequencing reaction in addition to the first primer, which binds at the front or rear of the first (sequencing) primer, an appropriate, and allows improved binding of the first primer to the template thereby causing or improving an appropriate sequencing reaction. Such improved binding, according to the definition of this invention, would not be observed if the second primer were simply ligated to the terminal end of the first sequencing primer. Alternatively, if the sequencing primer which gives a poor result is sufficiently long, a modular primer in which the sequencing primer is divided into at least two parts may be employed. If one of the modules of the primer is immobilized on a solid support, sequencing reactions may be performed directly on the support (Sanger T7 DNA polymerase sequencing) or used in cycle sequencing (Taq DNA polymerase).

In a similar way, the use of a modular primer may improve or cause replication, amplification, reverse transcription or transcription of a template nucleic acid molecule in a superior manner to that using a single primer composed of the separate modules.

The introduction of modules which bind adjacent to the primer in such reactions may enhance the reactions therefore increasing overall sensitivity. As indicated earlier, this invention may result from the disruption of tertiary structures in nucleic acid molecules. Tertiary structures have been reported to be of critical importance in the Q-beta replicase reaction (Kramer and Lizardi, 1989, Nature, 339, p.401–402). Thus, in a preferred aspect the invention provides a method of replication, amplification, transcription, reverse transcription and/or sequencing a target nucleic acid molecule in a sample, wherein said method comprises the binding of a complementary modular oligonucleotide as defined herein as a primer in the method.

Preferred applications of the present invention include the detection and/or capture of target nucleic acid molecules in which the binding of a probe to target nucleic acid is improved by the use of a modular probe with at least two parts. Such an application may be, for example, in Southern blot analyses for detecting target nucleic acid molecules to which a composite probe does not bind effectively. As used herein a composite is intended to mean that oligonucleotide which would result from the synthesis of appropriate modules as a continuous oligonucleotide, including the insertion of any necessary nucleotide bases complementary to the bases of the target nucleic acid between modules which are not directly adjacent. This may be improved by the use of a modular probe. Thus for example if a ten-mer oligonucleotide does not bind effectively to a target molecule, this may be replaced by two five-mer oligonucleotides, or a five-mer oligonucleotide may be added. In this way, the binding of the modular probes (comprising in total, in this example, 10 or 15 nucleotides) is improved relative to the binding of a composite probe of the 10 or 15 nucleotides (or more if the parts of the probe are not directly adjacent once bound to the target), respectively.

This method has been found to be highly effective for the detection and isolation or capture of target DNA in solution. In this method, a modular probe composed of at least two modules is employed. One module of the modular probe is the capture or detection module (or oligonucleotide). The further modules (modulators) assist by improving the binding of the capture module to the target molecule.

Thus, viewed from a further aspect, the present invention provides a method of detecting and/or isolating a target nucleic acid molecule in a sample, wherein said method comprises at least the step or steps of binding a complementary modular oligonucleotide of at least two parts to adjacent stretches of said target nucleic acid molecule in said sample.

Preferably for this method, if the capture or detection module the modulator module(s) were to form a single oligonucleotide probe, the binding efficiency would be decreased relative to the binding of the capture or detection module to the target in the presence of the free modulator modules.

Thus, viewed from a yet further aspect, the present invention provides a method of detecting and/or isolating a target nucleic acid molecule in a sample, wherein said method comprises at least the step or steps of binding a complementary modular oligonucleotide of at least two parts to adjacent stretches of said target nucleic acid molecule in said sample, wherein said modular oligonucleotide exhibits improved binding relative to a single oligonucleotide complementary to the region of the target molecule spanned by the modular oligonucleotide.

"Isolating" as used herein is intended to encompass the capture of target nucleic acid, even if this is not removed from the sample in which it is present, ie. physical separation or purification is not necessarily performed. Such methods involve the "capture" of the target from the sample in which it is contained by binding an oligonucleotide to it, thus effectively isolating it from other DNA molecules present in the sample. In methods of isolation the capture module will thus function also as the isolation module, allowing target molecules bound to it to be isolated.

Also provided according to the invention is a method of replication, amplification, transcription and/or reverse transcription of a target nucleic acid molecule in a sample, wherein said method comprises at least the step or steps of binding a complementary modular oligonucleotide of at least two parts to adjacent stretches of said target nucleic acid molecule in said sample.

Preferably, when isolation or capture is contemplated, the capture module is immobilized or has means for immobilization. Whilst modulating modules may be immobilized or carry means for immobilization, it will be appreciated that these will then effectively function as the capture module.

The means for immobilization may be inherently part of the nucleic acid sequence of the capture module, for example a poly T tail may be provided to bind to a solid support carrying a complementary oligo dA sequence. It will be appreciated that it is inadvisable to use a capture module with a poly A tail to be bound to a support carrying an oligo dT sequence as to do so may lead to the capture of mRNA which may be present in the sample. Other specific sequences which are complementary to sequences which can be attached directly or indirectly to an immobilizing support may also form part of the capture module for the purposes of immobilization.

The above methods involve the addition of further nucleotides to the capture module over those required for binding to the target nucleic acid. Extensions in this way are not always necessary and the means for immobilization may be introduced during or post oligonucleotide synthesis to nucleotides of the capture module to allow direct or indirect attachment to an immobilizing support through a binding partner. Conveniently, derivatized nucleotides may be used during synthesis to provide the appropriate first partner of the binding pair. The second partner of the binding pair is then carried on the support. Suitably derivatized capture oligonucleotides thus include those carrying biotin for binding to avidin or streptavidin, carrying epitopes or haptens (eg. digoxigenin) for binding to antibodies (which may be mono- or polyclonal) or antibody fragments or carrying DNA sequences for binding to DNA or PNA binding proteins (eg. the lac I repressor protein binding to a lac operator sequence attached to the oligonucleotide). Other suitable pairings include protein A-antibody, protein G-human serum albumin (HSA) and functional parts thereof. It will be appreciated that either of the partners of the binding pairs noted above, functional parts thereof, may bind to the oligonucleotide. The streptavidin/biotin binding system is very commonly used in molecular biology, due to the relative ease with which biotin can be incorporated within nucleotide sequences, and indeed the commercial availability of biotin-labelled nucleotides, and thus this represents one preferred method for attachment of the capture module to the support.

Numerous suitable supports for immobilization of oligonucleotides, and methods of attaching nucleotides to them, are well known in the art and widely described in the literature. Thus for example, supports in the form of sheets, gels, filters, membranes, microfibre strips, plates, microtiter wells, tubes, dipsticks, particles, fibres or capillaries may be used, made of a polymeric material for example of agarose, cellulose, alginate, teflon, latex or polystyrene. Particulate materials, especially beads, are generally preferred. For example, sepharose or polystyrene beads may be used. Advantageously, the support may comprise magnetic particles, eg. the superparamagnetic beads produced by Dynal AS (Oslo, Norway) and sold under the trademark DYNABEADS. Chips may be used as solid supports to provide miniature experimental systems as described for example in Nilsson et al. (1995, Anal. Biochem., 224, p400–408).

The solid support may carry functional groups such as hydroxyl, carboxyl, aldehyde or amino groups for the attachment of the capture module. These may in general be provided by treating the support to provide a surface coating of a polymer carrying one of such functional groups, eg. polyurethane together with a polyglycol to provide hydroxyl groups, or a cellulose derivative to provide hydroxyl groups, a polymer of copolymer of acrylic acid or methacrylic acid to provide carboxyl groups or an amino alkylated polymer to provide amino groups. U.S. Pat. No. 4,654,267 describes the introduction of many such surface coatings.

Alternatively, the support may carry other moieties for attachment, such as avidin or streptavidin, DNA binding proteins or antibodies or antibody fragments. Streptavidin-coated DYNABEADS are commercially available from Dynal AS. Preferably, immobilizing oligonucleotides are produced which bear a biotin moiety which may be used to attach to streptavidin on a solid support.

When detection of target nucleic acid is contemplated, which may or may not follow an isolation or capture method according to the invention, at least one of the modules of the modular oligonucleotide may be labelled.

The term "label" as used herein refers to any label which can be assessed qualitatively or quantitatively, directly or indirectly, eg. by virtue of its enzymatic properties, radiation emission, scattering or absorption properties, or of its ability to cooperate with or bind to a complimentary agent to produce a detectable effect, eg. interact with an enzyme to produce a signal, gas evolution, light emission, colour change, turbidity, precipitations etc. Such labels or means for labelling are well known, especially in the field of diagnostic assays and include for example, enzymes, chromophores or fluorophores (eg. dyes such as fluorescein and rhodamine), radiolabels, chemiluminescent compounds or reagents of high electron density such as ferritin, haemocyanin or colloidal gold. A label which uses enzyme activity to generate a colour for spectrophotometric assessment may be employed, for example $\beta$-galactosidase, alkaline phosphatase or peroxidase which on the addition of a suitable substrate may generate a signal suitable for detection.

Labels are conveniently introduced into parts of the modular oligonucleotide during or post synthesis. This may be achieved in a similar manner to providing a means for immobilization, by for example providing the oligonucleotide with one partner of a binding pair (pre or post synthesis), and subsequently attaching a second binding partner provided with a label. The first partner may be one of a conventional binding pair, for example biotin:streptavidin or may be part of the oligonucleotide sequence itself to which a second molecule will bind specifically. Alternatively, a derivatized nucleotide bearing a label, for example a radiolabelled nucleotide, may be used in the synthesis of the oligonucleotide or derivatized after synthesis. Alternatively, a module may be synthesized with a portion which is not complementary to the target nucleic acid which may inherently carry a label, e.g. a radiolabel, or be suitable for the attachment of a label. Such extensions to a module are not considered as part of the module when determining if improved binding is observed for a modular oligonucleotide compared to a single oligonucleotide spanning these modules, according to the definition of the invention. It will however be appreciated in the case of isolation of primer extension or sequencing products that generally it will be more convenient if the products to be isolated, are labelled, e.g. by any method described above, in particular by the use of a labelled (e.g. dye) primer for extension or the use of labelled terminator nucleotides. Such labelling is required particularly if the components of the modular oligonucleotides are removed prior to separation of the sequencing products.

Whilst detection may be achieved by using one or more labelled modules of the modular oligonucleotide to indicate binding, such a method has the advantage that the labelled modules bound to target nucleic acid must necessarily be separated from the binding reaction mix for detection above background levels to be possible. Although this separation may in most cases be performed readily, an alternative method of detection involves the use of labels on modules which bind to adjacent stretches of the target, which by their proximity generate a signal (negatively or positively) which may be detected. Such a label has the advantage not only that separation need not be performed for detection, although this may additionally be performed if required, but also that the signal is created only when modules bind adjacent to one another, thus reducing background noise. For example, modules with different labels may be used in which the labels are of sufficient proximity and suitable type that when the modules are bound to the target nucleic acid, they quench the possible fluorescence of the other label. Thus for example, two modules with different labels may be used, one of which is a quencher dye and the other a fluorescent dye. When not bound adjacent to one another fluorescence will occur, whereas when bound adjacent a measurable decrease in fluorescene may occur. Optionally, the target nucleic acid with bound quenching modules may be separated from unbound modules in the mixture. The bound molecules may then be released e.g. by heating to disrupt binding, thereby causing fluorescence as the labels on the modules separate allowing detectable fluorescence which may be correlated to the amount of the module bound and hence the amount of target DNA. Such labels are used in the TaqMan assay (Perkin Elmer).

It will however be appreciated that detection does not always rely on labelling the modules. For example, chip technology may be used, as described herein, in which the capture module of the modular probe is attached to the surface of the chip (see for example Nilsson et al., 1995, supra). When the capture module binds to the target DNA (in the presence of the modulating modules) a change in refractive index occurs at the sensor surface. This change correlates to the amount of target bound to the chip and thus may be used as a method of detection and/or isolation or capture. This method represents a preferred feature of the invention.

For performance of the invention, the method may additionally include the further step of attaching a capture module to a solid support in instances in which the module to a solid support in instances in which the module is provided with means for immobilization, prior or subsequent to the binding of the capture oligonucleotide to target nucleic acid by contacting the sample containing the target module with the immobilized capture oligonucleotide. Once bound to a solid support, washing steps may conveniently be performed, especially for purification purposes or to remove background in detection steps. Preferably, the capture oligonucleotide is bound to a solid support prior to the addition of a sample containing target nucleic acid molecules.

In methods of the invention, modulating modules are preferably added to, or contacted with, a sample containing the target nucleic acid molecules prior to the addition of the free or immobilized capture module, for example by mixing together at 54° C. for 45 minutes followed by cooling to room temperature to allow hybridization.

In procedures employing methods of the invention, especially assay procedures, additional steps of isolation, separation, purification, assessment and/or comparison may be performed as appropriate to obtain the desired results. Thus, for example a method of the invention may comprise at least one of the following additional steps:

a) attaching the capture module of the modular oligonucleotide to a solid support in instances in which the capture module is provided with a means for immobilization;

b) contacting the sample containing the target nucleic acid with the modular oligonucleotide;

c) contacting the sample containing the target nucleic acid with the modulating modules of the modular oligonucleotide;

d) contacting the sample containing the target nucleic acid with the immobilized capture oligonucleotide to allow binding of the oligonucleotide to target nucleic acid;

e) separating target nucleic acid bound to the capture module from the sample;

f) washing the target nucleic acid separated in (e) above;

g) assessing the presence or amount of label associated with the target nucleic acid (e.g. after separation of the primer extension/sequencing products), when labelled modules are used, or assessing the presence or amount of target nucleic acid bound to the capture module when no label is employed; and h) comparing the amount of label, or bound target nucleic acid of (g) with control levels.

It will be appreciated that not all of the above steps may be incorporated into any given procedure as for example, steps (c) and (d) essentially perform step (b) in two parts. In step (g), assessment of label or bound target molecules may alternatively be performed by assessment of label not associated with target molecules or assessment of unbound nucleic acid, which values may then be subtracted from total values of label or nucleic acid used to give the required value of label or bound target nucleic acid. Whilst these values may be correlated to appropriate standard curves to obtain absolute values, this is not essential, and the term "assessing" as used herein includes both quantitation in the sense of obtaining an absolute value for the amount of target nucleic acid in a sample, and also obtaining a semi-quantitative or qualitative assessment, for example to indicate simply the presence of target nucleic acid in the sample under study. Assessment may also involve the generation of further molecules for detection, for example by sequencing and/or amplification reactions. With regard to step (h), suitable control levels will be those established using the same experimental procedures for non-test or normal samples. It will be clear that different sequential steps may be employed to achieve binding of the modular oligonucleotide. For example, a part of the modular oligonucleotide may be contacted with the sample and then bound, followed by contacting and binding of further parts of the modular oligonucleotide. Alternatively the contacting steps may be performed simultaneously.

In a preferred aspect of the invention, the method may comprise the steps of:

1) contacting the sample containing the target nucleic acid with all modules of the modular oligonucleotide;
2) binding said modules by hybridization;
3) addition of a solid support and attachment of at least one of said modules provided with a means for immobilization to said solid support;
4) separating target nucleic acid bound to said solid support;
5) washing said solid support;
6) amplification of said target nucleic acid; and
7) assessing the presence or amount of amplified nucleic acid.

It will be appreciated that modular oligonucleotides which have utility according to the invention may be made up of different numbers of modules (with or without spaces between them when bound to target nucleic acid molecules), each of which may be different sizes. While this invention has been found to have utility when tested at different target DNA sites, some appropriate modification of module number and/or module size may be appropriate to obtain optimum binding at a given site under particular experimental conditions. Such optimization is within the scope of the skilled addressee in which trial and error experimental of the type illustrated herein may be employed. Thus, in general, 5 or fewer modules make up the modular oligonucleotide, preferably 2 or 3 modules, with each module containing 4 or more nucleotide bases. Preferably the modular oligonucleotide contains a total of at least 10 nucleotides, preferably at least 18, for example 18, 24, 27, 29, 31, 33 or 36. Modules, when bound to target nucleic acid are preferably less than 10 nucleotide bases apart, especially preferably less than 2 bases apart, particularly preferably, without any bases in between. It is especially preferred that less than 2 bases separate the capture module and first adjacent modulating module when bound to the target.

Specifically preferred features of modular oligonucleotides for use in the invention are those with 2 or 3 modules, each module with >5 nucleotides, preferably ≧9≦18, eg. 9, 11, 13, 15 or 18 nucleotides. When 3 modules are employed, slightly shorter modules may be used than when 2 modules are used such that the total nucleotides in 2-part modular oligonucleotides are >27, preferably ≧29, eg. 29, 31, 33 or 36 and in 3-part modular oligonucleotides >23, preferably ≧27, eg. 27, 31, 33 or 36 nucleotides.

The modules of the modular oligonucleotides may be prepared by chemical or other appropriate synthesis well known in the art. Several useful oligonucleotides are available commercially with an attached biotin molecule for immobilization (e.g. KEBO, Stockholm, Sweden).

The method has utility especially with regard to viral target nucleic acid, for example Hepatitis C virus (HCV) and may be used to monitor or diagnose viral or other infections. Suitable modular oligonucleotides for use in methods of the invention include modular oligonucleotides having one of the following sequences: For detection, isolation or capture of HCV at positions 291–341:

H1-18+C1 (18+18) 3'-ACGCTCACGGGGCCCTCC-5' (SEQ ID NO.26)+3'-AGAGCATCTGGCACGTGG-5' (SEQ ID NO.21)

H2+C1 (11+18) 3'-ACGGGGCCCTC-5'+3'(SEQ ID NO.32)-AGAGCATCTGGCACGTGG-5'(SEQ ID NO.21)

H1-15+C1 (15+18) 3'-CTCACGGGGCCCTCC-5'(SEQ ID NO.27)+3'-AGAGCATCTGGCACGTGG-5'(SEQ ID NO.21)

H1-13+C1 (13+18) 3'-CACGGGGCCCTCC-5'(SEQ ID NO.28)+3'-AGAGCATCTGGCACGTGG-5'(SEQ ID NO.21)

H1-11+C1 (11+18) 3'-CGGGGCCCTCC-5'(SEQ ID NO.29)+3'-AGAGCATCTGGCACGTGG-5'(SEQ ID NO.21)

H8+H1-9+C1 (9+9+18) 3'-ACGCTCACG-5'(SEQ ID NO.38)+3'-GGGCCCTCC-5'(SEQ ID NO.30) 3'-AGAGCATCTGGCACGTGG-5'(SEQ ID NO.21)

H1-18+H4+C2 (18+9+9) 3'-ACGCTCACGGGGCCCTCC-5'(SEQ ID NO.26)+3'-AGAGCATCT-5'(SEQ ID NO.34)+3'-GGCACGTGG-5'(SEQ ID NO.23)

H1-15+H4+C2 (15+9+9) 3'-CTCACGGGGCCCTCC-5'(SEQ ID NO.27)+3'-AGAGCATCT-5'(SEQ ID NO.34)+3'-GGCACGTGG-5'(SEQ ID NO.23)

H1-13+H4+C2 (13+9+9) 3'-CACGGGGCCCTCC-5'(SEQ ID NO:28)+3'-AGAGCATCT-5'(SEQ ID NO:34)+3'-GGCACGTGG-5'(SEQ ID NO:23)

H1-11+H4+C2 (11+9+9) 3'-CGGGGCCCTCC-5'(SEQ ID NO:29)+3'-AGAGCATCT-5'(SEQ ID NO:34)+3'-GGCACGTGG-5'(SEQ ID NO:23)

H1-9+H4+C2 (9+9+9) 3'-GGGCCCTCC-5'(SEQ ID NO.30)+3'-AGAGCATCT-5'(SEQ ID NO.31)+3'-GGCACGTGG-5'(SEQ ID NO.23)

H3+H5+C2 (9+9+9) 3'-GGGGCCCTC-5'(SEQ ID NO:33)+3'-CAGAGCATC-5'(SEQ ID NO.35)+3'-GGCACGTGG-5'(SEQ ID NO.23)

H3+H4+C2 (9+9+9) 3'-GGGGCCCTC-5'(SEQ ID NO.33)+3'-AGAGCATCT-5'(SEQ ID NO.34)+3'-GGCACGTGG-5'(SEQ ID NO.35)

For detection, isolation or capture of HCV at positions 132–167:

OMD6+OMD2 (18+18) 3'-CCTCTCGGTATCACCAGA-5' (SEQ ID NO.41)+3'-CGCCTTGGCCACTCATGT-5' (SEQ ID NO.40)

Preferably in the above modular oligonucleotides, the last listed module is the capture module (ie. C1, C2 or OMD2) and may bear a moiety for immobilization, preferably a biotin molecule at the 5' end. These modular oligonucleotides and others suitable for use in methods of the invention form further aspects of the invention. Thus in a yet still further aspect, the present invention provides methods of the invention for detecting and/or isolating HCV, wherein said oligonucleotides comprise one of the following nucleotide sequences:

3'-ACGCTCACGGGGCCCTCC-5'(SEQ ID NO.26)+3'-AGAGCATCTGGCACGTGG-5'(SEQ ID NO.21); or

3'-ACGGGGCCCTC-5'(SEQ ID NO.32)+3'-AGAGCATCTGGCACGTGG-5'(SEQ ID NO.21); or

3'-CTCACGGGGCCCTCC-5'(SEQ ID NO.27)+3'-AGAGCATCTGGCACGTGG-5'(SEQ ID NO.21); or

3'-CACGGGGCCCTCC-5'(SEQ ID NO.28)+3'-AGAGCATCTGGCACGTGG-5'(SEQ ID NO.21); or

3'-CGGGGCCCTCC-5'(SEQ ID NO.29)+3'-AGAGCATCTGGCACGTGG-5'(SEQ ID NO.21); or

3'-ACGCTCACG-5'(SEQ ID NO.30)+3'-GGGCCCTCC-5'(SEQ ID NO.30)+ 3'-AGAGCATCTGGCACGTGG-5'(SEQ ID NO.21); or

3'-ACGCTCACGGGGCCCTCC-5'(SEQ ID NO.26)+3'-AGAGCATCT-5'(SEQ ID NO.34)+3'-GGCACGTGG-5'(SEQ ID NO.33); or

3'-CTCACGGGGCCCTCC-5'(SEQ ID NO.27)+3'-AGAGCATCT-5'(SEQ ID NO.34)+3'-GGCACGTGG-5' (SEQ ID NO.23); or

3'-CACGGGGCCCTCC-5'(SEQ ID NO.28)+3'-AGAGCATCT-5'(SEQ ID NO.34)+3'-GGCACGTGG-5' (SEQ ID NO.23); or

3'-CGGGGCCCTCC-5'(SEQ ID NO.29)+3'-AGAGCATCT-5'(SEQ ID NO.34)+3'-GGCACGTGG-5' (SEQ ID NO.23); or

3'-GGGCCCTCC-5'(SEQ ID NO.30)+3'-AGAGCATCT-5' (SEQ ID NO.34)+3'-GGCACGTGG-5'(SEQ ID NO.23); or

3'-GGGGCCCTC-5'(SEQ ID NO.33)+3'-CAGAGCATC-5' (SEQ ID NO.35)+3'-GGCACGTGG-5'(SEQ ID NO.23); or

3'-GGGGCCCTC-5'(SEQ ID NO.33)+3'-AGAGCATCT-5' (SEQ ID NO.34)+3'-GGCACGTGG-5'(SEQ ID NO.23); or

3'-CCTCTCGGTATCACCAGA-5'(SEQ ID NO.41)+3'-CGCCTTGGCCACTCATGT-5'(SEQ ID NO.40), or analogs or derivatives thereof.

The invention also has utility with regard to identifying and/or isolating target HIV nucleic acid. In this respect, modular probes directed to the polymerase region of HIV-1 have been designed to allow capture and/or isolation of the HIV RNA genome for diagnostic purposes. Although HIV RNA contains poly A which enables purification by binding to a solid support bearing oligo-dT, conveniently using the method of the invention, a capture oligonucleotide is used which binds adjacent to the site where RT-PCR primers would be located such that the effects of RNAses are minimized. In this respect, suitable modular oligonucleotides for use in the methods of the invention include modular oligonucleotides having one of the following sequences:

OMD82×13+OMD83 3'-TTAATTTCGGTCC-5'(SEQ ID NO.47)+3'-TTACCTACCGGGTTTTCA-5'(SEQ ID NO.48)

OMD81+OMD82 (18+18) 3'-AGGATAACTTTGACATGG-5'(SEQ ID NO.49)+3'-TCATTTTAATTTCGGTCC-5'(SEQ ID NO.50).

Preferably in the above modular oligonucleotides, the last listed module is the capture module (ie. OMD82, 83) and may bear a moiety for immobilization, preferably a biotin molecule at the 5' end. These modular oligonucleotides and other suitable for use in methods of the invention form further aspects of the invention. Thus in a yet still further aspect, the present invention provides methods of the invention for detecting and/or isolating HIV, wherein said oligonucleotides comprise one of the following nucleotide sequences:

3'-TTAATTTCGGTCC-5' (SEQ ID NO.47)+3'-TTACCTACCGGGTTTTCA-5' (SEQ ID NO.48); or

3'-AGGATAACTTTGACATGG-5' (SEQ ID NO.49)+3'-TCATTTTAATTTCGGTCC-5' (SEQ ID NO.50), or analogs or derivatives thereof.

The invention also has utility with regard to identifying and/or isolating sequencing products generated by the extension of primers, for example the universal sequencing primer (USP). Such products need to be purified and/or enriched after synthesis before loading onto an electrophoresis system. In large genomic sequencing projects, where large numbers of samples are handled, automation is an important requirement. Assays that include precipitation, extraction or centrifugation steps are difficult to automate. Although alcohol precipitation is routinely used in laboratory protocols, this is not easy to automate. The use of modular probes allows the capture of such products as generated by, for example, traditional T7 DNA polymerase sequencing or cycle sequencing protocols.

Thus viewed from a further aspect the present invention provides a method of isolating primer extension products, wherein said method comprises at least the step or steps of binding a complementary modular oligonucleotide of at least two parts (modules) to adjacent stretches on said primer extension products, wherein at least one module (capture module) is immobilized or has means for immobilization. Preferably said modular oligonucleotide exhibits improved binding relative to a single oligonucleotide complementary to the region of the target molecule (herein referred to as the primer extension product or the sequencing product) spanned by the modular oligonucleotide.

Whilst the separate modules may be added separately, in a preferred embodiment, said primer extension products are contacted directly with all modules of said modular oligonucleotide in a single hybridization step.

In a preferred embodiment, a modular oligonucleotide of two modules is employed and one of said modules, the capture module, is immobilized on a solid support.

To develop methods suitable for large scale use, it is also important to consider the costs of sequence product purification per sample. Whereas previous methods relied on the purification and concentration of Sanger fragments prior to separation by gel electrophoresis (although spin-columns have also been used), since the use of modular oligonucleotides for isolation relies on a hybridisation event, re-use of the solid support, for example paramagnetic beads is possible.

It will be appreciated that this new method may be adapted for use with respect to different primers used to synthesize extension products. Thus, for example, in the primer extension products produced by a particular primer, a region will exist which corresponds to that primer and that region may be used to isolate the primer extension products by producing a modular oligonucleotide complementary to that region.

However, such methods have the limitation that free primer and misprimed products will both bind to, and hence be captured by, the modular oligonucleotides. This thus offers little advantage over the use of ethanol precipitation (which would precipitate all such products) other than the potential for automation.

It has however now been found that modular oligonucleotides of the invention may be directed to regions of the primer extension products other than the primer-derived regions and such methods offer surprisingly advantageous results.

In the design of these modular oligonucleotides, consideration was taken of the two main DNA sequencing chemistries, namely the use of dye terminators, or dye primers, for both cycle sequencing (Taq DNA polymerase or derivative) as well as isothermal protocols (T7 DNA polymerase or derivative), so that the modular oligonucleotides are compatible with either system. Importantly, the immobilised capture probe is not sufficiently complementary to the sequencing primer, which is employed to generate the sequencing products, to allow any sequence corresponding to the primer sequence to be captured. In the case of dye primer chemistry this results in unused labelled dye primer not being co-purified with extended Sanger fragments, which serves to reduce the background in the chromatograms. Furthermore, surprisingly, this also serves to improve the accuracy of sequencing as described later in more detail and in the Examples herein. In the case of dye terminator chemistry (as well as for dye primers) misprimed sequencing products are not purified due to the lack of complementarity between the misprimed product and the capture probe. Again this reduces background and may also improve accuracy of sequencing.

In these new methods, two different approaches have been taken to the design of modular oligonucleotides. Firstly, dedicated or specific modular oligonucleotides have been designed which are specifically appropriate for use in large scale projects in which the same vector and cloning site of the insert are used extensively. In this case the modular oligonucleotides anneal in parts of the multiple cloning site of the vector which are kept intact after cloning of the insert.

For example, for capture of the products of universal primer extension reactions in the forward direction for inserts in the vector, suitable modular oligonucleotides for use in methods of the invention include modular oligonucleotides having one of the following sequences:

JL-H1/USP+JL-C2/USP (9+9) 3'-GACGTCCAG-5' (SEQ ID NO.1)+3'-CTGAGATCT-5' (SEQ ID NO.2)

JL-H2/USP+JL-C1/USP (13+18) 3'-GTTCGAACGTACG-5' (SEQ ID NO.3)+3'-GACGTCCAGCTGAGATCT-5' (SEQ ID NO.4)

JL-H2/USP+JL-H1/USP+JL-C2/USP (13+9+9) 3'-GTTCGAACGTACG-5' (SEQ ID NO.3)+3'-GACGTCCAG-5' (SEQ ID NO.1)+3'-CTGAGATCT-5' (SEQ ID NO.2)

Preferably in the above modular oligonucleotides, the last listed module is the capture module (ie. JL-C1/USP, JL-C2/USP) and may bear a moiety for immobilization, preferably a biotin molecule at the 5' end. Thus in a yet still further aspect, the present invention provides methods of the invention for detecting and/or isolating primer extension products, especially of the primer, USP, in the forward direction for inserts in the vector pUC18, wherein said oligonucleotides comprise one of the following nucleotide sequences:

3'-GACGTCCAG-5' (SEQ ID NO.1)+3'-CTGAGATCT-5' (SEQ ID NO.2); or

3'-GTTCGAACGTACG-5' (SEQ ID NO.3)+3'-GACGTCCAGCTGAGATCT-5' (SEQ ID NO.4); or

3'-GTTCGAACGTACG-5' (SEQ ID NO.3)+3'-GACGTCCAG-5' (SEQ ID NO.1)+3'-CTGAGATCT-5' (SEQ ID NO.2), or analogs or derivatives thereof.

A further example of a dedicated modular oligonucleotide of the invention is provided by oligonucleotides which have the sequence:

5'-ACCCAATTCGCCCTATAG-3' (SEQ ID NO.5)+5'-TGAGTCGTATTAC-3' (SEQ ID NO.6), or analogs or derivatives thereof. Especially preferably the first stated oligonucleotide behaves as the capture probe and the second oligonucleotide as the modulating module.

Analogs and derivatives as referred to herein include modified or derivatized nucleotide bases or oligonucleotides as referred to previously, which retain their ability to fulfill the complementarity requirements described herein and which include for example, nucleotides bearing labels or means for immobilization. Alternatively, particular bases defined above may be replaced by other non-complementary bases or derivatized bases which do not prevent binding to the target nucleic acid to such an extent as to fall outside the definition of complementarity as described herein.

These modular oligonucleotides and others suitable for use in methods of the invention form further aspects of the invention.

The second approach to the design of suitable modular oligonucleotides to capture primer extension products is the production of generic modular oligonucleotides which are able to bind to and capture primer extension products from any insert cloned into the multiple cloning site of a given vector, ie. even the most extreme positioned restriction sites may be used for cloning. The following table provides details of a number of modular oligonucleotides of the generic (and specific) type of the invention which may be used for the collection of primer extension products produced from the specified vectors into which nucleic acid inserts have been cloned.

TABLE 1

Generic and specific modular oligonucleotides for isolation of primer extension products

GENERIC MODULAR OLIGONUCLEOTIDES

| VECTOR | DIRECTION | CAPTURE PROBE* | MODULATING MODULE |
|---|---|---|---|
| pUC18 | Forward | 5'-NAAGCTTACT-3' (SEQ ID NO.7) | 5'-GGCCGTCGTTTTACAACG-3' (SEQ ID NO.8) |
| pBluescript, pBluescript II, pGEM3Z and 5Z | Forward | 5' NNNNAATTCGCCCTATG-3' (SEQ ID NO.9) | 5'-TGAGTCGTATTAC-3' (SEQ ID NO.6) |
| pUC18 | Reverse | 5'-GAATTCACGGAAATCATG-3' (SEQ ID NO.10) | 5'-GTCATAGCTGTTTCCTGT-3' (SEQ ID NO.11) |
| pBluescript and pBluescript II | Reverse | 5'-TCCAGCTTTTGTTCC-3' (SEQ ID NO.12) | 5'-CTTTAGTGAGGGTTAATT-3' (SEQ ID NO.13) |
| pGEM3Z and 5Z | Reverse | 5'-NNTTGAGTATTCTATAG-3' (SEQ ID NO.14) | 5'-TGTCACCTAAATAGCT-3' (SEQ ID NO.15) |

SPECIFIC MODULAR OLIGONUCLEOTIDES

| VECTOR | DIRECTION | CAPTURE PROBE | MODULATING MODULE |
|---|---|---|---|
| pUC18 | Forward | 5'-TCTAGAGTCGACCTGCAG-3' (SEQ ID NO.16) | 5'-GCATGCAAGCTT-3' (SEQ ID NO.17) |
| pBluescript and pBluescript II | Forward | 5'-ACCCAATTCGCCCTATAG-3' (SEQ ID NO.5) | 5'-TGAGTCGTATTAC-3' (SEQ ID NO.6) |

TABLE 1-continued

Generic and specific modular oligonucleotides for isolation of primer extension products

*N denotes the production of a family of degenerate oligonucleotides such that all possible permutations are produced Thus viewed from a further aspect the present invention provides a method of isolating primer extension products produced from a template vector, said products containing sequences corresponding or complementary to i) a primer binding region, ii) an insert and iii) vector-derived sequence (s), wherein said method comprises at least the step or steps of binding a modular oligonucleotide of at least two parts (modules) to adjacent stretches on said primer extension products, wherein said modular oligonucleotide is complementary to and capable of binding to said vector-derived sequences of said primer extension products, wherein at least one module (capture module) is immobilized or has means for immobilization.

As referred to herein, reference to a primer binding region, the insert and vector-derived sequences includes sequences which are complementary thereto and it will be appreciated for example that modular oligonucleotides of the invention bind to vector-derived regions of the primer extension product and thus are complementary thereto and have a corresponding sequence to the original vector.

As used herein reference to a "template vector" refers to any piece of nucleic acid from which primer extension products may be produced, ie. susceptible to nucleic acid extension reactions, comprising a primer binding region, an insert (a portion of DNA, e.g. for sequencing) and further regions to which the modular oligonucleotide may be directed. In preferred embodiments said template vectors are vectors which are known in the art, such as pBluescript SK or II SK, pGEM-3Z, 4Z or 5Z, pUC18 or pUC19, which comprise additional sequences of varied functionality. In such cases, the "insert" is a portion of nucleic acid which in inserted into a restriction site of the vector through the use of appropriate restriction enzymes. The insert may however be provided in the template vector by other means such as by ligation.

As mentioned previously, in the present invention modular oligonucleotides are used which avoid isolation of primers or misprimed products. For this purpose, as stated above, such modular oligonucleotides are complementary to and capable of binding to vector-derived sequences. It will however be appreciated that some complementarity may exist between one or more modules of the modular oligonucleotide and the primer binding region and/or the insert providing that as a whole, the complementarity and hence binding is not sufficient to allow capture of primers or misprimed products. Thus for example a portion of one of the modules of the modular oligonucleotide may be complementary to the primer binding sequence (or the insert), e.g. less than 4 base pairs, but this would be insufficient to allow capture of the primer. Furthermore, since the complementarity of the capture module ultimately dictates which molecules are captured, the other non-capture modules of the modular oligonucleotide may be fully complementary to the primer binding sequence (or the insert), but providing the capture module is not sufficiently complementary to the primer binding sequence to allow its capture, undesired products will not be captured. In the latter case it might be necessary to increase the concentration of the modulating modules to account for the binding to unincorporated primers.

In the above cases some complementarity to the primer sequence may occur without the capture of unincorporated primers or misprimed products. Complementarity to the insert can also be tolerated, although in such cases it is desirable to capture primer extension products containing regions corresponding to the insert. Thus to allow their capture, appropriate regions of the modular oligonucleotide may be synthesized as a set of degenerate nucleotides such that all possible variations are covered and thus regardless of the sequence of the insert the necessary binding to the modules will occur. It is however preferred that the modular oligonucleotide is complementary to only vector-derived sequences.

As mentioned above, in the specific approach the vector-derived sequence(s) as described above is derived from any region of a particular vector and contains a portion which remains intact after cloning of the insert into a particular restriction site of the multiple cloning site of said vector and to which the modular oligonucleotide anneals. Preferably, said portion of the vector to which the modular oligonucleotide anneals is derived from the multiple cloning site or surrounding sequences.

In the generic approach, the vector-derived sequence(s) as described above is derived from any region of a particular vector and contains a portion which remains intact after cloning of the insert regardless of the restriction site of the multiple cloning site of a particular vector into which the insert is cloned, and to which the modular oligonucleotide anneals. Preferably, said portion of the vector to which the modular oligonucleotide anneals is derived from the multiple cloning site or surrounding sequences, especially preferably the sequences preceding, the multiple cloning site. Selection of an appropriate sequence will depend on the vector to be used. In some case the generic approach may not be possible if undisturbed vector-derived sequences are too small. In such case specific approach modular oligonucleotides may be more appropriate.

Figure 1B:
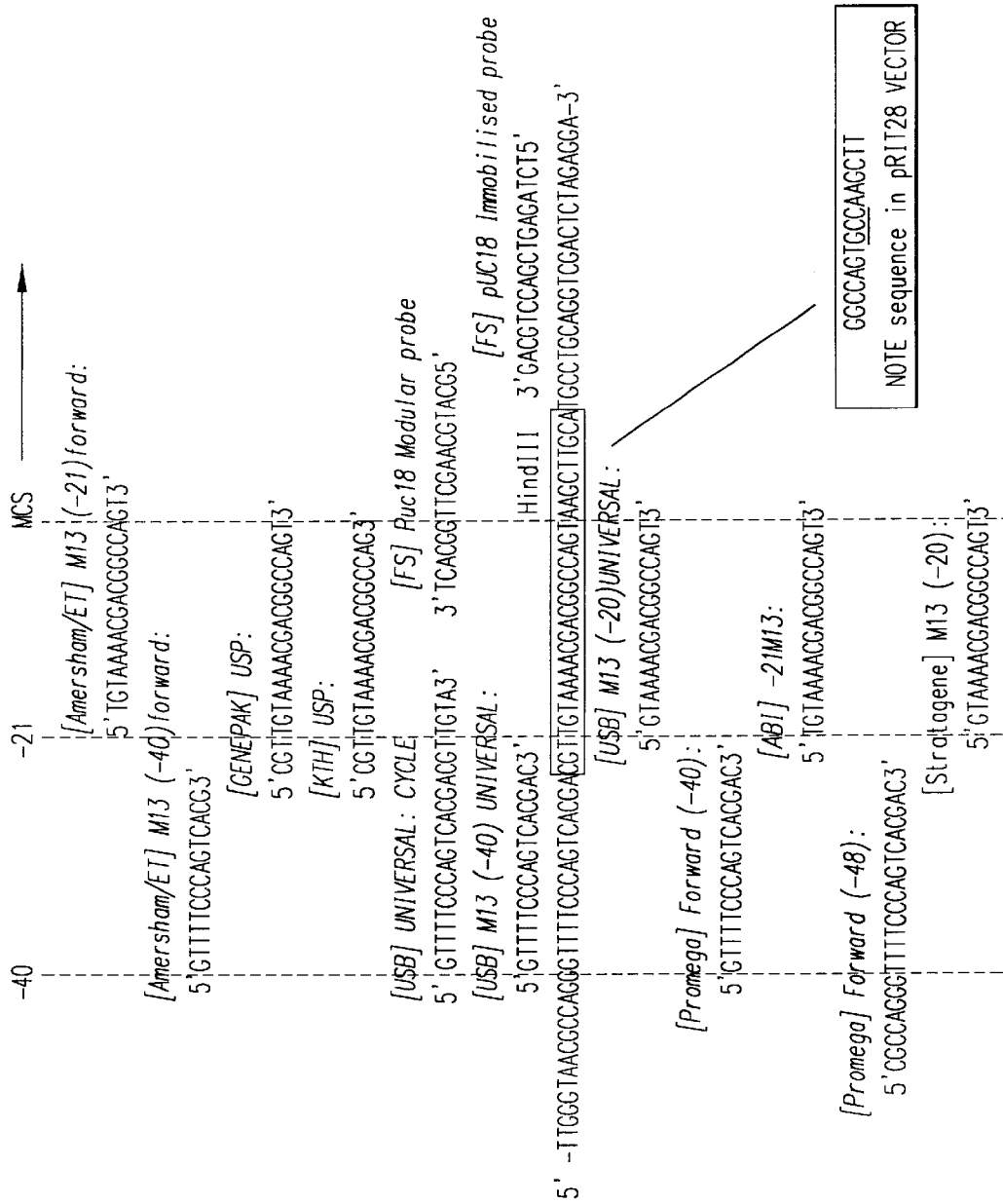

In general, modular oligonucleotides for use in the isolation of primer extension products have the features as described previously (preferably containing two modules which bind directly adjacently on the target nucleic acid in which modules are between 9 and 18 nucleotides in length) and which are complementary to and capable of binding to the vector-derived sequences of the primer extension products. Particular examples of modular oligonucleotides appropriate for use in the specific or generic approaches described above are listed in Table 1 and comprise preferred features of the invention. For reference, FIG. 1 illustrates the binding site of modular oligonucleotides according to the invention for the vector pUC18 in which the primer extension products containing portions of the vector are generated in the forward direction. The boxed region shows the area of the vector to which the generic approach modular oligonucleotide is directed. In bold, the sequence of a specific approach modular oligonucleotide is given. Suitable primers for the production of primer extension products, such as sequencing products from this vector are indicated.

As used herein, the multiple cloning site of a particular vector refers to those regions known in the art which are present in vectors for insertion of nucleic acid fragments.

It has been found that using the approach described above, ie. using modular oligonucleotides directed to vector-derived sequences, not only is efficient capture of the sequencing products achieved, but also the specificity of the reaction provides improved accuracy in the sequencing reaction (as described in the Examples herein). The results which have been achieved surpass expectation and the capture appears to be achieved without significant non-specific binding. Thus, not only is the method particularly suited to capture of sequencing products for separation, but as a result of the specificity may be used to select whole populations of sequencing products (for a particular insert) from a complex mixture. As illustrated in the examples, different sequencing product populations may be isolated either when these products have been mixed after separate sequencing extension reactions or when different sequencing extension reactions are performed simultaneously.

This has great advantages in situations in which multiplex sequencing is performed since the same primer may be used for the generation of the different sequencing products but the different populations may be selected using modular oligonucleotides direction to unique sequence features of the sequencing product populations (ie. the vector-derived sequences which are different when different vectors are used). This overcomes the disadvantage of using different primers (which may have different efficiencies) and then removing sequences on the basis of the different properties of the primer which has been used.

The above described method of the invention has been optimized and it has been found that optimally hybridization of the capture probe is performed at around 54° C., for example between 40 and 60° C., especially preferably between 50 and 58° C. This was a surprising finding since this value is close to the Tm of the capture probe in the system which was used. It was also found that optimally capture should be performed for at least 15 minutes, for example for 15 to 90 minutes. Furthermore, the amount of the modulating modules and was found to affect the capture efficiency with an optimum of at least 30 pmole of the modulating module per 150 μg of beads. Thus for example 20 to 50 pmoles should be used, for example 30–40 pmoles. It will however be appreciated that these values may vary for different systems. Appropriate optimization is well within the scope of the skilled addressee.

It has been found that when the above methods uses beads as the solid support that the beads may be used repeatedly. This thus offers a technique which is readily susceptible to automation. It has also been found that all modules of the modular oligonucleotide are preferably used simultaneously. Thus the present invention provides a one-step method appropriate for use in whole-genome sequencing projects since it offers (i) specific purification of individual sequencing reactions from a multiplex sequencing pool achieved by capture at elevated temperatures and use of modular oligonucleotides, (ii) multiple cycles of re-using the capture beads and (iii) a simple elution protocol using heat and a low salt buffer.

Methods performed in accordance with the preferred features given above are thus preferred. Thus, for example, in a preferred embodiment, the present invention provides a method of isolating primer extension products produced from a template vector, said products containing sequences corresponding or complementary to i) a primer binding region, ii) an insert and iii) vector-derived sequence(s), wherein said method comprises at least the step or steps of binding a modular oligonucleotide of at least two parts (modules) to adjacent stretches on said primer extension products, wherein said modular oligonucleotide is complementary to and capable of binding to said vector-derived sequence, and said vector-derived sequence(s) of said primer extension products is derived from any region of a particular vector, and contains a portion which remains intact after cloning of the insert, regardless of the restriction site of the multiple cloning site of a particular vector into which the insert is cloned, and to which the modular oligonucleotide anneals, wherein at least one module (capture module) is immobilized or has means for immobilization, wherein said binding is performed at between 40 and 60° C. for between 15 to 90 minutes.

Preferably the above method comprises the steps of:
1) contacting the sample containing the primer extension products with all modules of the modular oligonucleotide, wherein the capture module is immobilized on a solid support;
2) binding said modules by hybridization;
3) separating target primer extension products bound to said solid support;
4) washing said solid support.

The present invention additionally extends to a method of determining the nucleotide sequence of a nucleic acid insert in a vector wherein sequencing products are generated by methods known in the art by performing appropriate extension reactions on said vector, the sequencing products are isolated by the methods described above and the products thus isolated are separated by an appropriate technique, e.g. gel electrophoresis, gas chromatography or HPLC and the labels carried on said sequencing products are visualized to allow determination of the sequence of said insert or a portion thereof.

In a further aspect, the invention also provides the modular oligonucleotides as described herein and their use in methods of the invention.

The present invention also extends to kits for performing the methods of the invention, comprising at least the following:

modular oligonucleotides having two or more parts, suitable for use in methods of the invention.

Preferably, at least one of the modules is immobilized on a solid support or has means for immobilization. At least one of the modules may be labelled to allow detection of the target nucleic acid. Additionally, appropriate buffers and/or a solid support may be provided.

Figure 2:
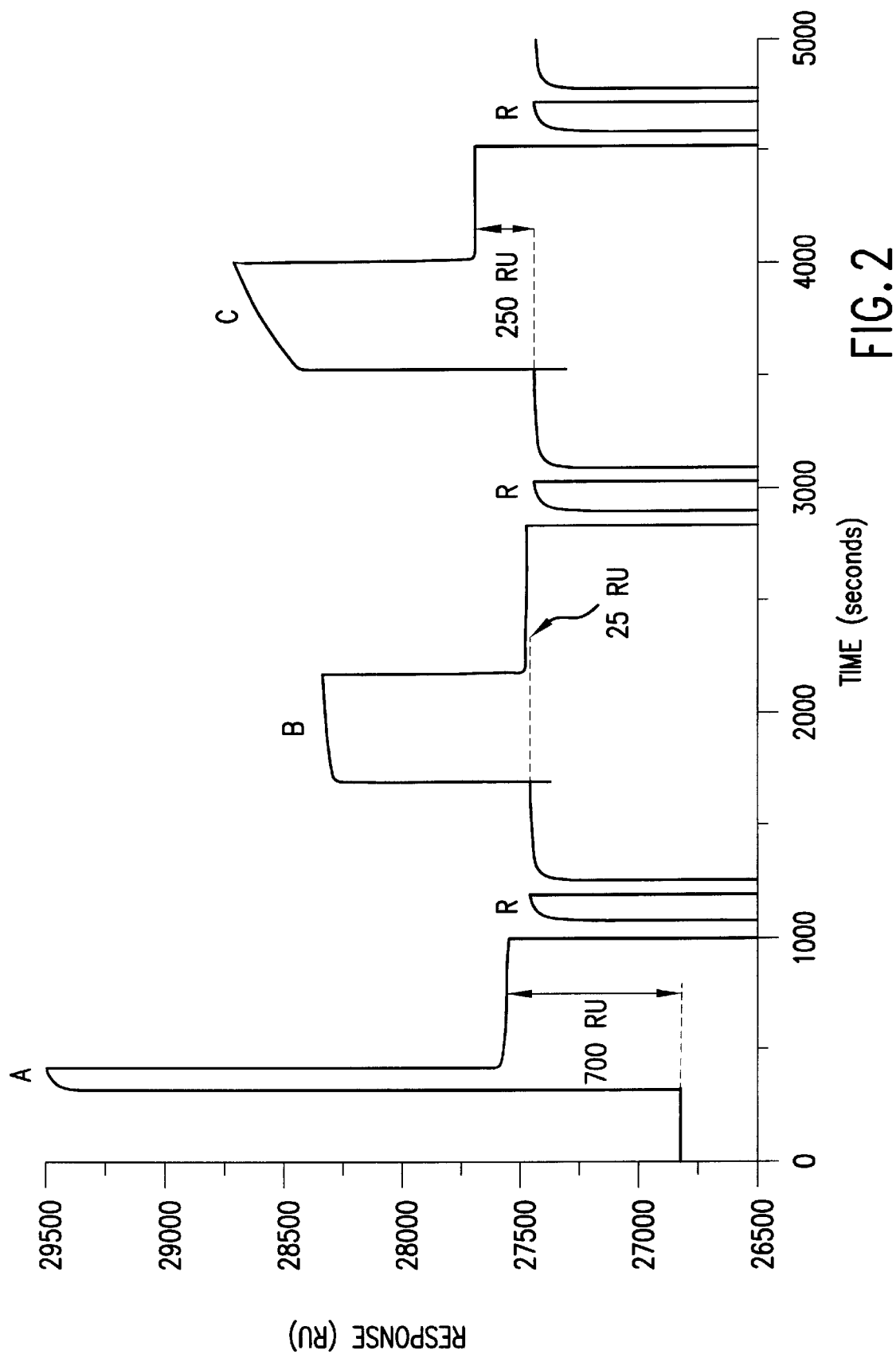
FIG. 2 illustrates a typical sensorgram showing the injection of the biotinylated C1.
Figure 3A:
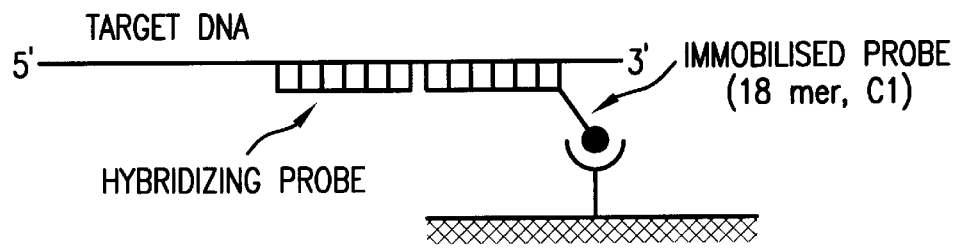
FIG. 3A is a schematic representation of viral capture with an oligonucleotide module injected over an immobilized 18-mer capture oligonucleotide.
Figure 3B:
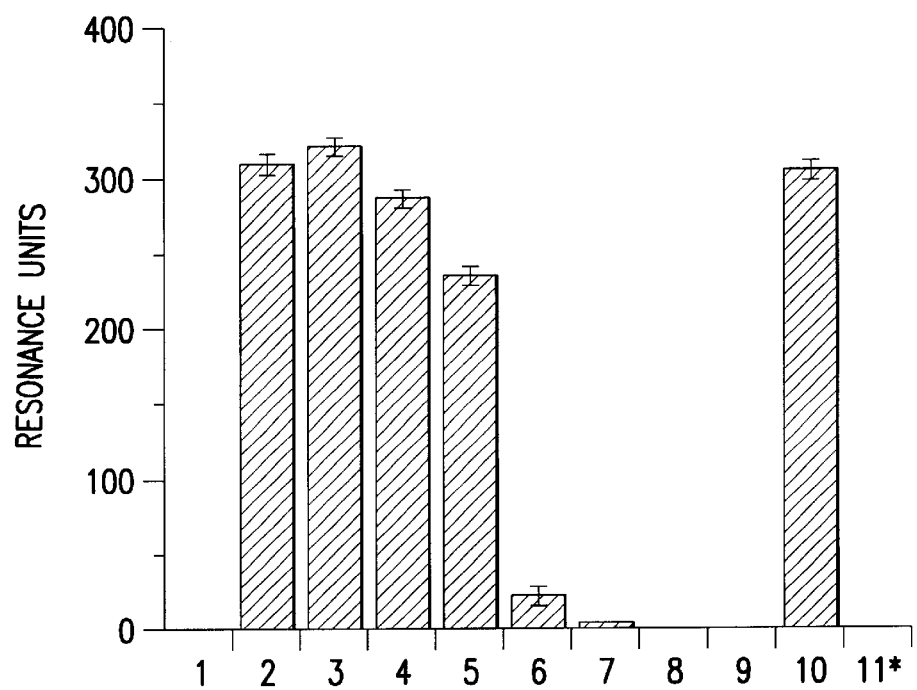
FIG. 3B shows the results of capture using the 18-mer capture oligonucleotide.
Figure 4A:
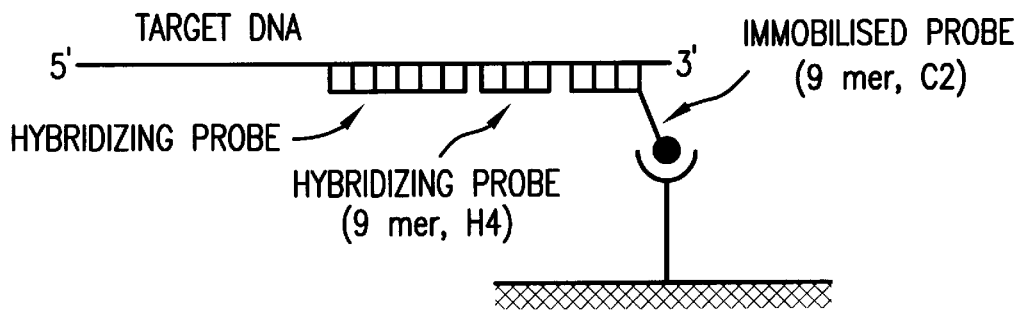
FIG. 4A is a schematic representation of viral capture with 2 oligonucleotide modules of the modular probe (9 mer and 18-mer) injected over an immobilized 9 mer capture oligonucleotide.
Figure 4B:
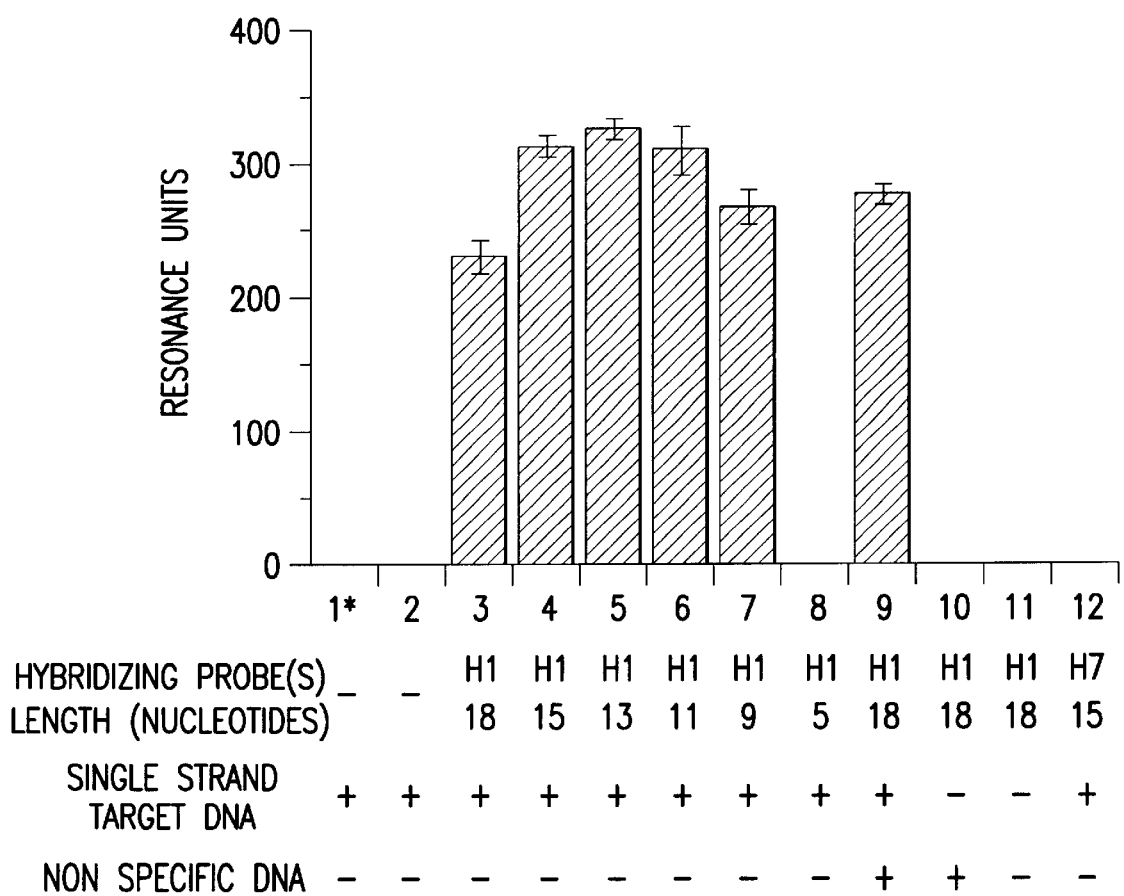
FIG. 4B is a graph showing the results of capture using the 9-mer capture oligonucleotide.
Figure 5A:
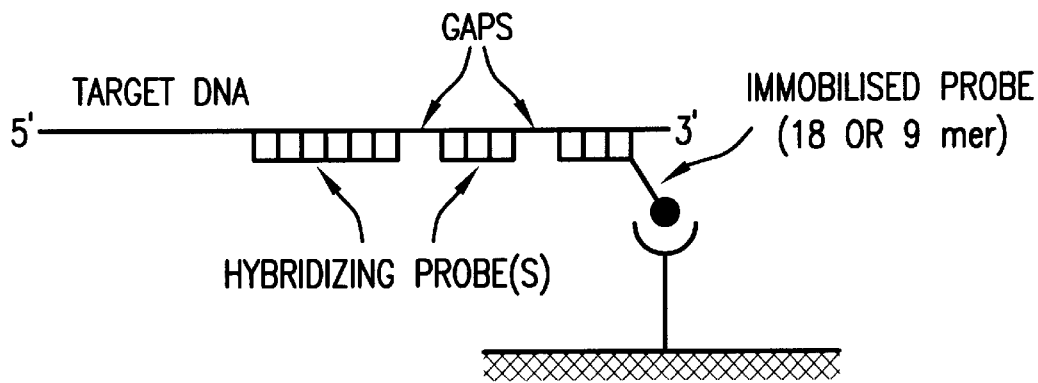
FIG. 5A is a schematic representation of viral capture as in FIG. 4A except for the presence of a 1 nucleotide space between the capture oligonucleotide and the first adjacent oligonucleotide of the modular probe or between the two non-capture oligonucleotide modules of the modular probe.
Figure 5B:
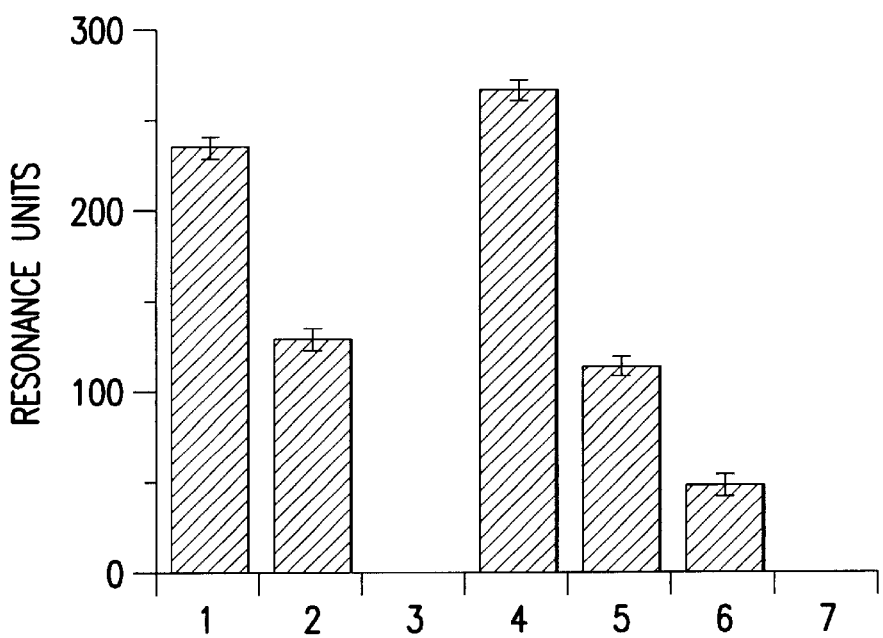
FIG. 5B is a graph showing the results of capture using a modular probe with gaps between the modules.
Figure 6A:
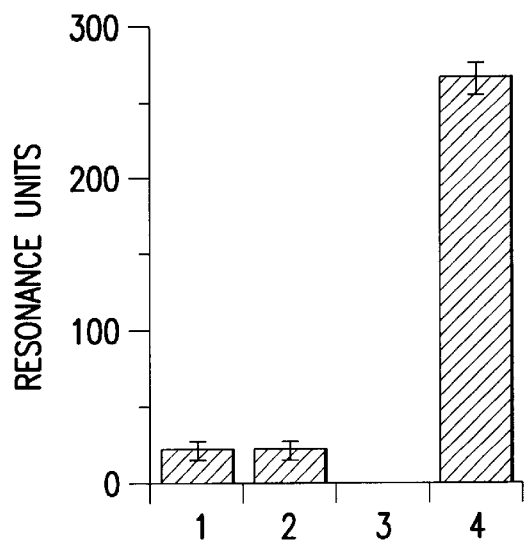
FIG. 6A is a graph showing the results of capture using modules of varying lengths.
Figure 7A:
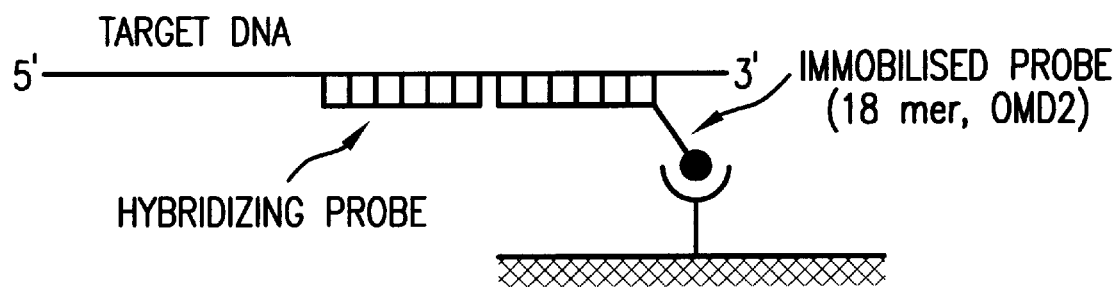
FIG. 7A is a schematic representation of viral capture in location 2 of the HCV genome using an 18-mer biotinylated capture oligonucleotide.
Figure 7B:
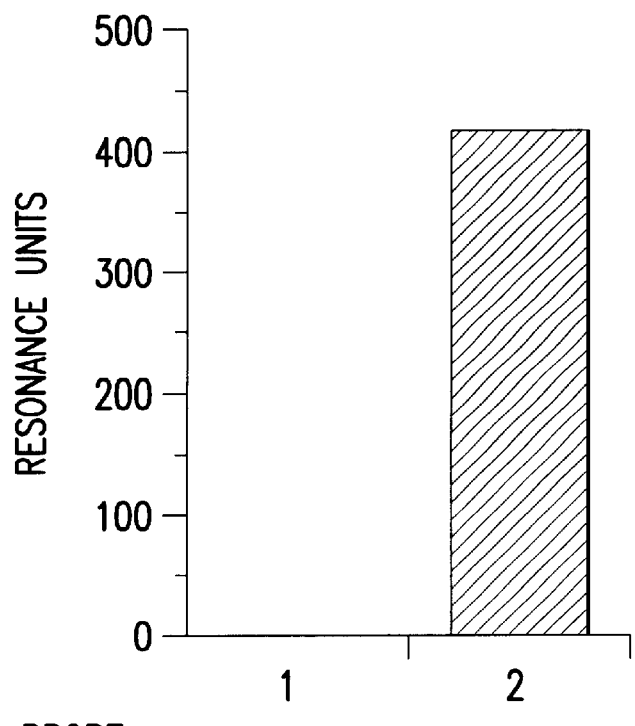
FIG. 7B is a graph showing the results of capture using the 18-mer capture oligonucleotide.
Figure 8:
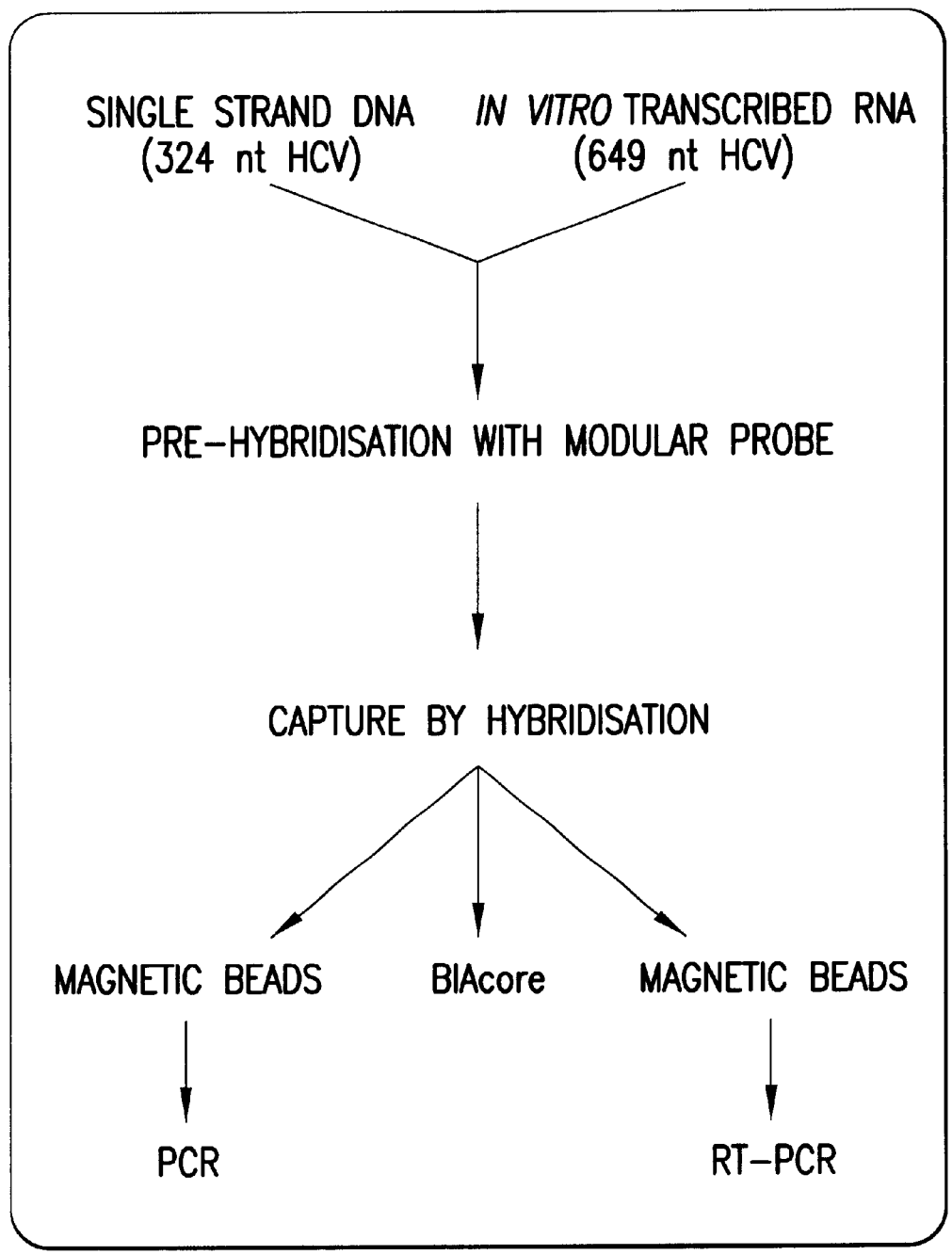
FIG. 8 is a schematic representation of the use of modular oligonucleotides to capture HCV DNA or RNA.
Figure 9:
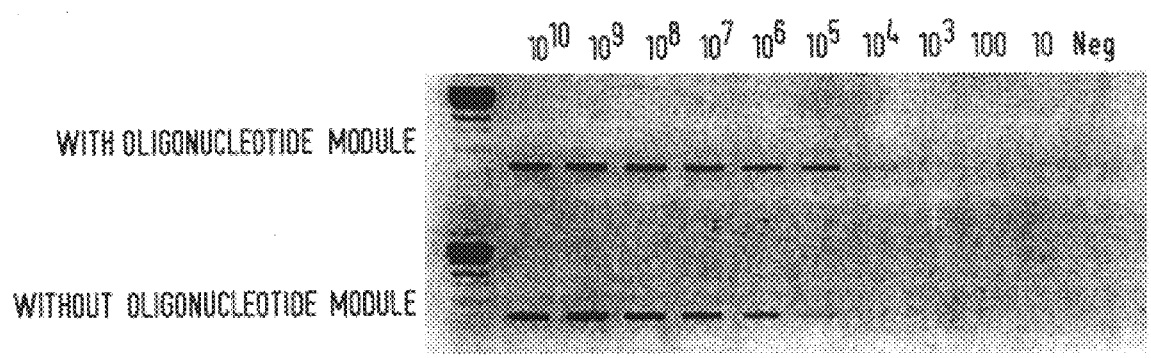
FIG. 9 shows the results of capture of HCV DNA onto magnetic beads in the absence or presence of an oligonucleotide module.
Figure 10:
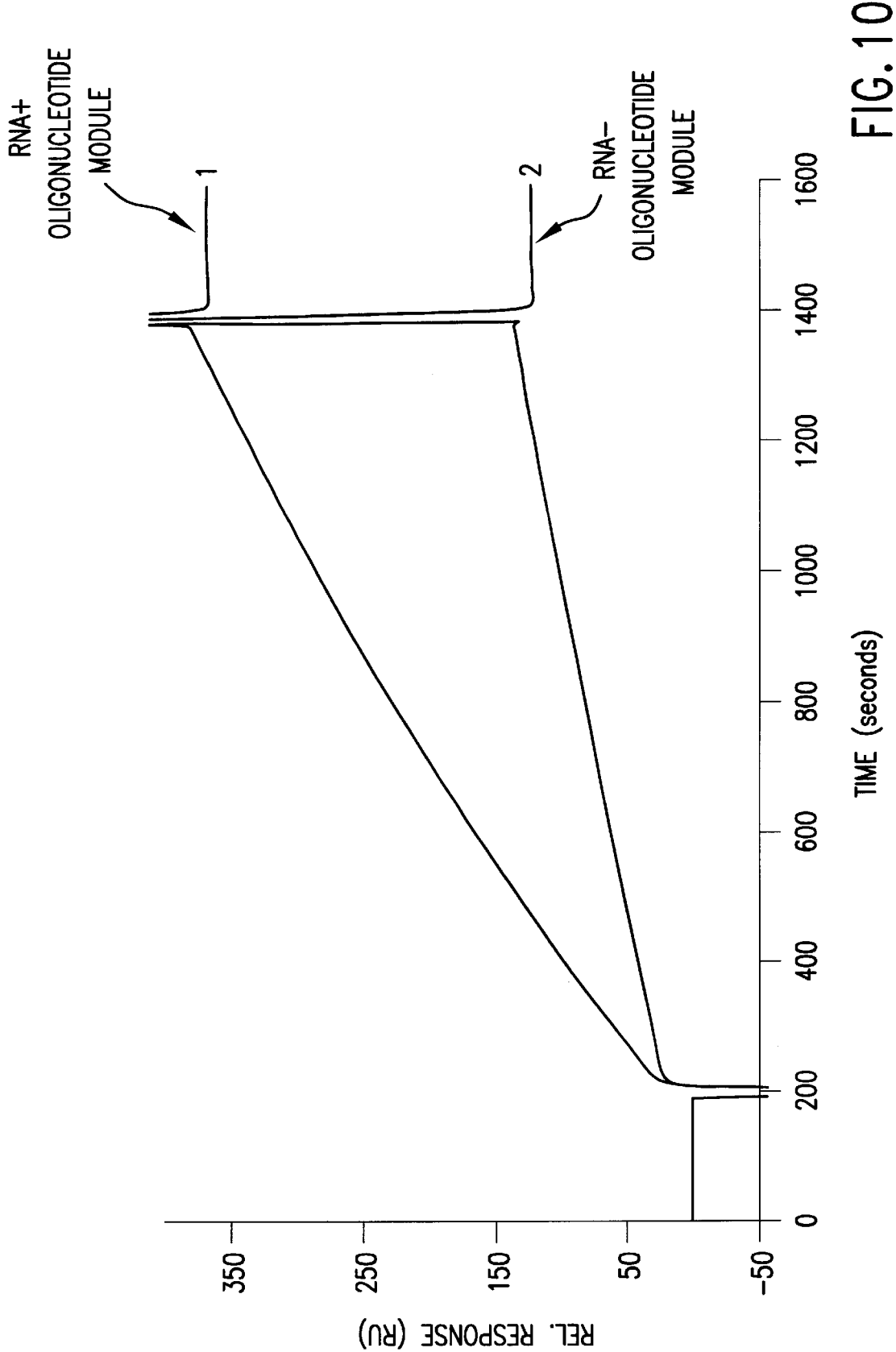
FIG. 10 is a graph providing BIAcore analysis results of capture of HCV RNA onto the chip surface in the absence or presence of an oligonucleotide module.
Figure 11:
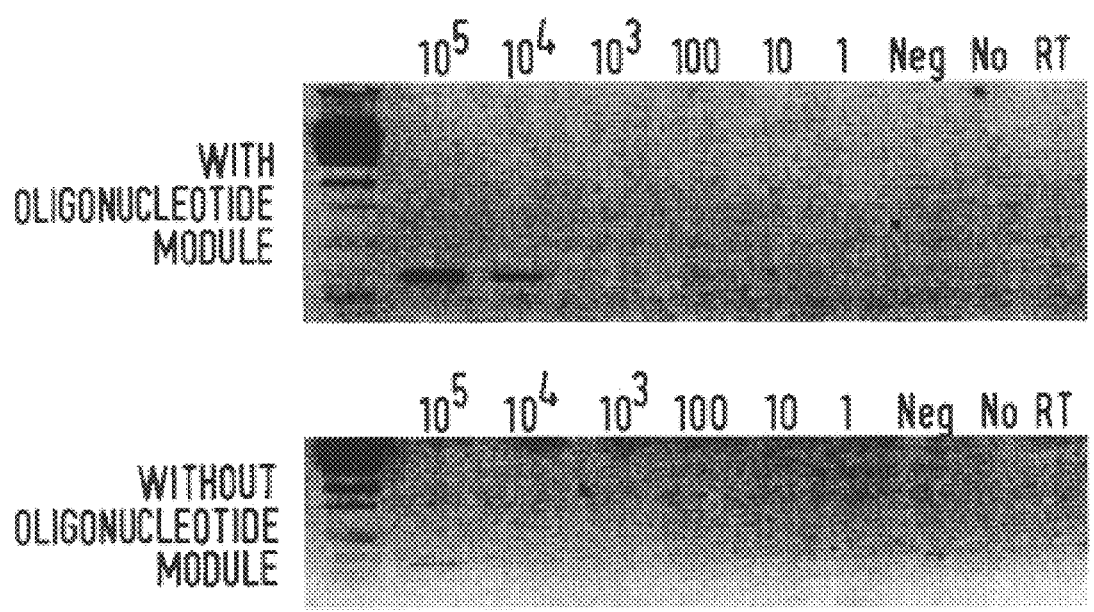
FIG. 11 shows the results of capture of HCV RNA onto magnetic beads in the absence or presence of an oligonucleotide module after single PCR.
Figure 12:
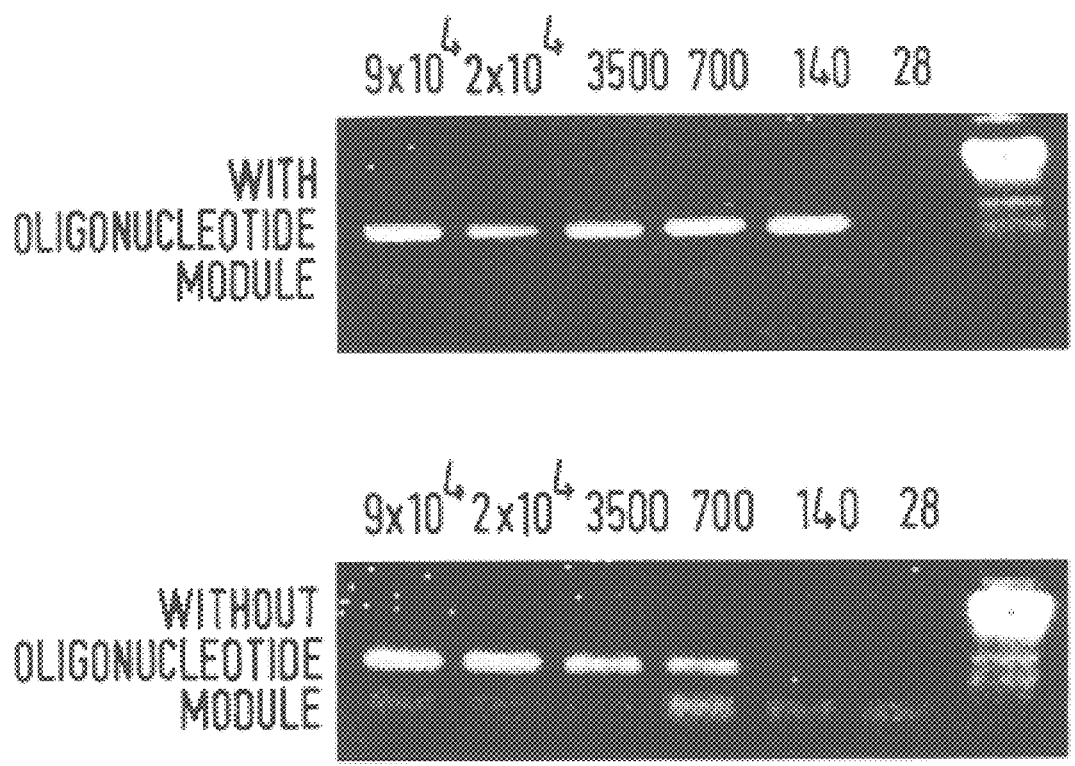
FIG. 12 shows the results of capture of HCV RNA onto magnetic beads in the absence or presence of an oligonucleotide module after nested PCR.
Figure 14:
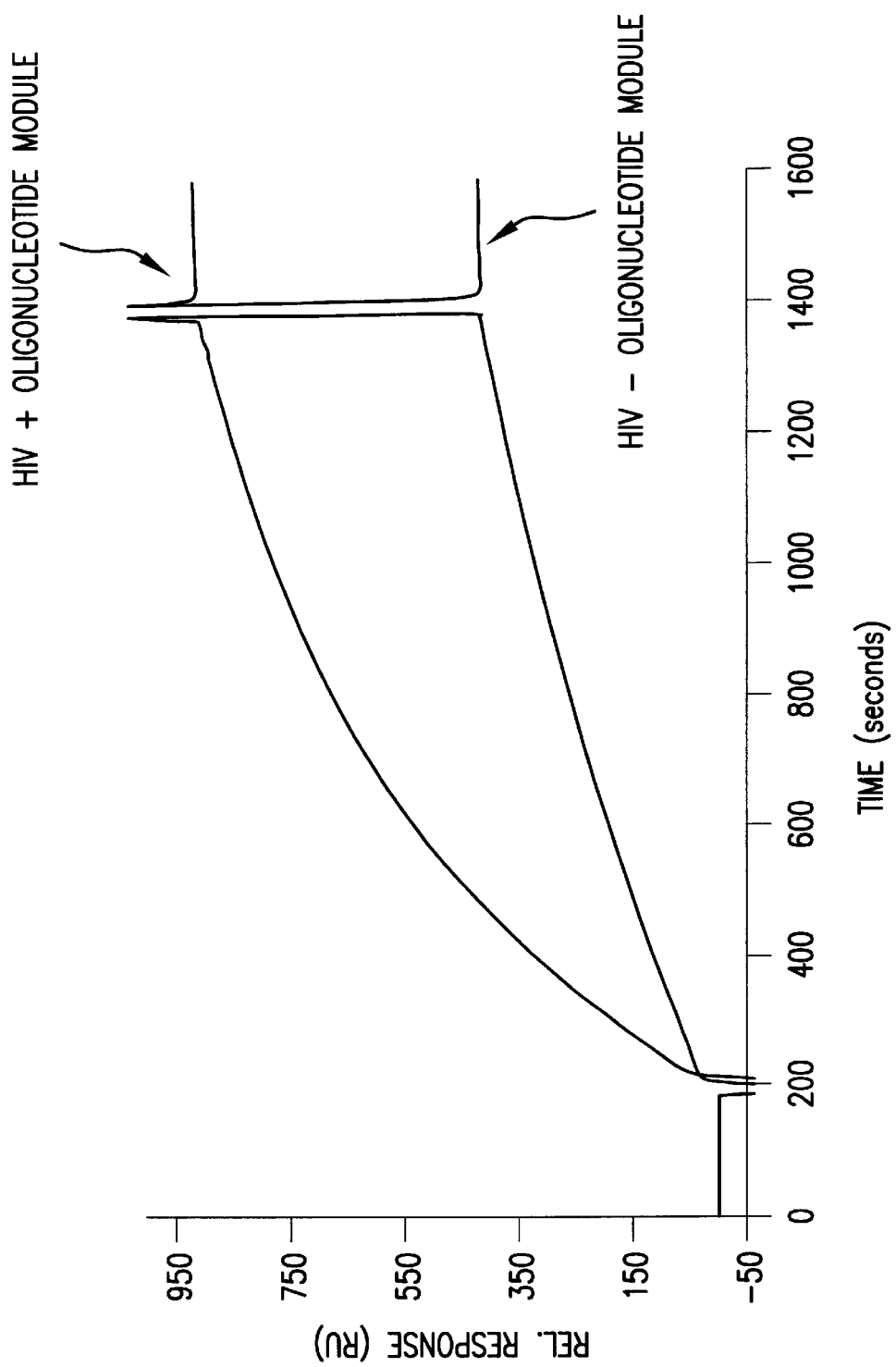
FIG. 14 is a graph providing BIAcore analysis results of capture of ss HIV-1 DNA in the absence or presence of an oligonucleotide module onto the chip surface.
Figure 15:
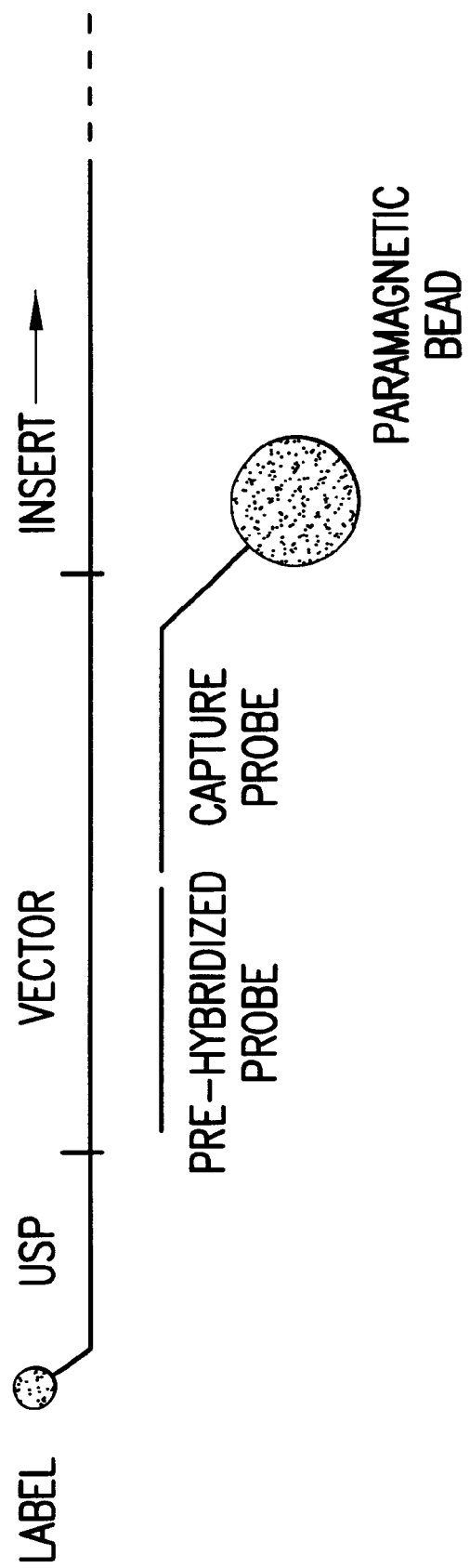
FIG. 15 is a schematic overview of the design of modular and capture probe.
Figure 16:
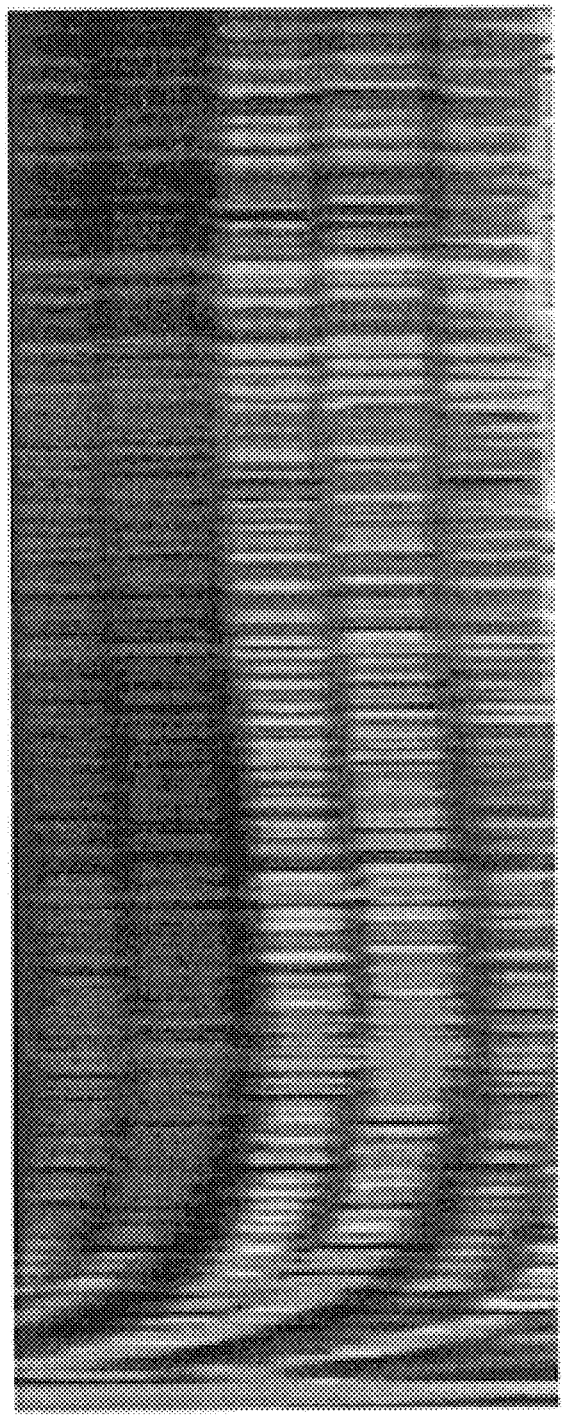
FIG. 16 shows the gelfile after gel electrophoresis using the specific modular oligonucleotides in Table 1 for use with pUC18.
Figure 20A:
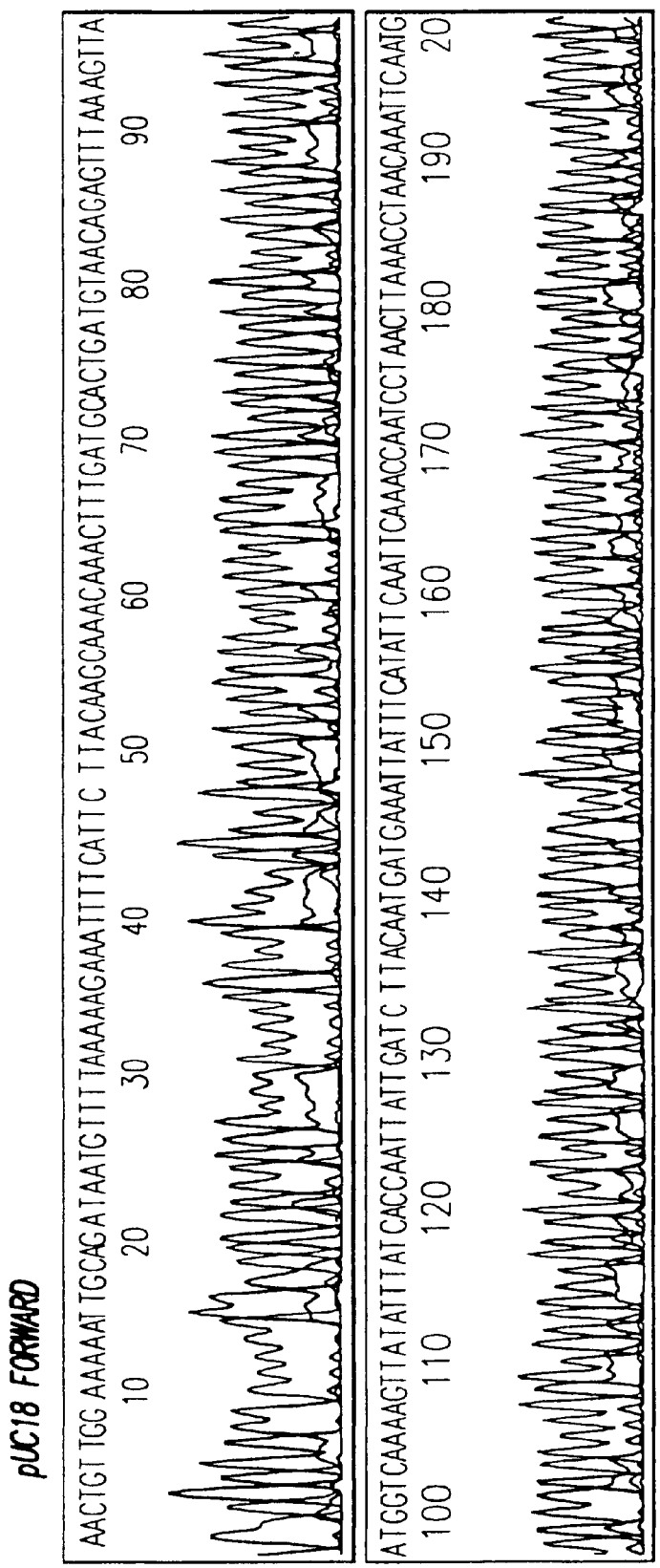
FIG. 20A, FIG. 20B and FIG. 20C provide representative and partial chromatograms showing specific capture of individual cycle sequencing reactions from a quatraplex cycle sequencing reaction (two plasmids in two directions).
Figure 20B:
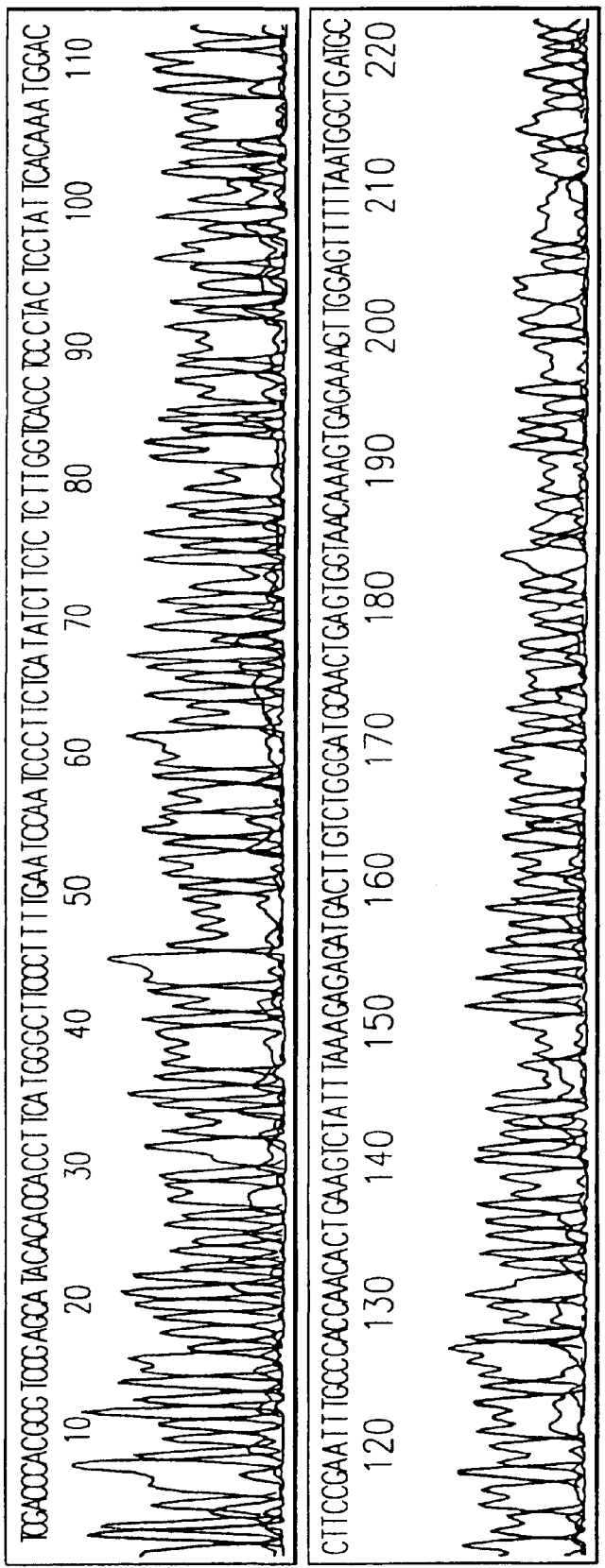
Figure 20C:
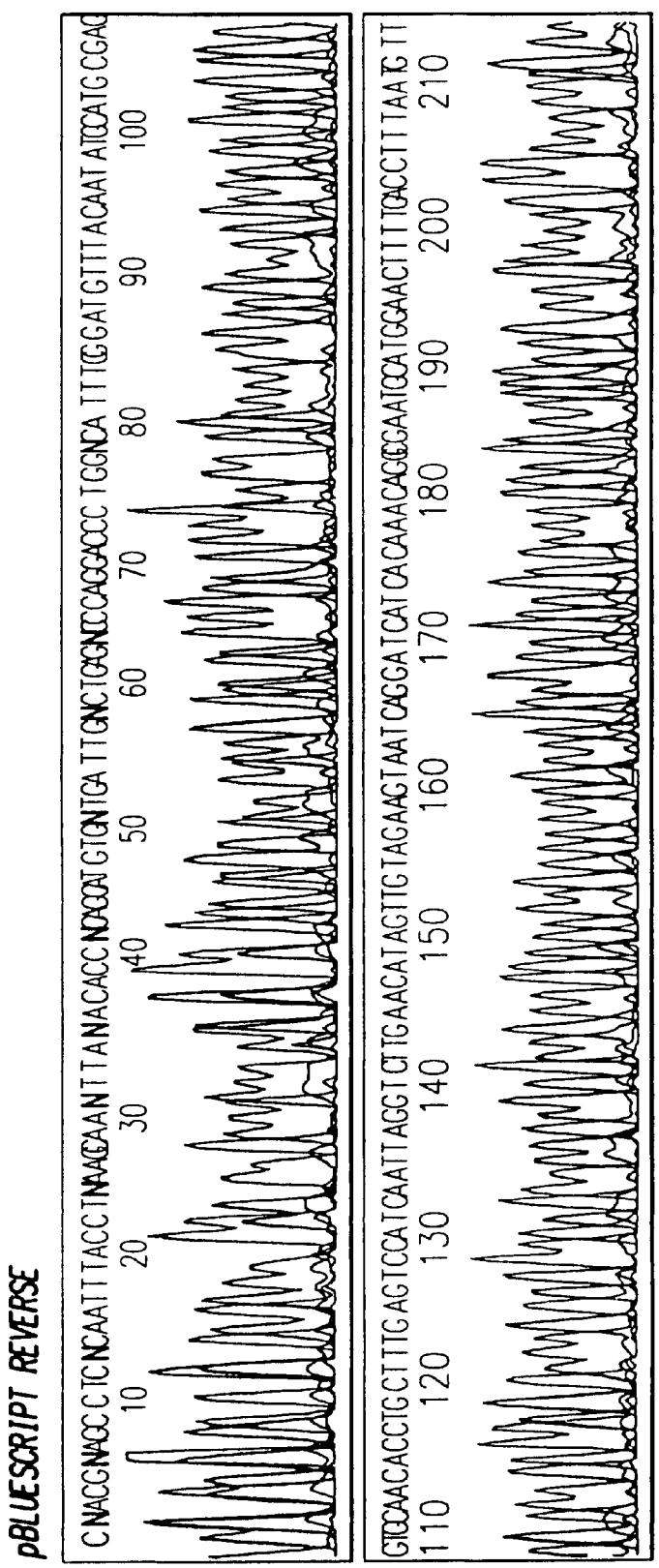

The following Examples are given by way of illustration only with reference to the following Figures in which:

FIG. 1 shows a schematic representation of modular oligonucleotides for use in isolating primer extension products generated from the vector pUC18 in the forward direction, in which the boxed region shows the area of the vector to which the generic approach modular oligonucleotide is directed, the sequences of a specific approach modular oligonucleotide is given in bold and suitable primers for the production of primer extension products are indicated;

FIG. 2 shows a typical sensorgram;

FIG. 3A shows a schematic representation of viral capture with an oligonucleotide module (=hybridising probe) (18-5 mer) injected over an immobilised 18-mer capture oligonucleotide (=immobilised probe) on the chip surface;

FIG. 3B shows the results of capture using the 18-mer capture oligonucleotide (* denotes capture data when an 18 nucleotide gap was present between the capture oligonucleotide and the oligonucleotide module—column 11);

FIG. 4A shows a schematic representation of viral capture with 2 oligonucleotide modules of the modular probe (9 mer and 18-5 mer) injected over an immobilised 9 mer capture oligonucleotide (* denotes capture data in the absence of the oligonucleotide module H4—column 1; column 12 presents capture data when an 18 nucleotide gap was present between the oligonucleotide modules);

FIG. 4B shows the results of capture using the 9-mer capture oligonucleotide;

FIG. 5A is as in FIG. 4A except for the presence of a 1 nucleotide space between the capture oligonucleotide and the first adjacent oligonucleotide of the modular probe or between the two non-capture oligonucleotide modules of the modular probe;

FIG. 5B shows the results of capture using a modular probe with gaps between the modules;

FIGS. 6A and B show the effect of different numbers of modules comprising the modular probe;

FIG. 7 shows the modular effect in location 2 of the HCV genome;

FIG. 8 shows a schematic representation of the use of modular oligonucleotides to capture HCV DNA or RNA;

FIG. 9 shows the results of capture of HCV DNA onto magnetic beads in the absence or presence of an oligonucleotide module;

FIG. 10 shows BIAcore analysis results of capture of HCV RNA onto the chip surface in the absence or presence of an oligonucleotide module;

FIG. 11 shows the results of capture of HCV RNA onto magnetic beads in the absence or presence of an oligonucleotide module after single PCR;

FIG. 12 shows the results of capture of HCV RNA onto magnetic beads in the absence or presence of an oligonucleotide module after nested PCR;

FIG. 13 shows the results of capture of HCV RNA from clinical hepatitis C samples onto magnetic beads in the absence or presence of an oligonucleotide module after single PCR; and FIG. 14 shows BIAcore analysis results of capture of ss HIV-1 DNA in the absence or presence of an oligonucleotide module onto the chip surface;

FIG. 15 shows a schematic overview of the design of modular and capture probe;

FIG. 16 shows the raw data showing the gelfile after gel electrophoresis using as modular oligonucleotides the specific modular oligonucleotide in Table 1 for use with pUC18 in the forward direction. Lane 1–2: capture without modulating module, Lane 3–4 capture with modulating module, Lane 5 ethanol precipitated material;

FIG. 17 shows results of optimisations of the modular capture using as modular oligonucleotides the specific modular oligonucleotide in Table 1 for use with pUC18 in the forward direction. (A) titration of the amount of beads (B) titration of the amount of modulating module, (C) titration of the temperature, (D) titration of the incubation time at 54° C., (E) titration of the incubation time at room temperature;

FIG. 18 shows re-use of beads (A) elution with formamide (B) elution with heat and water;

FIG. 19 shows specificity and background of the modular capture from multiple cycle sequencing reactions, tested with two bead types, namely A) the specific modular oligonucleotide in Table 1 for use with pUC18 in the forward direction and B) the specific modular oligonucleotide in Table 1 for use with pBluescript in the forward direction; and FIG. 20 shows representative and partial chromatograms showing specific capture of individual cycle sequencing reactions from a quatraplex cycle sequencing reaction (two plasmids in two directions, using A) the specific modular oligonucleotide in Table 1 for use with pUC18 in the forward direction, B) the specific modular oligonucleotide in Table 1 for use with pBluescript in the forward direction and C) the generic modular oligonucleotide in Table 1 for use with pBluescript in the reverse direction).

EXAMPLE 1

Capture of ssDNA Using a Capture Oligonucleotide and at Least One Additional Oligonucleotide as the Modular Probe This example illustrates the manyfold increase in the capture of ssDNA by an immobilised capture oligonucleotide when specific oligonucleotide modules have been previously hybridised to the DNA. The capture oligonucleotide (referred to in this example as capture oligonucleotide or immobilized oligonucleotide) and oligonucleotide hybridized to the DNA (referred to in this example as oligonucleotide modules) together are the modules of the modular probe.

Figure 6B:
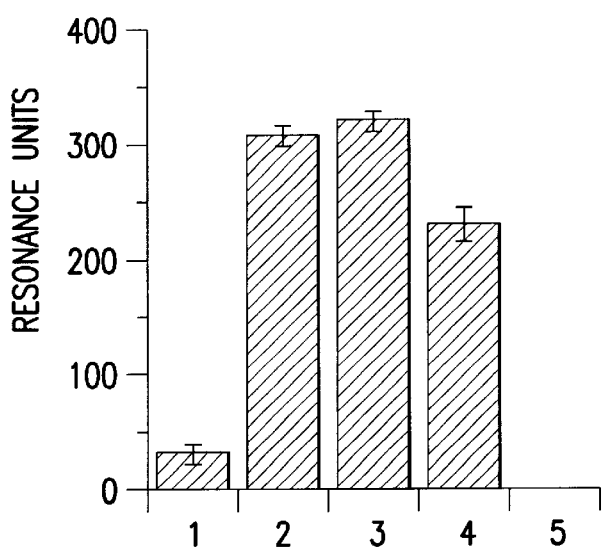
FIG. 6B is a graph showing the results of capture using modules of varying lengths.

Various combinations of capturing oligonucleotides and oligonucleotide modules for binding to the DNA were used. Thus, 18 mer capture oligonucleotides were used in conjunction with either an 18, 15, 13, 11, 9 or 5 mer oligonucleotide module (FIG. 3B), 9 mer capturing oligonucleotides with a 9 mer oligonucleotide module with and without a second oligonucleotide module (18, 15, 13, 11, 9 or 5 mer) (FIG. 4B). Also modular probes with a 1 nucleotide space between the annealing sites of the modules were tested (FIGS. 5B and 6A). To further investigate the modular effect a 36 mer biotinylated oligonucleotide (comprising of the 18 mer capture oligonucleotide C1 and the 18 mer oligonucleotide module H1-18) was designed and tested for its efficiency in capturing HCV (FIG. 6B).

MATERIALS AND METHODS
PCR Amplification (Template Generation)

Clones containing the 5' non-translated region (NTR) of two hepatitis C virus (HCV) genotypes (2b and 3a) in the pGEM®-T vectors (Promega, Madison, Wis., USA), were used as a template in the PCR to generate a 324 bp fragment for biosensor analysis. PCR amplification was performed with 0.2 µM of each primer OU49 and OD66;

OU49 5'-GGCGACACTCCACCATGAATC-3' (SEQ ID NO.18)

OD66 5'-biotin-GGTGCACGGTCTACGAGACC-3' (SEQ ID NO.19)

Amplification was performed in a 50 µl reaction volume containing 10 mM Tris-HCl (pH 8.3), 50 mM KCl, 2 mM $MgCl_2$, 0.1% Tween® 20, 0.2 mM dNTP's and 0.5 U of AmpliTaq® DNA polymerase (Perkin-Elmer, Foster City, Calif.), using a Perkin-Elmer 9600 thermocycler (Perkin-Elmer, Norwalk, Conn.). The temperature profile was 94° C. for 5 minutes, followed by 30 cycles of (94° C. for 15 seconds, 62° C. for 45 seconds, 72° C. for 60 seconds) and ending with 72° C. for 10 minutes.

Single Strand Preparation

The biotinylated PCR-products were immobilised onto streptavidin-coated paramagnetic beads (Dynabeads® M-280 Streptavidin; Dynal, Oslo, Norway) and by strand-specific elution a pure template for hybridisation was obtained (Hultman et al., 1989, Nucl. Acids Res., 17, p 4937–4946). Fifty microliters of PCR-product was captured by incubation for 15 minutes at room temperature with 5 mg/ml of beads in 50 µl binding/washing buffer (10 mM Tris-HCl (pH 7.5) 1 mM EDTA, 2 M NaCl, 1 mM β-mercaptoethanol, 0.1% Tween® 20). After washing and removal of supernatant, the strands were separated by incubation with 10 μl of 0.1 M NaOH for 5 minutes. The alkaline supernatant with the non-biotinylated strand was neutralised with 6 μl of 0.1667 mM HCl and 1 μl of 280 mM Tris-HCl, pH 7.5, 100 mM $MgCl_2$. In order to prevent any co-eluted biotinylated strands from interacting with the streptavidin on the sensor ship, a second round of sedimented streptavidin beads (250 μg) was mixed and the supernatant collected. In order to reduce the differences between individual samples within an experiment the eluted single strand DNA was batched. The prepared single stranded DNA was then qualitatively and quantitatively analysed on 10–15% PAGE with PhastSystem™ and PhastGel® DNA Buffer Strips and DNA Silver Staining Kit (Pharmacia Biotech, Uppsala, Sweden).

Oligonucleotides

Biotinylated oligonucleotides for immobilisation onto the sensor chip and oligonucleotides for hybridisation to the ss HCV PCR product were purchased from KEBO, Stockholm, Sweden. The oligonucleotide sequences are shown in Table 2 for location 1 and Table 3 for location 2.

Biosensor Analysis

A BIAcore® 2000 instrument (Pharmacia Biosensor, Uppsala, Sweden) was used in all experiments. Sensor chips SA (Pharmacia Biosensor), precoated with approximately 4000 RU streptavidin (1000 RU corresponds to approximately 1 $ng/mm^2$ of streptavidin), were used. Experiments were performed at 25° C. with 6×SSPE (0.9M NaCl (pH 7.4), 60 mM $NaH_2PO_4$, 7.5 mM EDTA and 0.005% (v/v) Surfactant P20 (Pharmacia Biosensor) as injection and running buffer. The biotinylated oligonucleotides for capture onto the sensor chip were immobilised to a level of approximately 500–1000 RU (1000 RU corresponds to approximately 1 $ng/mm^2$ (Stenberg et al., 1991, J. Colloid Interface Sci., 143, p 513–526) by injection of 50 μl 6×SSPE containing 1 μM biotinylated oligonucleotide at a flow of 30 μl/minute. Before and after use in hybridisation experiments the sensor chips were treated with three pulses of 50 mM NaOH (5 μl, 5 μl/min) to regenerate (R) the surface. One flow cell, without immobilized oligonucleotide was used as reference.

Hybridisation and Single Strand Capture

Oligonucleotide modules were hybridised to the ss target DNA by incubation in a hybridisation oven for 45 minutes at 54° C. with constant rotation then cooled to room temperature. Hybridisation was performed in 100 μl 6×SSPE containing approximately 200 nM ssDNA and 500 nM oligonucleotides.

Forty μl of the hybridisation mix was injected over the immobilised capture oligonucleotide at a flow of 5 μl/min. Controls samples with no hybridizing probes were treated in exactly the same manner. The oligonucleotide surface was regenerated with 50 mM NaOH (5 μl, 5 μl/min).

RESULTS

A 324 base pair (bp) fragment of the non-translated region (NTR) of HCV was generated by PCR. The dsDNA was melted apart by magnetic bead separation to obtain ssDNA suitable for capture by oligonucleotides immobilised on a sensor chip in the biosensor. This ssDNA was hybridised to oligonucleotide modules prior to injection over the sensor chip which results in a highly efficient capture of the HCV DNA.

In this example biosensor technology was used which allows biological events to be monitored in real time (Jönsson et al., 1991, BioTechniques, 11, 620–672). This method utilises a sensor chip as a solid support for immobilisation. Detection is based on surface plasmon resonance (SPR) to monitor changes in refractive index over time at the sensor surface. The changes are proportional to the mass of molecules bound on the surface and are shown in a so-called sensorgram as resonance units (RU) over time. A representative sensogram is depicted in FIG. 2 which shows the injection (A) of the biotinylated C1 (18 mer capture oligonucleotide). The immobilisation is rapid and the amount of bound oligonucleotide is determined to be 700 RU by comparing the response units before and after the injection pulse. After regeneration (R) of the sensor surface with 50 mM NaOH, the immobilised capture oligonucleotide was used for capturing the single strand DNA target by hybridisation. As shown in FIG. 2 (B) when only single strand target DNA is injected over the sensor chip only negligible amounts are hybridised (<20 RU). In contrast, when the single strand target with a preannealed oligonucleotide module H1 (18 mer), designed to be adjacent to the capture oligonucleotide, was passed over the sensor chip (C), significant amounts were retained (250 RU).

Investigation of the Modular Effect Using an 18 Mer Oligonucleotide as Capture Probe in Location 1.

An 18 mer biotinylated capture oligonucleotide (C1) was immobilised on a Streptavidin sensor chip. Single stranded HCV DNA with and without previously hybridised oligonucleotide modules was injected over the sensor chip as described in the methods section. The experimental protocol is illustrated schematically in FIG. 3A and the results are shown in FIG. 3B. The results represent normalised values from independent experiments as a consequence of the variation of absolute responses between different sensor chips, depending on the amount of streptavidin coated onto the chip surface, thus affecting the amount of immobilised capture oligonucleotide and capture efficiency. The low capture efficiency with ss DNA injected over an 18 mer immobilised capture oligonucleotide (C1) is displayed in FIG. 3B, column 1. A similar low capture was also achieved even if a 5' spacer of 10 adenines was used with the 18 mer (C1×10A, Table 2) (data not shown). In the subsequent capture experiments a prehybridised complex comprising of ss target DNA and oligonucleotide modules was used. The oligonucleotide modules varied from 18 to 5 nucleotides in length, but all were designed to anneal adjacent to the 3'-end of the immobilised capture oligonucleotide (Table 2). Using the specific oligonucleotide modules (H1-18, 15, 13, 11; 18 to 11 mers) a significant increase of capture (230 to 320 RUs) was observed (FIG. 3B, columns 2–5), as compared with the experiment lacking an oligonucleotide module (column 1). However, the capture efficiency was greatly diminished and sometimes abolished when H1 was less than 9 nucleotides in length (FIG. 3B, column 6 and 7). The different controls clearly indicate the specificity on hybridisation between the immobilised capture oligonucleotide and the single strand DNA/oligonucleotide module complex as the responses arising from interactions of oligonucleotides or nonspecific DNA were negligible (FIG. 3B, columns 8 to 11). Column 11 shows that no capture occurs when an 18 nucleotide gap is present between the different modules.

Investigation of the Modular Effect Using a 9 Mer Oligonucleotide as Capture Probe.

A 9 mer biotinylated capture oligonucleotide (C2) was immobilised on a SA sensor chip and the oligonucleotide modules fractionated into smaller modules. The experimental protocol is illustrated schematically in FIG. 4A and the results are shown in FIG. 4B. As expected no capture of DNA was observed when an immobilised capture nonamer (C2) was used alone (FIG. 4B, column 1). When the nonamer oligonucleotide module (H4) and the oligonucleotide module (H1-18, 15, 13, 11, 9) were used, ss DNA was successfully captured (FIG. 4B, columns 3–7). However as in FIG. 3H, module assisted capture with the short pentamer module (H1-5) was unsuccessful (column 8) as well as use of a single nonamer oligonucleotide module (H4) column 2). These results together with data from FIGS. 6A and 6B, suggest that it is not the length of the capture oligonucleotide that is the most important parameter, rather it depends on the number and length of oligonucleotide modules that are employed. Control experiments were carried out both for the 18 and 9 mer immobilised capture oligonucleotides to verify the concept. Firstly, non-specific interactions were investigated by injecting a similar sized non-specific DNA over the capture oligonucleotide (FIG. 3B, column 8, and FIG. 4B, column 10) and by injecting the oligonucleotide module along (FIG. 3B, column 9 and FIG. 4B, column 11). No increase in response was observed. Secondly, non-specific DNA was co-incubated with the target DNA and the oligonucleotide module. Capture was still specific and no interference from the non-specific DNA was observed (FIG. 3B, column 10; FIG. 4B, column 9. Hence the modular approach has the ability to capture a specific target without any reduction in signal when challenged with unrelated DNA. Column 12 indicates that no capture occurs when an 18 nucleotide gap is present between the non-capture oligonucleotide modules.

The Effect of Gaps Between Oligonucleotide Modules

From the previous experiments the detrimental effects on capture efficiency with 18 nucleotide long gaps between oligonucleotide modules was clear (FIG. 4B, column 12) and/or immobilised capture probe (FIG. 3B, column 11). To further analyse the restrictions in the oligonucleotide module assisted capture approach, single nucleotide gaps were introduced between the modules of the modular probe. The H1-11 mer capture oligonucleotide and the two nonamer oligonucleotide modules (H4 and H1-9) were reconstructed and their annealing sites shifted one nucleotide towards the 5' end of the target DNA and were renamed H2, H5 and H3 respectively (Table 2). Comparison showed that discontinuous probes were able to capture single strand target, although at a lower efficiency (FIGS. 5A, B).

Fragmentation of Long Oligonucleotides Into Shorter Modules

This experiment was performed to further investigate whether the efficiency could be improved by fragmentation of extended capture oligonucleotides into shorter modular units. As illustrated in FIG. 6A (columns 1, 2 and 3) when an immobilised 27 mer oligonucleotide was used for capturing or when two oligonucleotides with a total annealing length of 27 nucleotides were used, the capture of DNA was poor. However when this 27 nucleotide stretch was fragmented into three nonamers a highly efficient capture was observed (FIG. 6A, column 4). This was further substantiated by a 36 nucleotide capture oligonucleotide (C4) (Table 2) which fails to efficiently capture single strand target DNA (FIG. 6B, column 1), while use of oligonucleotide modules and a shorter immobilised capture probe significantly improves the capture (FIG. 6B, columns 2, 3 and 4).

To investigate whether this effect is observed at another position in the HCV genome (location 2), a second 18 mer capturing oligonucleotide was designed together with an 18 mer oligonucleotide module. The oligonucleotide sequences are shown in Table 3.

Investigation of the Modular Effect in Location 2 of the HCV Genome.

An 18 mer biotinylated capture oligonucleotide (OMD2) was immobilised on a SA sensor chip as described above. The results are shown in FIG. 7. Injection of ssDNA with an 18 mer oligonucleotide module (OMD6) resulted in an increase of 400 RU (column 2) while ssHCV alone was not captured (column 1).

CONCLUSIONS

This example illustrates that ssHCV is captured poorly or not at all by the 18 mer oligonucleotide immobilised on the chip (FIG. 3B, column 1, FIG. 5B, column 3 and FIG. 6B, column 5). When the ssHCV was incubated with an oligonucleotide module of 18, 15, 13 or 11 nucleotides a significant increase in capture was observed (FIG. 3B, columns 2–5). However incubation of ssHCV DNA with a 9 mer or 5 mer oligonucleotide module did not result in an increase in capture (FIG. 3B, columns 6–7). When a 36 mer capture oligonucleotide was used in place of the 18 mer capture oligonucleotide and the 18 mer oligonucleotide module little capture of HCV was observed (FIG. 6B, column 1). These results further substantiate the modular effect. Non-specific hybridisation of the HCV DNA was investigated by injecting a similar sized non-HSV ss PCR product (treated in the same manner) over the capture oligonucleotide (FIG. 3B, column 8). Non-specific hybridisation of the oligonucleotide modules was investigated and was also ruled out (FIG. 3B, column 9).

No capture of DNA was observed when a 9 mer immobilised capture oligonucleotide was used alone for capture (FIG. 4B, column 1) or with a single 9 mer oligonucleotide module (FIG. 4B, column 2). However, when two 9 mer oligonucleotide modules were incubated with the DNA, a highly efficient capture was observed by the immobilised 9 mer (FIG. 4B, column 7). These oligonucleotides anneal at the same position on the DNA as the 18 mer capturing oligonucleotide with the 9 mer oligonucleotide module (FIG. 3B, column 6) but hybridisation is only observed when 2 oligonucleotide modules are used as opposed to 1 oligonucleotide module.

When an 18 and a 9 nucleotide space between the second and third oligonucleotides of the modular probes was inserted the modular effect was abolished (FIG. 4B, column 12, data for the 9-nucleotide gap not shown). To further investigate the effect of inserting a space between the modules, three 9 mer oligonucleotides with a one nucleotide gap between them were designed. These one nucleotide gaps do seem to result in slightly less capture of HCV DNA but nevertheless good hybridisation signals of approximately 50 to 100 RU were obtained. (FIG. 5B, columns 5 and 6). The gap between the capturing oligonucleotide and the first oligonucleotide module (column 5) resulted in slightly more efficient capture than the gap between the second and third modules (column 6). A single gap between the modules of a modular probe with 2 modules also resulted in improved capture over the non-modular probe, but was reduced with respect to a 2-module modular probe without a gap between modules (FIG. 5B, columns 1 and 2).

The results for experiments using modular probes complimentary to location 2 further support the modular theory, as a 200 fold increase in signal was observed when the 18 mer oligonucleotide module was hybridised to the DNA prior to capture by the immobilised oligonucleotide (FIG. 7).

TABLE 2

Oligonucleotides used in the module assisted capture of target DNA-location 1

```
                 290       300       310       320       330       340
                  |         |         |         |         |         |
HCV Seq   5'-  ---TGCCTGATAGGGTGCTTGCGAGTGCCCCGGGAGGTCTCGTAGACCGTGCACC---   -3'      (SEQ ID NO.20)
                  |         |         |         |         |         |

C1        3'-                                             AGAGCATCTGGCACGTGG         -biotin-5'  (SEQ ID NO.21)
C1x10A    3'-                                             AGAGCATCTGGCACGTGG(A)10    -biotin-5'  (SEQ ID NO.22)
C2        3'-                                                     GGCACGTGG          -biotin-5'  (SEQ ID NO.23)
C3        3'-                                   GGGCCCTCCAGAGCATCTGGCACGTGG          -biotin-5'  (SEQ ID NO.24)
C4        3'-                         ACGCTCACGGGGCCCTCCAGAGCATCTGGCACGTGG          -biotin-5'  (SEQ ID NO.25)

H1-18     3'-                         ACGCTCACGGGGCCCTCC                             -5'        (SEQ ID NO.26)
H1-15     3'-                           CTCACGGGGCCCTCC                              -5'        (SEQ ID NO.27)
H1-13     3'-                            CACGGGGCCCTCC                               -5'        (SEQ ID NO.28)
H1-11     3'-                              CGGGGCCCTCC                               -5'        (SEQ ID NO.29)
H1-9      3'-                                GGGCCCTCC                               -5'        (SEQ ID NO.30)
H1-5      3'-                                    CCTCC                               -5'        (SEQ ID NO.31)
H2        3'-                              ACGGGGCCCTC                               -5'        (SEQ ID NO.32)
H3        3'-                                GGGGCCCTC                               -5'        (SEQ ID NO.33)
H4        3'-                                             AGAGCATCT                  -5'        (SEQ ID NO.34)
H5        3'-                                             CAGAGCATC                  -5'        (SEQ ID NO.35)
H6        3'-                                   GGGCCCTCCAGAGCATCT                   -5'        (SEQ ID NO.36)
H7        3'-    CGGACTATCCCACGA                                                     -5'        (SEQ ID NO.37)
H8        3'-              ACGCTCACG                                                 -5'        (SEQ ID NO.38)
```

TABLE 3

Oligonucleotides used in the module assisted capture of target DNA-location 2

```
                   132                              167
                    |                                |
HCV seq   5'- ----GGAGAGCCATAGTGGTCTGCGGAACCGGTGAGTACA---   -3'         (SEQ ID NO.39)
OMD2      3'-                    CGCCTTGGCCACTCATGT         -biotin-5'  (SEQ ID NO.40)
OMD6      3'-      CCTCTCGGTATCACCAGA                       -3'         (SEQ ID NO.41)
```

EXAMPLE 2

Capture of HIV ss DNA Using a Capture Oligonucleotide and at Least One Additional Oligonucleotide as the Modular Probe Methods for the identification and/or capture of HIV target nucleic acid are performed analogously to those described in Example 1 for HCV using the following modular probes:
OMD82×13+OMD83 (13+18) 3'-TTAATTTCGGTCC-5' (SEQ ID NO.47)+3'-TTACCTACCGGGTTTTCA-5'-biotin (SEQ ID NO.48), or
OMD81+OMD82 (18+18) 3'-AGGATAACTTTGACATGG-5' (SEQ ID NO.49)+3'-TCATTTTAATTTCGGTCC-5'-biotin (SEQ ID NO.50)
in which OMD83 and OMD82 are capture oligonucleotides.

EXAMPLE 3

Capture of Sequencing Products Generated by the USP Primer Using a Capture Oligonucleotide and at Least One Additional Oligonucleotide as the Modular Probe Methods for the identification and/or capture of sequencing products generated by extension of the universal sequencing primer (USP) are performed analogously to those described in Example 1 for HCV using the following modular probes:
JL-H1/USP+JL-C2/USP (9+9) 3'-GACGTCCAG-5' (SEQ ID NO.1)+3'-CTGAGATCT-5'-biotin (SEQ ID NO.2), or
JL-H2/USP+JL-C1/USP (13+18) 3'-GTTCGAACGTACG-5' (SEQ ID NO.3)+3'-GACGTCCAGCTGAGATCT-5'-biotin (SEQ ID NO.4), or
JL-H2/USP+JL-H1/USP+JL-C2/USP (13+9+9) 3'-GTTCGAACGTACG-5' (SEQ ID NO.3)+3'-GACGTCCAG-5' (SEQ ID NO.1)+3'-CTGAGATCT-5'-biotin (SEQ ID NO.2)
in which JL-C1/USP+JL-C2/USP are capture oligonucleotides.

EXAMPLE 4

Use of Modular Oligonucleotides to Capture HCV DNA or RNA

MATERIALS AND METHODS

Magnetic Beads Carrying Capture Oligonucleotide C1

A hepatitis C virus specific capture oligonucleotide C1 (Table 2) was covalently coupled to paramagnetic beads (Dynal, AS). The magnetic beads (10 mg/ml) were conditions by washing twice in binding/washing buffer (B/W) (10 mM Tris-HCl (pH 7.5), 1 mM HCl, 2 M NaCl, 1 mM β-mercaptoethanol, 0.1% Tween 20). To reduce the non-specific adsorption of nucleic acids, 1 μg of E. coli tRNA (Boehringer Mannheim, Germany), was added to the beads which were then resuspended in 6×SSPE (0.9 M NaCl (pH 7.4), 60 mM NaH$_2$PO$_4$ and 7.5 mM EDTA) to a final concentration of 10 mg/ml.

Construction of Recombinant Hepatitis C Target

Hepatitis C RNA was extracted from serum samples from infected individuals and RT-PCR carried out as described by Yun et al, 1993 (J. Med. Virol., 39, p 57–61) using the primers OU49 and OD66 (see Example 1). This generated a 324 bp fragment containing the 5'non-translated region (NTR) of HCV (nucleotides 18–341 of the HCV genome, GenBank database, Accession:M62321) which was initially sub-cloned into the pGEM®-T (Promega, Madison, Wis., USA) vector and then inserted and cloned between the SphI and SalI restriction sites in the polylinker of plasmid pGEM®-4Z (Promega, Madison, Wis., USA).

Preparation of recombinant single strand hepatitis C DNA

Single strand DNA targets were prepared by PCR amplification of the 5'NTR of HCV cloned in pGEM®-4Z using the primers QU49 and QD66 as described in Example 1.

Solid phase (Beads) hybridisation of single strand DNA

Single strand DNA target was serially diluted in a 10 fold fashion (from $10^{13}$ to $10^4$ copies/ml HCV DNA) in a buffer containing 0.2 µg/µl $E.\ coli$ tRNA. A pre-hybridisation procedure was executed by incubation of 30 µl s/s DNA at 54° C. for 15 minutes in 100 µl 6× SSPE containing 1 µg $E.\ Coli$ tRNA and 0.5 µM oligonucleotide module H1-18 (Table 2). Control samples without this pre-hybridising oligonucleotide were prepared in parallel. DNA samples (with and without the pre-hybridising oligonucleotide) were then hybridised to the previously prepared magnetic beads (coupled C1) by incubating the hybridisation mix with 250 µg of beads for 1.5 hours at room temperature with constant rotation. After the hybridisation step, the beads were washed 6 times in B/W buffer (and changed to a new eppendorf tube prior to the final washing step) and resuspended in 100 µl $H_2O$. The DNA bound bead suspension was either used immediately in PCR or was stored at 4° C. PCR amplification was performed with 0.2 mM of the pre-hybridizing oligonucleotide module (H1-18) and the upstream primer (OU 49) in a 50 µl reaction volume containing 10 mM Tris-HCl (pH 8.3), 50 mM KCl, 2 mM $MgCl_2$, 0.2 mM dNTP's and 0.5 U of Amplitaq® DNA polymerase (Perkin-Elmer, Foster City, Calif.). The mixture was overlaid with 50 µl of light mineral oil (Sigma Chemical Co., St. Louis, Mo.) and 5 µl of resuspended beads were added through this layer of mineral oil. The PCR was performed with a Perkin-Elmer 9600 thermocycler (Perkin-Elmer, Norwalk, Conn.) using a temperature profile of 94° C. for 5 minutes, followed by 35 cycles of 94° C. for 15 seconds, 62° C. for 45 seconds, 72° C. for 1 minute and ending with 72° C. for 10 minutes. Semi-nested PCR was performed with H1-18 and IU50 (5'-GGA ACT ACT GTC TTC ACG CAG A-3') on 5 µl of the outer PCR product using the the same cycling conditions as above except with an annealing temperature of 55° C. PCR product were electrophoresed in a 1% agarose gel and visualised by ethidium bromide staining. During the PCR, multiple negative controls without template DNA were included. To avoid contamination, separate rooms were used for mixing the reagents, addition of sample and PCR analysis.

Preparation of recombinant hepatitis C RNA

Purified plasmid in pGEM®-4Z clone containing the 5' NTR of HCV was linearised downstream of the insert sequence by digesting 5 µg of DNA with NarI for 6 hours at 37° C. Phenol-chloroform extraction and ethanol precipitation was carried out. The resulting DNA pellet was dissolved in 50 µl diethylpyrocarbonate (DEPC) (Sigma Chemical Co., St. Louis, Mo.) treated $H_2O$. Transcription from the T7 promoter was performed on 1.5 µg of the linearised DNA at 37° C. for 1 hour in a 50 µl reaction volume containing 30 Units T7 PNA Polymerase (Pharmacia Biotech, Uppsala, Sweden) 40 mM Tris-HCl (pH 8.0), 30 mM $MgCl_2$, 10 mM β-mercaptoethanol, 0.4 mM dNTP's, 5 µg BSA (RNAse and DNAse) free Boehringer Mannheim, Germany), 10 mM DTT and approximately 40 Units RNAguard Ribonuclease Inhibitor (Pharmacia Biotech, Uppsala, Sweden) which generated a transcript of 649 nt in length. After transcription, template DNA was fragmented by restriction digestion (with AvaI) and treatment with 8 units RNase free DNAse I (Boehringer Mannheim, Germany) at 37° C. for 45 minutes. Following phenol-chloroform extraction and ethanol precipitation the resulting pellet was resuspended in 50 µl DEPC treated $H_2O$. The in vitro transcribed RNA was then analysed by gel electrophoresis and quantified by measuring $OD_{260}$. The $OD_{260}/OD_{280}$ ratio of the obtained RNA preparation was 1.87±0.1. A 5 and a 10 fold dilution series of RNA was then made in 10 ng/µl $Escherichia\ coli$ tRNA.

Biosensor analysis of recombinant hepatitis C RNA

Biosensor experiments were performed using a BIAcore 2000 instrument as described in Example 1, using C1 (Table 2) as the capture module with the exception that the injection volume was increased to 60 µl which was injected at a flow rate of 30 µl/minute. Six microlitres of RNA transcript was pre-hybridised to 0.5 µM oligonucleotide module (H1-18) in 100 µl 6× SSPE by incubation at 54° C. for 15 minutes followed by cooling to room temperature. Forty microliters of this hybridization mix was injected over the immobilised capture oligonucleotide (C1) at a flow of 2 µl/minute. Samples with no pre-hybridizing oligonucleotide were treated in exactly the same manner.

Solid phase (beads) hybridisation and detection of recombinant hepatitis C RNA

The procedure for capturing of RNA on beads is the same as that outlined for the capture of DNA, namely pre-hybridisation of the oligonucleotide module to 30 µl RNA at 54° C. for 15 minutes followed by capture on magnetic beads (linked to the HCV specific capture probe C1) by rotation at room temperature for 1.5 hours. RNA was serially diluted in a 5 fold fashion (from $5\times10^7$ to $1.6\times10^4$ copies/ml) in 0.2 µg/µl $E.\ coli$ tRNA. The beads with the captured mRNA were washed 4 times in B/W buffer and twice in cold RT-PCR buffer (they were changed to a new eppendorf tube prior to the final washing step) and resuspended in 100 µl of DEPC treated $H_2O$ before being used for RT-PCR. If the bead suspension was not used immediately for RT-PCR it was stored at −70° C. During transcription and RNA capture, all glassware and solutions (with the exception of Tris buffers) were DEPC treated to avoid possible contamination with RNase. Reverse transcription and outer PCR was performed in a one tube assay. Reverse transcription was carrried out on 5 µl of resuspended beads at 37° C. for 1 hour (with continous rotation) using 0.5 Units of MMLV Reverse Transcriptase, followed by PCR amplification with 2 Units Ampli Taq Gold® (Perkin-Elmer, Foster City, Calif.) in a total reaction volume of 50 µl. The reaction conditions were the same as those described above for the outer PCR with the addition of a pre-heating step at 94° C. for 12 minutes to activate Ampli Taq Gold®. Four micrograms of $E.\ coli$ tRNA was also included to prevent inhibition of Taq polymerase activity by reverse transcriptase [Sellner et al., 1992, Nucl. Acids Res., 20, p 1487–1490]. Positive and negative controls were included as well as a no reverse transcriptase control. Five microlitres of the outer PCR mix was used in the semi-nested inner PCR with the pre-hybridising oligonucleotide module (H1-18) and upstream primer IU50.

Modular assisted capture of hepatitis C in clinical samples using beads as the solid phase Serum samples from HCV-infected patients stored at −20° C. were used. The samples were genotyped (Yun et al, 1993, supra) and quantitated using Amplicor HCV Monitor Test (Roche Molecular Systems). Initially, 0.5 µM oligonucleotide module was pre-hybridised to 100 µl serum sample in 1 ml 6× SSPE containing 1 µg E. coli tRNA and 500 µl solution D (4 M guanidinium thiocyanate, 25 mM sodium citrate pH 7, 0.5% sarycosyl, 0.1 M β-mercaptoethanol) by heating at 60° C. for 10 minutes followed by rotation at room temperature for 45 minutes. Every 6th sample was a non-HCV serum negative control. Beads (250 µg) covalently coupled to C1, prepared as described above, were then added to this hybridisation mix and rotated at room temperature for 1 hour to facilitate capture. The beads were then washed 4 times in 100 µl B/W buffer and twice in 100 µl PCR buffer. The beads were resuspended in 20 µl $H_2O$, heated at 70° C. for 3 minutes and placed immediately on ice. RT-PCR was carried out using 10 µl of bead suspension as described by Yun et al, (1993, supra).

RESULTS

Hybridisation onto magnetic beads of single stranded DNA

In order to investigate the use of modular probes in magnetic bead mediated sample preparation of hepatitis C virus a model system was established, as schematically outlined in FIG. 8. The solid support for these experiments were beads with a covalently coupled 18 mer probe (C1) complementary to the virus target. An 18 mer long oligonucleotide module (H1-18) was designed and synthesized to anneal adjacent to the immobilised capture probe. Single strand DNA corresponding to the 5' non translated region (NTR) of hepatitis C was prepared by in vitro amplification and alkali strand separation according to the solid phase sequencing procedure. Quantified single strand DNA templates were 10 fold serially diluted. A pre-hybridisation step at 54° C. for 15 minutes involving the oligonucleotide module and serially diluted templates was performed. The hybridisation mixtures were subsequently incubated with magnetic beads for solid phase capture at room temperature for 90 minutes. After incubation the beads were washed and transferred to PCR tubes containing reagents and primers for single amplifications of the hepatitis C target region. Incubation of control samples without the oligonucleotide module in the pre-hybridisation step were performed in parallel. If amplification was successful a fragment of approximately 320 bp was expected. The results after the amplification are depicted in FIG. 9. In the top panel which corresponds to samples prepared with an oligonucleotide module, an amplified fragment can be observed down to the dilution step containing approximately $10^4$ starting molecules, while without the oligonuleotide module an approximately 10-fold lower sensitivity is achieved (a weak fragment is observed in the dilution step corresponding to $10^5$ starting molecules). This indicates the benefit of using a modular probe in bead assisted capture.

Hybridisation of RNA analysed by BIAcore

The previous set of experiments have focused on the use of DNA targets corresponding to the positive strand of the hepatitis C virus RNA genome. Therefore to allow for a more direct comparison with true samples, in vitro transcribed RNA samples were generated. After in vitro transcription of a linearised plasmid construct containing the target region, the 649 nt long transcript was extracted and quantified. The RNA produced was used as target in a similar set-up as previous BIAcore analysis of single stranded DNA. Thus the RNA was prehybridized with oligonucleotide module (500 nmol) as used above (H1-18, 18 mer) and then passed over the immobilised capture oligonucleotide (C1, biotinylated 18 mer) on the chip surface. A control sample without the oligonucleotide module was processed in parallel. These two samples were also passed over a chip surface without any immobilised capture oligonucleotide which acted as a blank control. The resulting data is presented as an overlay plot for the two subtracted samples in FIG. 10. The data clearly indicates that significantly more target RNA is captured when a module probe has been employed. It is also important to note that the reactions have not reached saturation during the injection pulse (20 min) and therefore it is likely that the absolute differences are even higher.

Hybridisation and detection of RNA onto magnetic beads

As a result of the successful BIAcore analysis the model system was also evaluated on magnetic beads with a covalently bound capture oligonucleotide (C1). To facilitate comparison, the template RNA was 10-fold serially diluted as described previously for DNA templates. The dilutions were then incubated at 54° C. for 15 minutes with the oligonucleotide module 18 mer probe (H1-18) followed by a further incubation with magnetic beads at room temperature for 90 minutes. Control samples without H1-18 were processed in parallel. After a washing step a one tube RT-PCR was performed on the samples. The results are presented in FIG. 11 and show a weak fragment in the dilution corresponding to approximately $10^4$ starting RNA molecules, while without the oligonucleotide module an approximately 10-fold lower sensitivity is achieved. To further investigate the quantitative differences a more narrow dilution series (5-fold) was used in an RT-nested PCR experiment. Nested PCR will allow for a comparison at the PCR plateau level at which all dilutions have reached saturation irrespective of the number of starting copies. FIG. 12 shows that with an oligonucleotide module probe 140 RNA starting copies can be detected, while without the oligonucleotide module probe 700 copies are required for detection. These results are in complete agreement with the results obtained with single stranded DNA templates.

Detection of hepatitis C in clinical samples using module assisted capture

The encouraging results with out two model systems based on either DNA or RNA targets indicated that modular probes improved capture onto either a chip surface or a solid particle. This lead us to evaluate the approach on clinical samples containing hepatitis C virus. First we analysed two HCV positive samples (using a similar approach to that outlined above) by serially diluting the samples 5-fold followed by incubation in a denaturing solution containing 500 nmol of the oligonucleotide module at 60° C. for 10 minutes. These were then incubated at room temperature for 45 minutes before addition of beads with covalently coupled capture probe and a further incubation at room temperature for 60 minutes. After washing, the beads were directly transferred into RT-PCR tubes as described above. FIG. 13 shows one of the two samples with and without a oligonucleotide module and confirms the same trend as previously demonstrated i.e. that inclusion of an oligonucleotide module improves the capture performance. Also upon a further amplification of these two serially diluted samples with inner primers an approximate absolute value is obtained which indicates up to a 25-fold higher sensitivity with the oligonucleotide module (data not shown).

Finally, a total of 19 clinical samples were then analyzed using the described approach. All of these had previously been quantified by a commercial test (Amplicor HCV Monitor Test, Roche). In 5 of these 14 samples a comparison with and without oligonucleotide module was also possible. The results are depicted in Table 4 and show a good correlation between the commercial test and the module assisted capture for all virus titers. Interestingly, in one of the five samples that were compared, viral capture failed when the oligonucleotide module was omitted. This confirms the trend seen with the model systems and truly shows that the prehybridization step also increases the sensitivity of detection for clinical samples.

DISCUSSION

This study shows the utility of modular oligonucleotides in the capture of single stranded templates. Interestingly, it is not limited only to short fragments as employed in our model system but also complete hepatitis C genomes are more efficiently captured. No difference can be observed between DNA and RNA targets which could have been expected due to their different chemical structures. In contrast identical capture patterns were displayed when tested with and without an oligonucleotide module.

Preliminary studies have also suggested that the protocol for viral capture could be shortened by combining the prehybridization, sample lysis (in guanidium thiocyanate) and bead capture in a single step. Thereby only a simple washing step is required prior to RT-PCR making the system very attractive for automated approaches.

TABLE 4

Summary of the results using clinical samples

| Sample | Genotype | Quantitative determination (copies/ml) | Routine HCV procedure | Solid Phase approach |
|---|---|---|---|---|
| 1 | 1b | $2.5 \times 10^6$ | + | + |
| 2 | 2b | $2.5 \times 10^6$ | + | + |
| 3 | 1b | $2.5 \times 10^6$ | + | + |
| 4 | 2b + 1b | $5.0 \times 10^5$ | + | + |
| 5 | 1a | nd | + | + |
| 6 | control | | | − |
| 7 | 3a | $1.0 \times 10^5$ | + | + |
| 8 | 1a + 1b | $1.0 \times 10^5$ | + | + |
| 9 | 3a | $1.0 \times 10^5$ | + | + |
| 10 | 2b + 1b | $5.0 \times 10^5$ | + | + |
| 11 | 1a + 1b | $5.0 \times 10^5$ | + | + |
| 12 | control | | | − |
| 13 | 1b | $1.0 \times 10^5$ | + | + |
| 14 | 3a | $2.0 \times 10^4$ | + | + |
| 15 | 1a | $5.0 \times 10^5$ | + | + |
| 16 | 2b | $5.0 \times 10^5$ | + | + |
| 17 | 1b | $2.5 \times 10^6$ | + | + |
| 18 | control | | | − |
| 19 | 2b | $5.0 \times 10^5$ | + | + |
| 20 | 1a | $1.0 \times 10^5$ | + | + |
| 21 | 3a | $2.5 \times 10^6$ | + | + |
| 22 | 1b | $1.0 \times 10^5$ | + | + |
| 23 | control | | | − |

EXAMPLE 6

Oligonucleotide Module Assisted Capture of HIV-1 Virus

Experiments on a model system consisting of a cloned fragment of the HIV-1 genome, the pol region (Table 5) are described. The pol region is a frequency used target in different diagnostic systems for detection and quantification of HIV-1 virus.

MATERIALS AND METHODS
Construction of recombinant HIV target and preparation of single strand HIV DNA PCR was carried out on the proviral HIV-1$_{MN}$ strain (Myers et al, 1991, Human Retrovirus and AIDS 1991, Los Alamos National Laboratory, Los Alamos, N.M.) using POL specific primers JA 79 and TV 84 (Table 5). This generated a 378 bp fragment which was cloned into the pGEM®-T vector. Single strand DNA was prepared by PCR amplification of this cloned POL gene using the vector specific primers RIT 28 and RIT 29. The resulting biotinylated 800 bp fragment was subjected to strand specific elution as described in Example 1.

Biosensor analysis of recombinant HIV DNA

A HIV specific biotinylated oligonucleotide (OMD82, see Example 2) was immobilised on the sensor chip followed by injection of 50 μl of single stranded HIV DNA prehybridised to OMD 81 (as described for the HCV target). A control sample with no oligonucleotide module was run in parallel. The target sequence in this case is 5'-TCCTATTGAAACTGTACCAGTAAAATTAAAG CCAGG-3' (SEQ ID NO. 51) which is nucleotides 473–509 of the HIV-1 genome.

TABLE 5

Primers

JA79 (pol)
5' -ACAGGAGCAGATGATACAGTATTAG-3'
(SEQ ID NO.44)

TV 84 (pol)
5' -GACATTCGAATTCCCTTCCTTTTCCATTTCTGTAC-3'
(SEQ ID NO.45)

RIT 28 (vector)
5' -AAAGGGGGATGTGTGCTGCAAGGCG-3'
(SEQ ID NO.43)

RIT 29 (vector)
5' -biotin-GCTTCCGGCTCGTATGTTGTGTG-3'
(SEQ ID NO.46)

RESULTS

Single strand DNA pol targets were generated in a similar manner as the hepatitis C case; ie. strand specific elution of biotinylated PCR amplicons using streptavidin coated magnetic beads. The resulting single strand DNA targets were injected over a sensor chip surface containing a complementary probe sequence and the interaction was measured in real time by the biosensor system. The experiments were performed with and without an oligonucleotide module. The results (FIG. 14) show again the modular probes do enhance capture as determined by the overlay plot from the biosensor experiment.

EXAMPLE 5

Use of Modular Oligonucleotides to Capture Sequencing Products

The following example describes the use of modular oligonucleotides to capture the population of sequencing products corresponding to a particular primer/vector/insert which may optionally be present in a complex mixture with other populations of sequencing products.

MATERIALS AND METHODS
Single template experiments
Preparation of PCR-products pUC18 and pBluescript plasmids containing various inserts were used as a template in PCR with RIT 27 (5'-GCTTCCGGCTCGTATGTTGTGTG-3') (SEQ ID NO. 42) and RIT 28 (5'-AAAGGGGGATGTGTGCTGCAAGGCG-3') (SEQ ID NO. 43) primers. Amplification was performed in a 50 μl reaction volume containing 10 mM Tris-HCl (pH 8.3), 50 mM KCl, 2 mM MgCl$_2$, 0.1% Tween® 20, 0.2 mM dNTP's, 0.5 U of Taq DNA polymerase (Perkin-Elmer, Norwalk, Conn.) and 0.075 μM of each primer, using a Perkin-Elmer 9600 thermocycler (Perkin-Elmer, Norwalk, Conn.). The temperature profile was 94° C. for 5 minutes, followed by 30 cycles of 94° C. for 30 seconds and 72° C. for 2 minutes, and ending with 72° C. for 10 minutes.

Cycle sequencing with four colour dye primer

The following reagents were mixed together (on ice): A and C mix: 26 mM Tris-HCl (pH 9.0), 6.5 mM MgCl$_2$, 150 μm dNTP, 0.5 μm ddNTP (A or C), 1.5 U ThermoSequenase (Amersham Pharmacia Biotech, Sweden), 20 nM Universal (forward) sequencing primer (USP) 5'-dye-CGTTGTAAAACGACGGCCAGT-3'(SEQ ID NO. 52), or Reverse sequencing primer (RSP), 5'-dye-TTCACACAGGAAACAGCTATGACC-3'(SEQ ID NO. 53), A reactions Joe-dye and C reactions Fam-dye (Genpak Ltd, England), 1 μl PCR product and H$_2$O to a final volume of 10 μl per reaction. G and T mix: 26 mM Tris-HCl (pH 9.0), 6.5 mM MgCl$_2$, 150 μm dNTP, 0.5 μm ddNTP (G or T), 1.5 U ThermoSequence, 20 nM USP or RSP primer, G reactions Tamra-dye and T reactions Rox-dye (Genpak Ltd, England), 2 μl PCR product and H$_2$O to a final volume of 20 μl per reaction.

Cycle sequencing was carried out using a temperature profile of 95° C. for 1 minute followed by 28 cycles cycling between 96° C. for 30 seconds and 56° C. for 1 minute. The cycle sequencing products were subsequently pooled prior to solid phase capture.

Preparation of beads

Fifteen microlitres of paramagnetic beads (10 mg/ml), covalently coupled to a capture probe (selected from Table 1), were washed twice in 15 μl binding/washing (B/W) buffer (10 mM Tris-HCl pH 7.5, 1 mM EDTA, 2M NaCl, 1 mM β-mercaptoethanol, 0.1% Tween 20). The washed beads were resuspended in 15 μl 6×SSPE (0.9 M NaCl pH 7.4, 60 mM NaH$_2$PO$_1$H$_2$O, 7.5 mM EDTA).

Capture of cycle sequencing products

Fifty-five microlitres of the pooled cycle sequencing product was incubated with 30 pmoles of modulating module (selected from Table 1), 150 μg beads and H$_2$O in 115 μl 6×SSPE at 54° C. for 15 minutes. The beads were washed once in 100 μl B/W buffer and once in 100 μl 1×TE buffer. The captured cycle sequencing products were eluted from the beads with 2 μl of 95% formamide prior to loading on a 377 ABI sequencer.

Optimization

The assay was optimized for the specific pUC18 forward bead (Table 1). The amount of beads were varied between 40 μg and 250 μg, which resulted in a change in total volume between 104 μl and 125 μl and the efficiency was determined by analysis of the automatically generated peak signals for the different fluorophores after each gel electrophoresis experiment. Next the amount of modulating module was varied between 0 and 50 pmoles using 150 μg of beads (in a constant total volume of 115 μl). A temperature titration between 20° and 70° was performed using 150 μg of beads and 30 pmole modulating module, concentrating on the temperature interval close to the annealing temperature of the immobilised probe. Finally incubation times, both at 54° C. and following incubation at room temperature, between 0 and 15 minutes were studied.

Sequence product mixtures

Experiments with mixtures of different cycle sequencing products were performed in order to study the specificity of the capture probes. To further investigate the specificity pUC18 beads were incubated with pBluescript cycle sequencing products and vice versa. To achieve this a bead with an immobilised probe specific for pBluescript was synthesized together with a suitable modulating module (Table 1). PCR product for these two templates were generated and subsequently used for 4 separate cycle sequencing reactions in both directions using a forward and reverse sequencing primer, identical for the two vectors. These four cycle sequencing products were than mixed into equal proportions to either 55 μl (normal volume for single sample) or 220 μl (4 times the volume for a single sample) final volume mixtures. The capture beads were then used to enrich for its specific sequencing product, i.e The pUC18 bead captured sequencing reactions generated by the forward sequencing primer on pUC18 vector and the pBluescript bead captured sequencing reactions generated by the forward sequencing primer on pBluescript vector. Capture was performed as usual for the smaller volume but when 220 μl were used the total volume of the reaction was increased to 354 μl.

Elution of captured sequencing products using water and heat

The cycle sequencing products were eluted from the beads either with 2 μl of 95% formamide as described above, or with water and heat. In the latter case captured cycle sequencing products were resuspended in 10 μl water and heated at 95° C. for 3 minutes. The supernatant was transferred to new tubes while still hot. Loading buffer (2 μl of 95% formamide) was added to the supernatant prior to evaporation of the water at 95° C.

Re-use of beads

Experiments with re-use of beads were performed with both elution methods. Six iterative captures were done using the same beads. Between captures the beads were washed in the same manner as described under preparation of beads.

Comparative ethanol precipitation

Fifty-five microlitres of the cycle sequencing product was precipitated with 138 μl of 96% ethanol and 5.5 μl of 3 M NaAC and, after incubation at −20° C. for 10 minutes, the DNA was recovered by centrifuation for 20 minutes. The resulting pellet was washed in 700 μl 80% ethanol followed by centrifugation for 5–10 minutes. Finally, the pellet was dried (over night or in speedvac for 10 minutes) and resuspended in 2 μl 95% formamide.

Multiplex experiments

Multiplex cycle sequencing with four colour dye-primer PCR products, obtained as described above, from both pUC18 and pBluescript were used as templates in a quatraplex cycle sequencing reaction. In order to obtain four different sequencing products both universal (USP) and reverse (RSP) sequencing primer were used. The reaction was carried out as described above for a single template with the amount of water reduced to compensate the increased volumes of primer and PCR product.

Capture of cycle sequencing products from multiplex cycle sequencing

In the quatraplex cycle sequencing described above four different sequencing products are obtained. These were captured in an iterative fashion with their respective bead and modulating module. After incubation with the first bead the supernatant was transferred to a new tube and 150 μg of the next bead and 30 pmol of the corresponding modulating module were added. Another incubation of 15 minutes at 54° C. was performed. This was repeated for each sequence. The beads with captured sequencing products were treated as described for a single template.

RESULTS

In these experiments, a model system consisting of a pUC18 plasmid target with an insert of approximately 1200 bp and a capture bead with an immobilised probe (Table 1) complementary to a common vector-derived sequence of the generated Sanger fragments together with an adjacent positioned modulating module (Table 1, FIG. 15) was used. DNA templates, in this case PCR products, were used as DNA source in a cycle sequencing reaction resulting in single-stranded Sanger fragments. These fragments were captured onto the bead surface by hybridisation in a one-step reaction by mixing with beads (with an immobilized probe) and a modulating module.

In the initial experiments with the model system the beads with captured fragments were washed and then resuspended in formamide (by which the fragments were eluted from the bead surface) and loaded on an automated DNA sequencer.

An example of these initial experiments is shown FIG. 16 which displays the corresponding gelfile after a capture performed at 54° C. Indeed this initial and relatively quantitative analysis showed the advantage of an assisting modulating module leading to similar fragment intensities as the reference sample (lanes 3 and 4 compared to lane 5). In addition, the quality of the different obtained DNA sequences were compared using the standard evaluation software indicating improved accuracy using the capture strategy (data not shown). The ethanol precipitated material had an accuracy of 92.6% over the 500 first bp, while capture with modular probe had an accuracy of 96.6%. The accuracy for samples without probe was 90.2%.

Optimisations of capture efficiency

To further improve the capture protocol a number of parameters were investigated such as the amount of beads and modulating module, incubation temperatures and time.

Figure 17A:
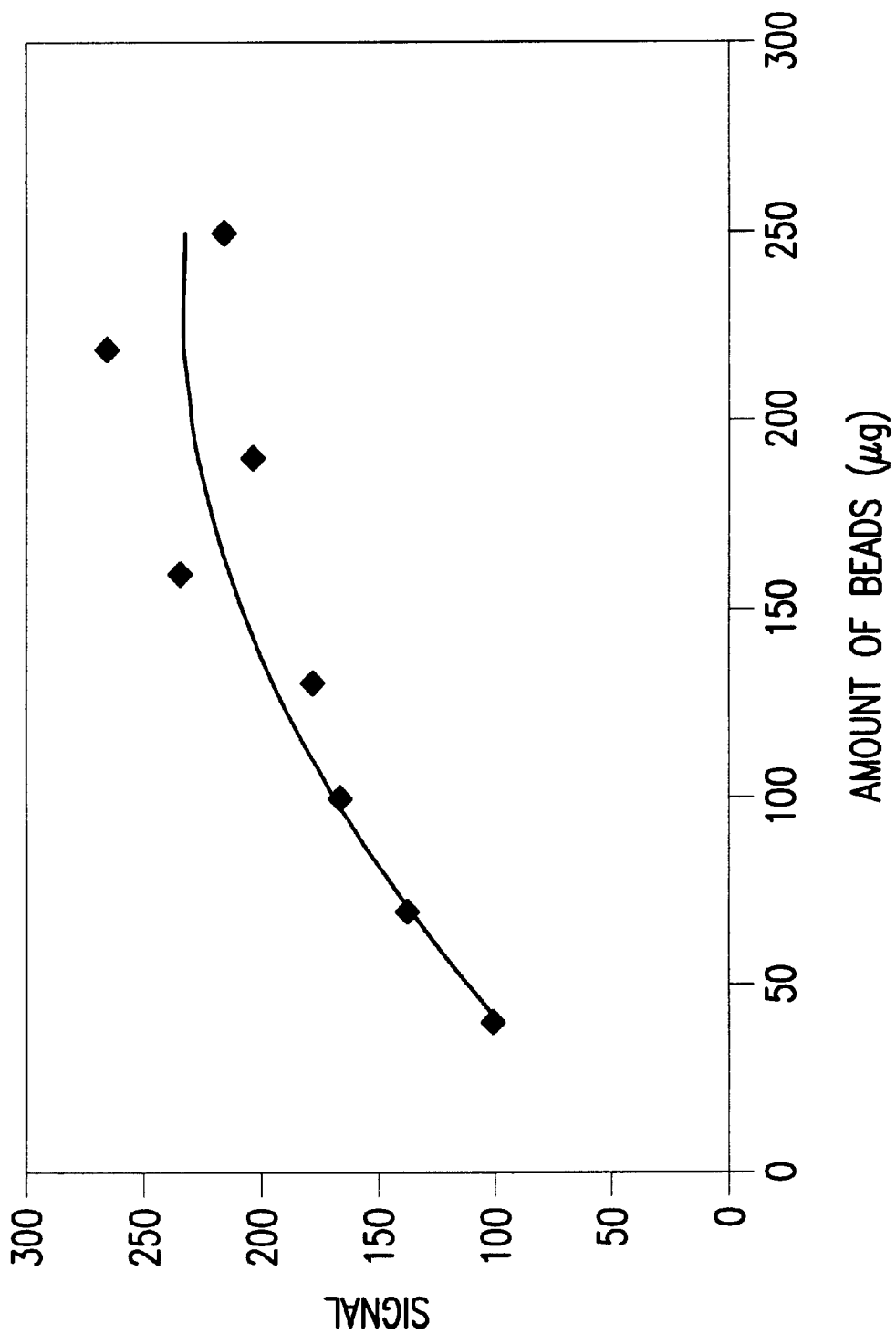
FIG. 17A shows the results of bead optimization of the modular capture using the specific modular nucleotides in Table 1 for use with PUC18 in the forward direction.
Figure 17B:
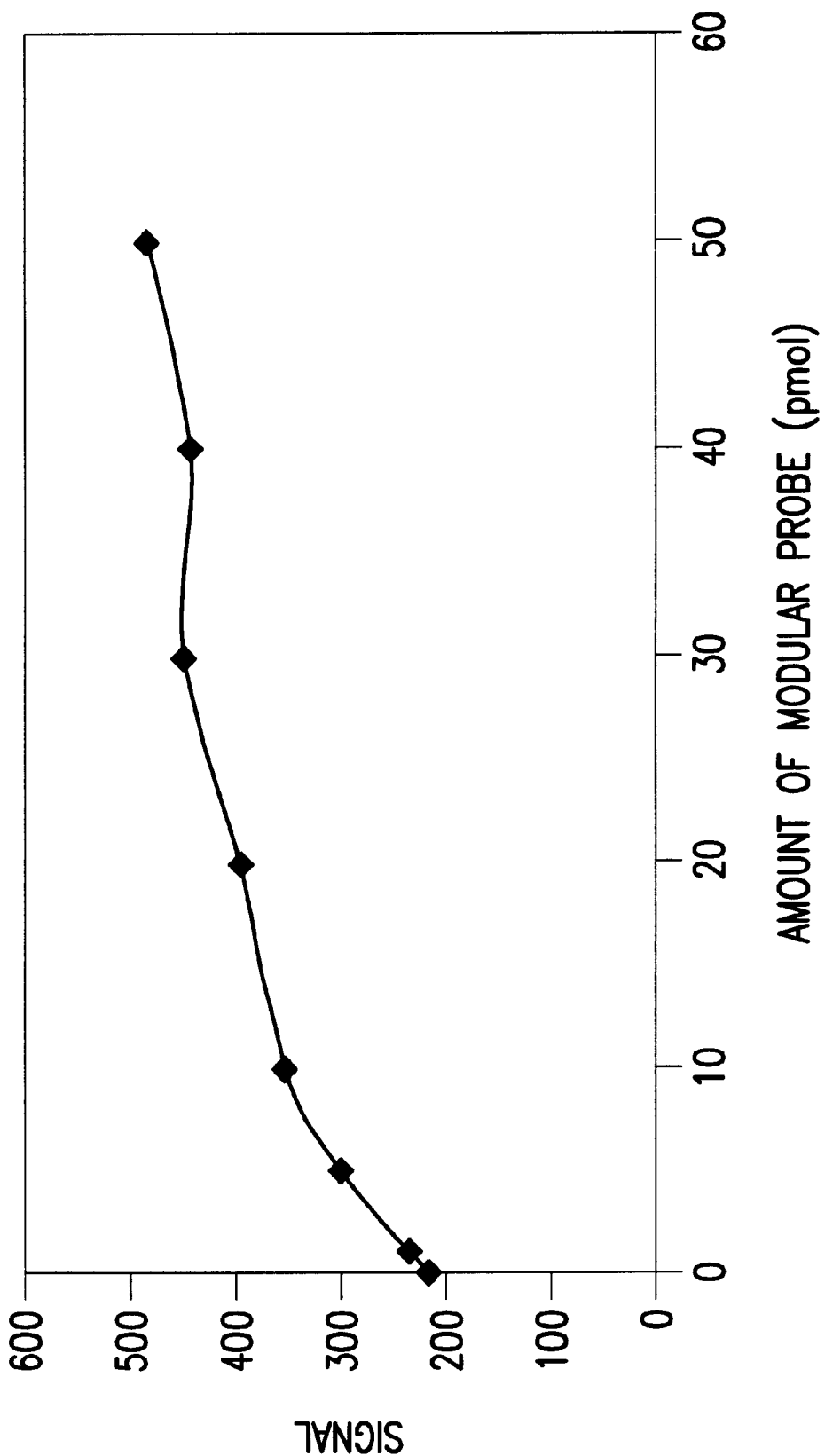
FIG. 17B shows the results of modulating module optimization of the modular capture using the specific modular nucleotides in Table 1 for use with PUC18 in the forward direction.
Figure 17C:
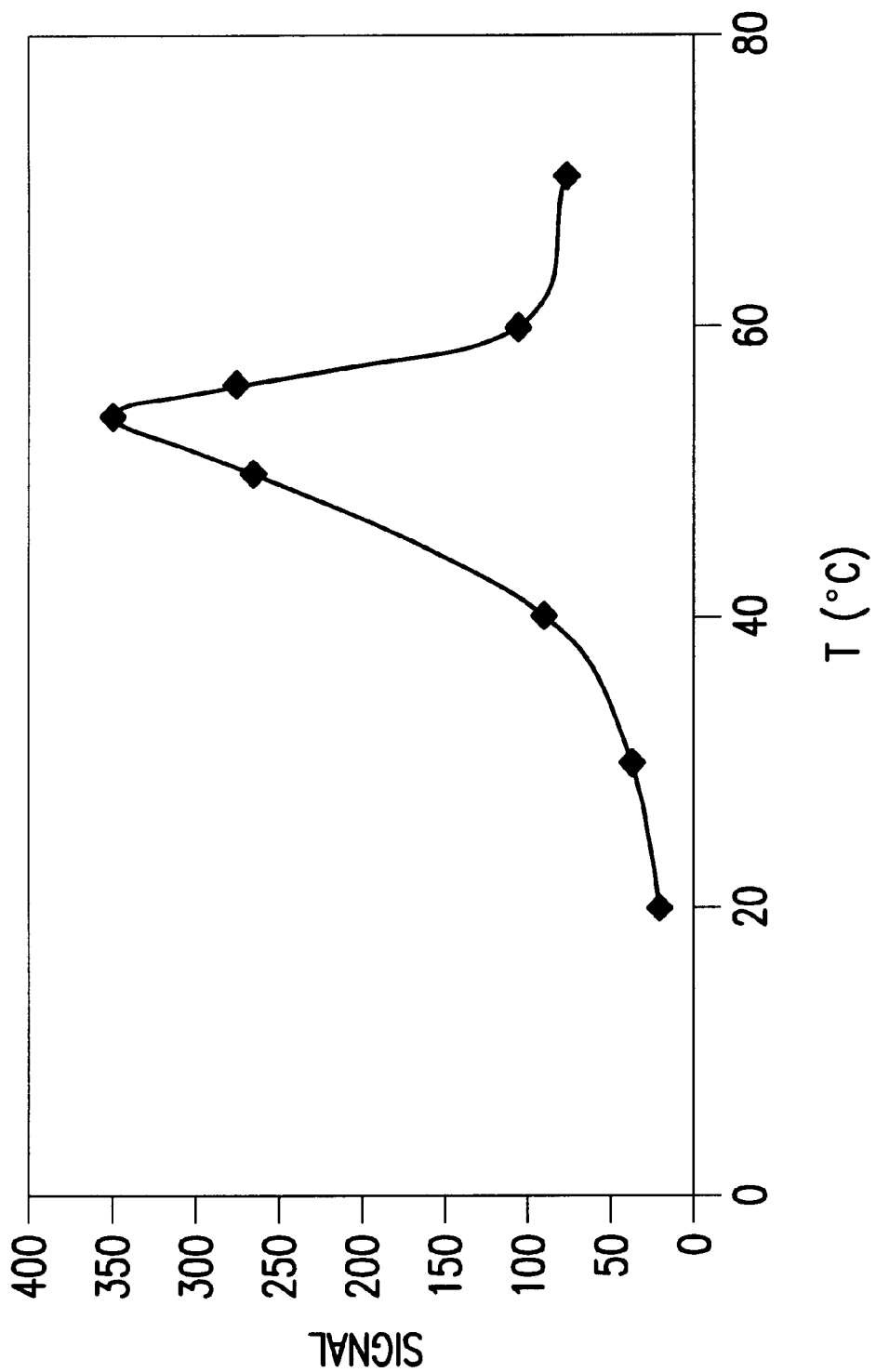
FIG. 17C shows the results of capture temperature optimization of the modular capture using the specific modular nucleotides in Table 1 for use with PUC18 in the forward direction.
Figure 17D:
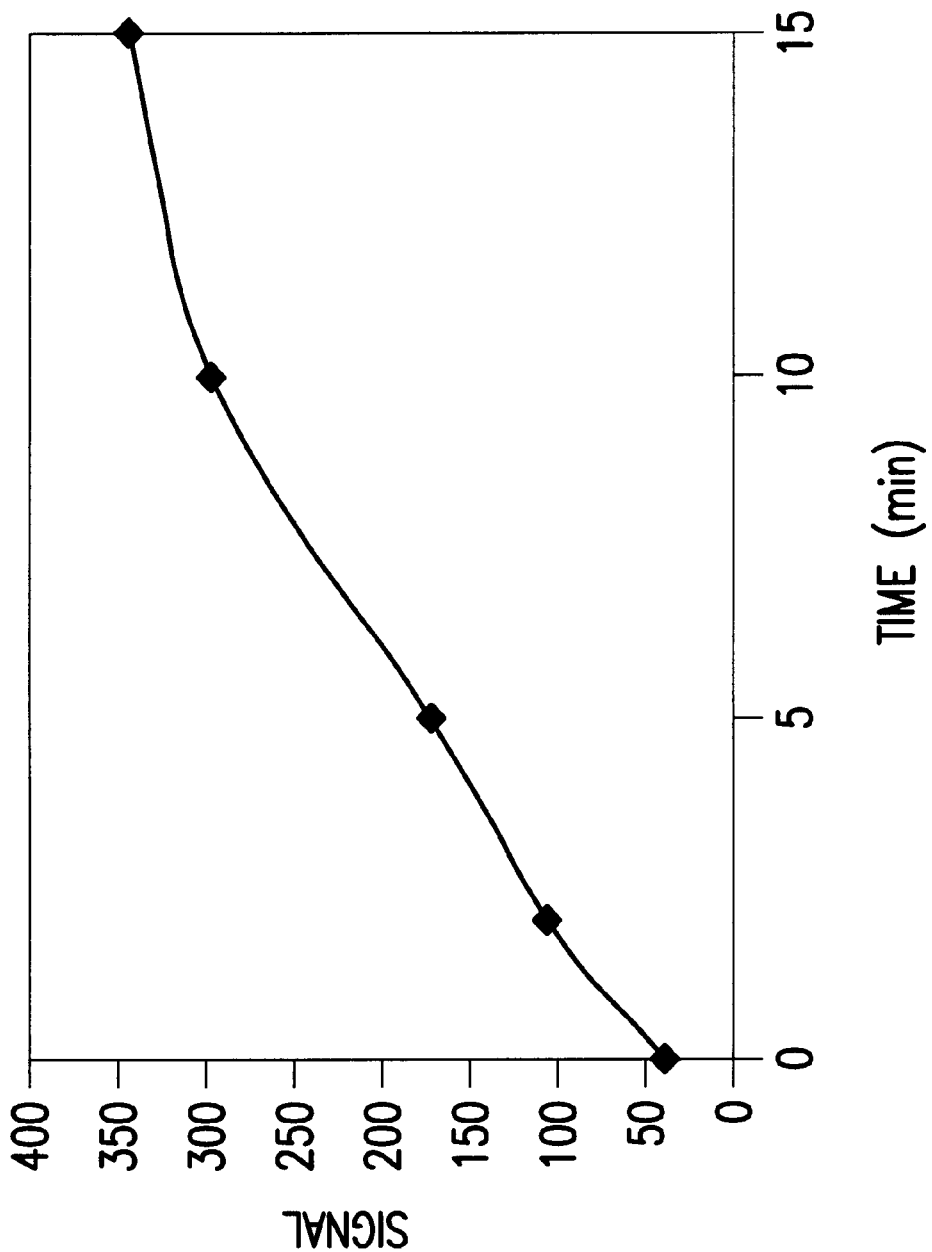
FIG. 17D shows the results of incubation time optimization at 54° C. of the modular capture using the specific modular nucleotides in Table 1 for use with PUC18 in the forward direction.
Figure 17E:
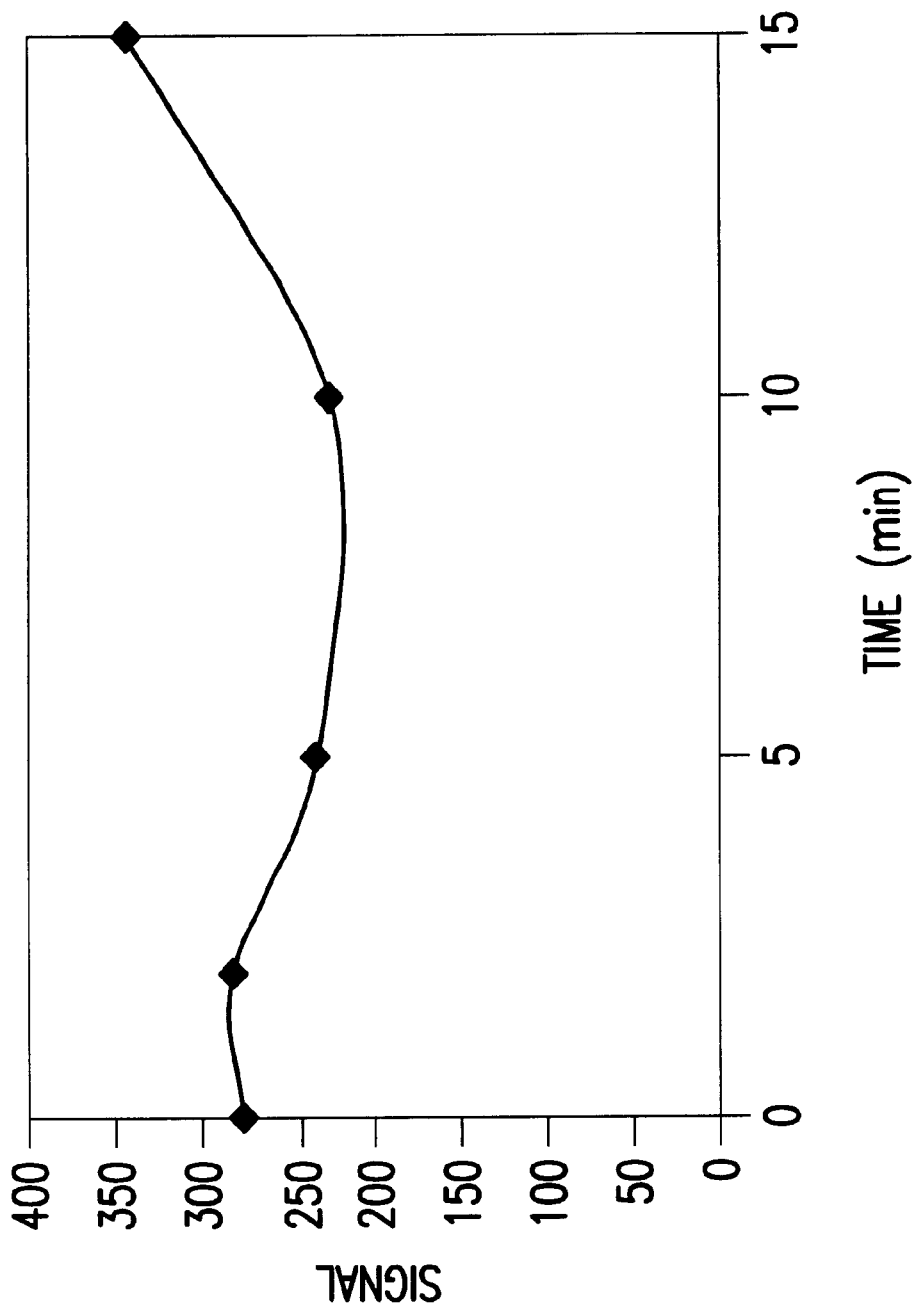
FIG. 17E shows the results of incubation time optimization at room temperature of the modular capture using the specific modular nucleotides in Table 1 for use with PUC18 in the forward direction.

Again the model system consisted of the pU18 system and the corresponding capture bead. In the first set of experiments the amount of beads were investigated. Triplicate samples (in all optimisations) were analysed in the range of 40 to 250 µg beads. As shown in FIG. 17A a slight decline in efficiency is observed for lower amounts than 150 µg beads. Secondly, the amount of modulating modules were investigated in the interval 0 to 50 pmol per capture. A decline in efficiency was observed for lower amounts than 30 pmoles (FIG. 17B). Thirdly the capture temperature was investigated in the interval 20° C. to 70° C. As demonstrated in FIG. 17C the capture temperature has a clear effect on the efficiency with a maximum yield at 54° C. (close to the Tm of the immobilised probe) and a rather sharp declining curve at both higher and lower temperatures. Finally the incubation time at the optimum capture temperature (54° C.) as well as the subsequent incubation at room temperature was investigated. From the data present in FIGS. 17D and 4B it is clear that the incubation at the capture temperature requires at least 15 minutes in order to achieve a maximum yield in capture, while the yield is rather invariant in respect to incubation time at room temperatures.

Re-use of beads

Figure 18A:
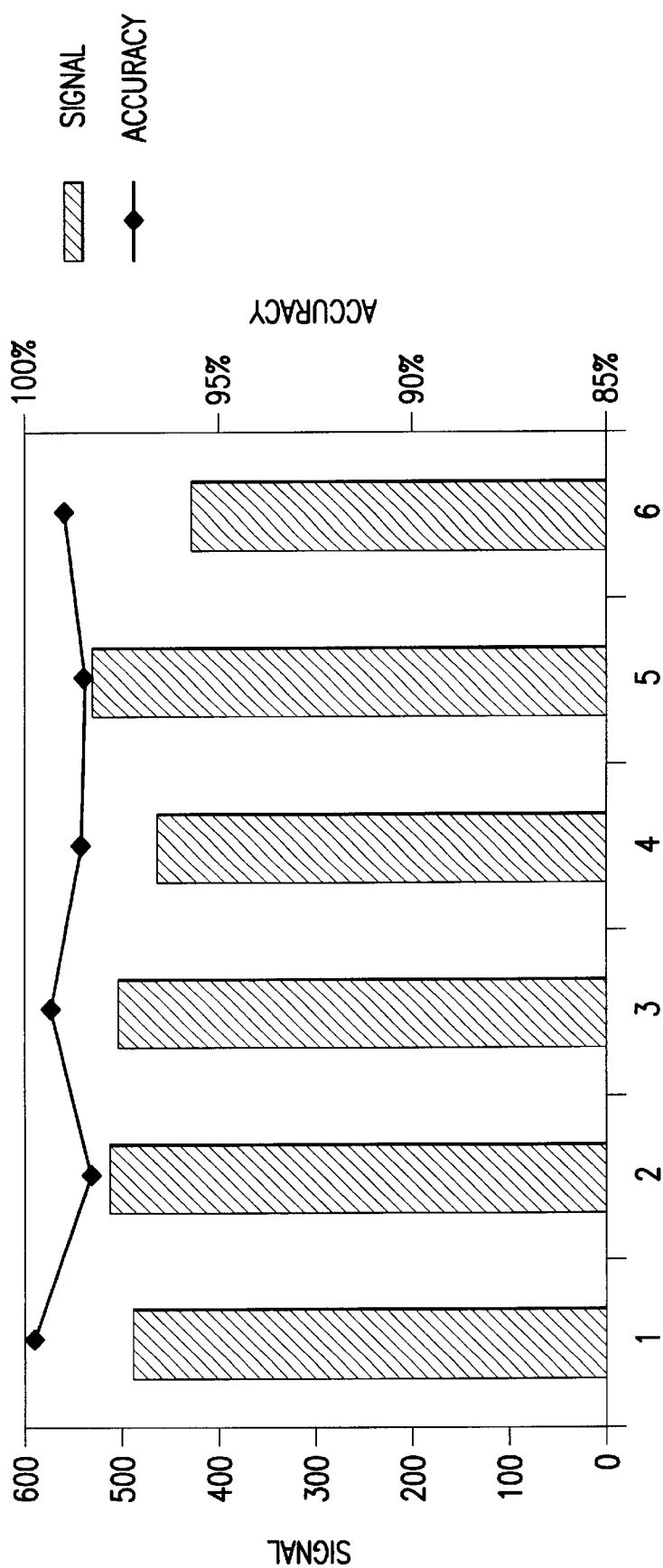
FIG. 18A and FIG. 18B shows the results of the reuse of beads based on elution with formamide and elution with heat and water, respectively.
Figure 18B:
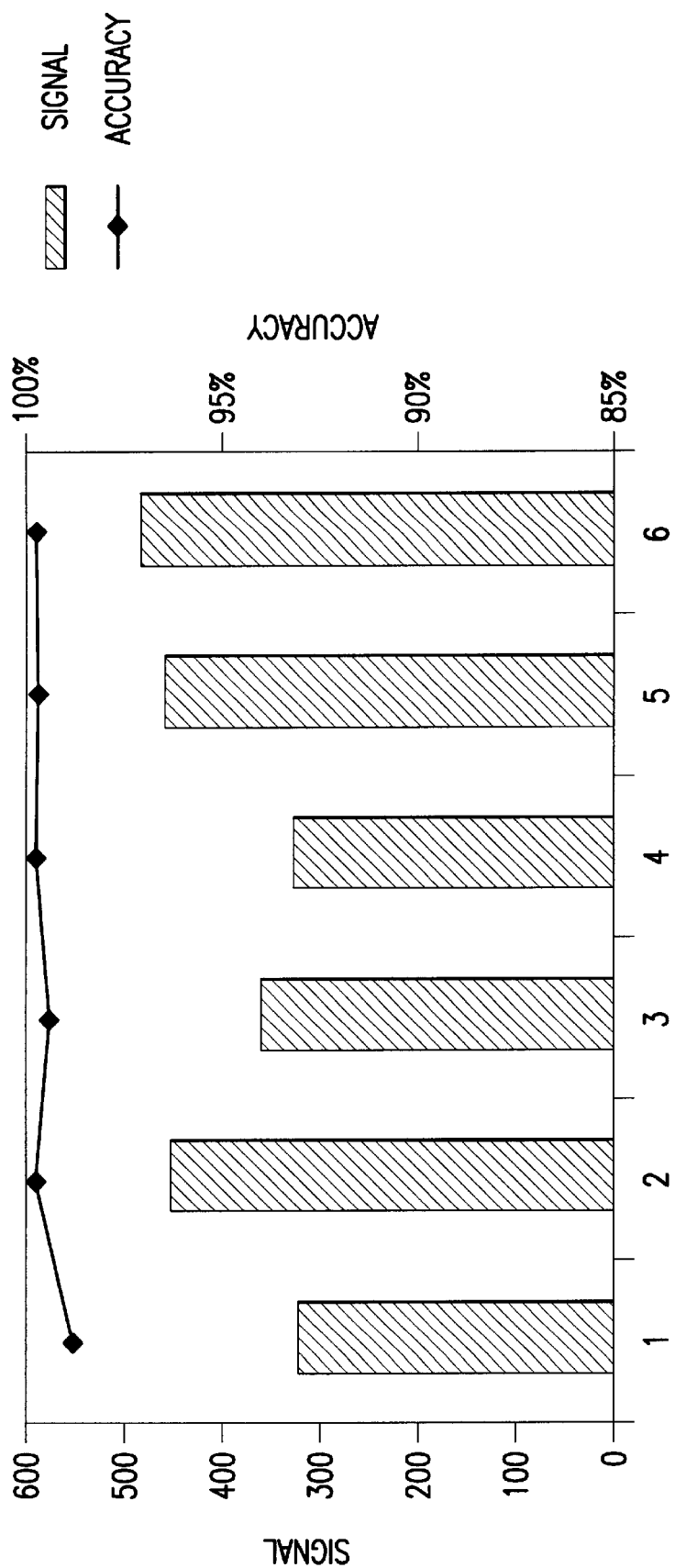

Two formats for iterative re-use of beads were investigated. The first protocol is based on formamide elution after capture and direct loading onto the gel, while the second protocol involves a heat release at 95° C. in a low salt buffer and transfer of the supernatant into a new tube to which formamide is added. Remaining water is evaporated by heat. The results for the first protocol is shown in FIG. 18A for 6 iterative cycles of re-use. The graph presents signal intensities and the accuracy over the 500 first bases after each cycle. The signal and the accuracy remains high even after 6 cycles. The corresponding data for the heat release, the preferred protocol from the point of automation and handling of toxic formamide, demonstrate an even higher accuracy (FIG. 18B).

Specificity of the capture protocol

In order to investigate the specificity of the optimised protocol we extended the model system to involve an additional plasmid vector, pBluescript with an insert of approximately the same length as the previously used pUC18 plasmid. The method is described under "Sequence product mixtures" above in which the products of 4 separate cycle sequencing reactions were mixed and capture of selected populations were performed. The data which were obtained is shown in FIG. 19. Each bar corresponds to use of a specific bead and it is evident that specific capture is achieved with excellent accuracy over 500 bp and as expected higher signal are generated by increasing the amount of sample. As a control a non-related cycle sequencing product with no homology with the immobilised probe or modulating module was also tested with the two bead types giving no measurable signal (FIG. 19).

Multiplexing sequencing and purification

A multiplex system was established to take advantage of the unique specificity obtained with the capture beads and accompanying modulating module. The principle was to run parallel cycle sequencing reactions in a single tube corresponding to forward and reverse sequencing primer with two plasmids as targets (containing inserts of approximately 800 to 1500 bp) and from the generated pool of various sequencing reactions iteratively enrich individual reactions with the use of capture beads. For example in the first round of capture the pUC18[reverse] beads are used to capture the corresponding targets, and the supernatant is subsequently moved to the next step, capture with for example pUC18 [forward] beads etc. This then results in four beads with "directionally" captured material which enables individual elution and loading. Representative chromatograms are shown in FIG. 20 demonstrating specific capture of three of the individual cycle sequencing reactions from a quatraplex cycle sequencing reaction (two plasmids in two directions).

DISCUSSION

The above results show that purification of cycle sequencing products by ethanol precipitation may be replaced with a capture assay using modular oligonucleotides.

What is claimed is:

1. A method for isolating primer extension products, produced from a template vector, said products containing sequences corresponding or complementary to i) a primer binding region, ii) an insert and iii) vector-derived sequence(s), wherein said method comprises:
   a) binding a modular oligonucleotide comprising at least two modules to adjacent stretches on said primer extension products, wherein said modular oligonucleotide is complementary to and capable of binding to said vector-derived sequence of said primer extension products, wherein at least one of said modules is a capture module which is immobilized or has means for immobilization; and
   b) isolating said primer extension products bound to said modular oligonucleotide.

2. A method as claimed in claim 1, wherein said vector-derived sequence(s) of said primer extension products is derived from any region of a particular vector and contains a portion which remains intact after longing of the insert into a particular restriction site of a multiple cloning site of said vector and to which the modular oligonucleotide anneals.

3. A method as claimed in claim 1, wherein said vector-derived sequence(s) of said primer extension products is
   derived from any region of a particular vector and
   contains a portion which remains intact after longing of the insert, regardless of restriction site of a multiple cloning site of a particular vector into which the insert is cloned, and to which the modular oligonucleotide anneals.

4. A method as claimed in claim 1 or 2 wherein said modular oligonucleotide consists of two or three modules.

5. A method as claimed in claims 1 or 2 wherein each module has ≧9≦18 nucleotides.

6. A method as claimed in claim 1 or 2 wherein said modular oligonucleotide comprises a total of at least 18 nucleotides.

7. A method as claimed in claim 1 or 2 wherein the modules when bound to said primer extension products are less than 2 bases apart.

8. A method as claimed in claim 7 wherein said modules are directly adjacent.

9. A method as claimed in claim 1 or 2 wherein immobilization is via the streptavidin:biotin binding system.

10. A method as claimed in claim 1 or 2 wherein said primer extension products are contacted directly with all modules of said modular oligonucleotide in a single hybridization step.

11. A method as claimed in claim 1 or 2 comprising the steps of
   1) contacting a sample containing the primer extension products with all modules of the modular oligonucleotide, wherein the capture module is immobilized on a solid support;
   2) binding said modules by hybridization;
   3) separating target primer extension products bound to said solid support; and
   4) washing said solid support.

12. A method as claimed in claim 1 or 2 wherein said binding is performed at between 40° C. and 60° C. for between 15 to 90 minutes.

13. A method as claimed in claim 1 or 2 wherein said modular oligonucleotide comprises a pair of oligonucleotides, wherein said pair of oligonucleotides is selected from the group consisting of:
5'-NNAAGCTTACT-3' (SEQ ID NO. 7) and
   5'-GGCCGTCGTTTTACAACG-3' (SEQ ID NO. 8)
5'-NNNNAATTCGCCCTATAG-3' (SEQ ID NO. 9) and
   5'-TGAGTCGTATTAC-3' (SEQ ID NO. 6)
5'-GAATTCACGGAAATCATG-3' (SEQ ID NO. 10) and
   5'-GTCATAGCTGTTTCCTGT-3' (SEQ ID NO. 11)
5'-TCCAGCTTTTGTTCC-3' (SEQ ID NO. 12) and
   5'-CTTTAGTGAGGGTTAATT-3' (SEQ ID NO. 13)
5'-NNTTGAGTATTCTATAG-3' (SEQ ID NO. 14) and
   5'-TGTCACCTAAATAGCT-3' (SEQ ID NO. 15)
5'-TCTAGAGTCGACCTGCAG-3' (SEQ ID NO. 16) and
   5'-GCATGCAAGCTT-3' (SEQ ID NO. 17)
5'-ACCCAATTCGCCCTATAG-3' (SEQ ID NO. 5) and
   5'-TGAGTCGTATTAC-3' (SEQ ID NO. 6)

and analogs or derivatives thereof with modified or derivatized nucleotide bases but which retain their complementarity.

14. A modular oligonucleotide wherein said modular oligonucleotide comprises a pair of oligonucleotides, wherein said pair of oligonudleotides is selected from the group consisting of:

5'-NNAAGCTTACT-3' (SEQ ID NO. 7) and
5'-GGCCGTCGTTTTACAACG-3' (SEQ ID NO. 8)
5'-NNNNAATTCGCCCTATAG-3' (SEQ ID NO. 9) and
5'-TGAGTCGTATTAC-3' (SEQ ID NO. 6)
5'-GAATTCACGGAAATCATG-3' (SEQ ID NO. 10) and
5'-GTCATAGCTGTTTCCTGT-3' (SEQ ID NO. 11)
5'-TCCAGCTTTTGTTCC-3' (SEQ ID NO. 12) and
5'-CTTTAGTGAGGGTTAATT-3' (SEQ ID NO. 13)
5'-NNTTGAGTATTCTATAG-3' (SEQ ID NO. 14) and
5'-TGTCACCTAAATAGCT-3' (SEQ ID NO. 15)
5'-TCTAGAGTCGACCTGCAG-3' (SEQ ID NO. 16) and
5'-GCATGCAAGCTT-3' (SEQ ID NO. 17)
5'-ACCCAATTCGCCCTATAG-3' (SEQ ID NO. 5) and
5'-TGAGTCGTATTAC-3' (SEQ ID NO. 6)

and analogs or derivatives thereof with modified or derivatized nucleotide bases but which retain their complementarity.

15. A kit comprising at least the following:

a modular oligonucleotide as defined in claim 14.

16. A method of determining the nucleotide sequence of a nucleic acid insert in a vector wherein sequencing products are generated by performing primer extension reactions on said vector, the sequencing products are isolated by a method as claimed in claim 1 or 2, the products thus isolated are separated and the labels carried on said sequencing products are visualized to allow determination of the sequence of said insert or a portion thereof.

* * * * *

UNITED STATES PATENT AND TRADEMARK OFFICE
CERTIFICATE OF CORRECTION

PATENT NO. : 6,482,592 B1
DATED : November 19, 2002
INVENTOR(S) : Lundeberg et al.

It is certified that error appears in the above-identified patent and that said Letters Patent is hereby corrected as shown below:

<u>Column 59,</u>
Lines 47 and 53, delete "longing" and insert therefore -- cloning --.
Line 61, delete "$\geqq 9 \geqq 18$" and insert therefore -- $\geq 9 \leq 18$ --.

Signed and Sealed this

Twenty-sixth Day of October, 2004

JON W. DUDAS
*Director of the United States Patent and Trademark Office*